US011369676B2

(12) United States Patent
Dilly

(10) Patent No.: US 11,369,676 B2
(45) Date of Patent: Jun. 28, 2022

(54) METHODS OF ORAL IMMUNOTHERAPY

(71) Applicant: Société des Produits Nestlé S.A., Vevey (CH)

(72) Inventor: Stephen G. Dilly, Brisbane, CA (US)

(73) Assignee: Société des Produits Nestlé S.A., Vevey (CH)

( * ) Notice: Subject to any disclaimer, the term of this patent is extended or adjusted under 35 U.S.C. 154(b) by 4 days.

(21) Appl. No.: 16/178,502

(22) Filed: Nov. 1, 2018

(65) Prior Publication Data
US 2019/0167785 A1 Jun. 6, 2019

Related U.S. Application Data

(60) Provisional application No. 62/674,478, filed on May 21, 2018, provisional application No. 62/637,903, filed on Mar. 2, 2018, provisional application No. 62/631,406, filed on Feb. 15, 2018, provisional application No. 62/580,999, filed on Nov. 2, 2017.

(51) Int. Cl.
| *A61K 39/35* | (2006.01) |
| *A61K 9/00* | (2006.01) |
| *G01N 33/68* | (2006.01) |
| *A61P 37/08* | (2006.01) |
| *A61K 39/00* | (2006.01) |

(52) U.S. Cl.
CPC ............ *A61K 39/35* (2013.01); *A61K 9/0053* (2013.01); *A61P 37/08* (2018.01); *G01N 33/6854* (2013.01); *A61K 2039/542* (2013.01); *A61K 2039/545* (2013.01); *G01N 2800/52* (2013.01)

(58) Field of Classification Search
None
See application file for complete search history.

(56) References Cited

U.S. PATENT DOCUMENTS

| 3,809,767 | A | 5/1974 | Sair et al. |
| 9,198,869 | B2 | 12/2015 | Walser et al. |
| 9,492,535 | B2 | 11/2016 | Walser et al. |
| 10,086,068 | B2 | 10/2018 | Walser et al. |
| 2004/0234548 | A1 | 11/2004 | Caplan |
| 2008/0317878 | A1 | 12/2008 | Li et al. |
| 2009/0111702 | A1 | 4/2009 | Sampson et al. |
| 2014/0093541 | A1 | 4/2014 | Clark et al. |
| 2016/0030289 | A1 | 2/2016 | Walser et al. |
| 2016/0051593 | A1 | 2/2016 | Raff |
| 2018/0042816 | A1 | 2/2018 | Walser et al. |
| 2018/0200361 | A1 | 7/2018 | Simon et al. |

FOREIGN PATENT DOCUMENTS

| WO | WO-2010/069595 A1 | 6/2010 |
| WO | WO-2012/001074 A2 | 1/2012 |
| WO | WO-2012/001074 A3 | 1/2012 |
| WO | WO-2012/123759 A1 | 9/2012 |
| WO | WO-2014/159607 A1 | 10/2014 |
| WO | WO-2014/159609 A1 | 10/2014 |
| WO | WO-2016/033094 A1 | 3/2016 |
| WO | WO-2018/132733 A1 | 7/2018 |

OTHER PUBLICATIONS

Burman et al. 'High arachis hypogaea allergen 2 immunoglobulin E levels predict responses to exposure to a small amount of peanut.' Acta Pdiatrica. Published by John Wiley & Sons Ltd 2018 107, p. 2216.*
Anagnostou et al. 'Efficacy and safety of high-dose peanut oral immunotherapy with factors predicting outcome.' Clinical & Experimental Allergy, 41, 1273-1281, 2011.*
Wensing et al. 'The distribution of individual threshold doses eliciting allergic reactions in a population with peanut allergy.' J Allergy Clin Immunol. Dec. 2002; 110(6):915-20. doi: 10.1067/mai.2002.129235.*
Adelman, D.C. (Oct. 17, 2018). "Efficacy and Safety of AR101 in Peanut Allergy: Results from a Phase 3, Randomized, Double-Blind Placebo Controlled Trial (PALISDAE)," *International Food Allergy & Anaphylaxis Alliance (IFAAA) Meeting*, Copenhagen, Denmark.
Anagnostau, K. et al. (2014, e-pub. Jan. 30, 2014). "Assessing The Efficacy Of Oral Immunotherapy For The Desensitisation Of Peanut Allergy In Children (STOP II): A Phase 2 Randomised Controlled Trial," *Lancet* 383:1297-1304.
Ballmer-Weber B.K. et al. (2015). "IgE Recognition Patterns In Peanut Allergy Are Age Dependent: Perspectives Of The Europrevail Study," *Allergy* 70:391-407.
Bernard, H. (Nov. 14, 2007, e-pub. Oct. 20, 2007). "Identification of a New Natural ARA h 6 Isoform and of its Proteolytic Product as Major Allergens in Peanut," *Journal of Agricultural and Food Chemistry* 55(23):9663-9669.
Beyer, K et al. (Oct. 19, 2018). "Adrenaline Use and Reaction-Severity During the Exit Double-Blind, Placebo-Controlled Food Challenge (DBPCFC) with Peanut in Subjects Aged 4-17 Years in PALISADE, a Phase 3, Randomised, Double-Blind, Placebo-Controlled Trial," presented at the *Food Allergy and Anaphylaxis Meeting (FAAM)*, Copenhagen Denmark.

(Continued)

*Primary Examiner* — Nora M Rooney
(74) *Attorney, Agent, or Firm* — Morrison & Foerster LLP

(57) ABSTRACT

The present disclosure relates to improved oral immunotherapy methods for treating food allergies, and particularly peanut allergy. Biomarkers, such as a level of peanut-specific IgE and/or peanut-specific IgG4s are used by the methods described herein. Such methods include a method of treating a subject for a peanut allergy, methods of assessing the suitability of a treatment for a peanut allergy, a method of evaluating a symptom in a subject during the course of treatment of a peanut allergy, a method of monitoring treatment for a peanut allergy in a subject, a method of reducing the risk or incidence of an adverse event in a subject receiving treatment for a peanut allergy, a method of adjusting a dose of an allergenic peanut composition, and a method of assessing a likelihood of an allergic reaction that requires administration of epinephrine to a subject receiving treatment for a peanut allergy.

43 Claims, 10 Drawing Sheets

(56) References Cited

OTHER PUBLICATIONS

Bird, J.A et al. (Mar./Apr. 2018). "Efficacy and Safety Of AR101in Oral Immunotherapy 1 For Peanut Allergy: Results Of ARC001, a Randomized, Double-Blind, Placebo-Controlled Phase-2 Clinical Trial," *All. Clin. Immunol. In Prac.* 6(2):476-485.

Blumchen, K. et al. (2010). "Oral Peanut Immunotherapy In Children With Peanut Anaphylaxis," *J. Allergy Clin. Immunol.* 126:83-91.

Chen, X. et al. (2013, e-pub. Oct. 16, 2012). "Ara h 2 and Ara h 6 Have Similar Allergenic Activity and Are Substantially Redundant," *Int. Arch. Allergy Immunol.* 160:251-258.

Clark, A.T. et al. (Aug. 2003). "Interpretation Of Tests For Nut Allergy In One Thousand Patients, In Relation To Allergy Or Tolerance," *Clinical and Experimental Allergy* 33(8):1041-1045.

De Oliveira, L.C.L. et al. (2013). "The Value of Specific IgE to Peanut and Its Component Ara h 2 in the Diagnosis of Peanut Allergy," J. Allergy Clin. Immunol. 1(4):394-398.

Du Toit, G. et al. (May 2018). "Efficacy and Safety of AR101 in Peanut Allergic Patients Aged 4-55: Results from an International Phase 3, Randomised, Double-Blind, Placebo Controlled Trial (PALISADE)," presented at the European Academy of Allergy and Clinical Immunology (EAACI), Munich, Germany.

Flinterman, A.E. et al. (2006). "Determination Of No-Observed-Adverse-Effect Levels and Eliciting Doses In A Representative Group Of Peanut-Sensitized Children," *Journal of Allergy and Clinical Immunology* 117(2):448-454.

Grimshaw, K.E. et al. (2015). "Incidence and risk Factors For Food Hypersensitivity In UK Infants: Results From A Birth Cohort Study," *Clin Transl Allergy* 6:1, 13 pages.

Hofmann, A.M. et al. (Aug. 2009). "Safety of A Peanut Oral Immunotherapy Protocol In Peanut Allergic Children," *J. Allergy Clin. Immunol.* 124(2):286-291, 14 pages.

Hourihane, J.O. et al. (Jun. 1997). "Clinical Characteristic Of Peanut Allergy," *Clinical and Experimental Allergy* 27(6):634-639.

Hourihane, J.O. et al. (Sep. 30-Oct. 2, 2018) "Abstract OP.091: Efficacy and Safety Of AR101: Results Of The Phase 3 Peanut Allergy Oral Immunotherapy Study For Desensitization (PALISADE) Trial," *Abstracts, 2018 Annual Meeting of the British Society for Allergy and Clinical Immunology.*

Jones, S.M. et al. (2009, e-pub. Jul. 6, 2009). "Clinical Efficacy and Immune Regulation With Peanut Oral Immunotherapy," *J. Allergy Clin. Immunol.* 124(2):292-30197. 20 pages.

Jones, S.M. et al. (2014). "State Of The Art On Food Allergen Immunotherapy: Oral, Sublingual, and Epicutaneous," *J. Allergy Clin. Immunol.* 133:318-323.

Jones, S.M. et al. (Mar. 4, 2018). "Efficacy and Safety of AR101 in Peanut Allergy: Results from a Phase 3, Randomized, Double-Blind, Placebo-Controlled Trial (PALISADE)," *American Academy of Allergy, Asthma & Immunology.*

Kim, E.H. et al. (Mar. 2011). "Sublingual Immunotherapy For Peanut Allergy: Clinical and Immunologic Evidence Of Desensitization," *J. Allergy Clin. Immunol.* 127(3):640-646, 19 pages.

Koid, A. et al. (2012). "Purified Natural Ara h 6: An Important Marker for IgE Responses to Peanut," *The Journal of Immunology* 188:177.15, 1 page.

Koid, A.E. et al. (Jan. 8, 2014). "Ara h 6 Complements Ara h 2 as an Important Marker for IgE Reactivity to Peanut," *J. Agric. Food Chem.* 62(1):2016-2013, 18 pages.

Koppelman, S.J. et al. (Feb. 2001). "Quantification of Major Peanut Allergens Ara h 1 and Ara h 2 in The Peanut Varieties Runner, Spanish, Virginia, and Valencia, Bred in Different Parts of the World," *Allergy* 56(2):132-137.

Koppelman, S.J. et al. (2004). "Relevance of Ara h1, Ara h2 and Ara h3 in Peanut-Allergic Patients, as Determined by Immunoglobulin E Western Blotting, Basophil-Histamine Release and Intracutaneous Testing: Ara h2 Is The Most Important Peanut Allergen," *Clin. Exp. Allergy* 34:583-590.

Maloney, J.M. et al. (2008, e-pub. May 27, 2008). "The Use Of Serum-Specific IgE Measurements For The Diagnosis Of Peanut, Tree Nut, and Seed Allergy," *Journal of Allergy and Clinical Immunology* 122(1):145-151.

Mondoulet, L. et al. (Feb. 21, 2012). "Epicutaneous Immunotherapy (EPIT) Blocks the Allergic Esophago-Gastro-Enteropathy Induced by Sustained Oral Exposure to Peanuts in Sensitized Mice," *PLoS One* 7(2):e31967, 10 pages.

Nicolaou, N. et al. (2010). "Allergy Or Tolerance In Children Sensitized To Peanut: Prevalence and Differentiation Using Component-Resolved Diagnostics," *J. Allergy Clin. Immunol.* 125:191-197.

Pajno, G.B. et al. (2014). "Oral Immunotherapy for Treatment of Immunoglobulin E-Mediated Food Allergy: The Transition to Clinical Practice," *Pediatr Allergy Immunol Pulmonol.* 27:42-50.

Peeters, K.A.B.M. et al. (2007). "Does Skin Prick Test Reactivity To Purified Allergens Correlate With Clinical Severity Of Peanut Allergy?" *Clinical and Experimental Allergy* 37:108-115.

Pele, M. (2010). "Peanut Allergens," *Romanian Biotechnological Letters* 15(2):5201-5212.

Rance, F. et al. (2002). "Improved Screening For Peanut Allergy By The Combined Use Of Skin Prick Tests And Specific IgE Assays," *Journal of Allergy and Clinical Immunology* 109(6):1027-1033.

Roberts, G. et al. (2005). "Diagnosing Peanut Allergy With Skin Prick and Specific IgE Testing," *J. Allergy Clin. Immunol.* 115:1291-1296.

Sampson, H.A. et al. (1997). "Clinical Aspects Of Allergic Disease: Relationship Between Food-Specific IgE Concentrations and The Risk Of Positive Food Challenges In Children and Adolescents," *J. Allergy Clin. Immunol.* 100:444-451.

Santos, A.F. et al. (2014). "Food, Drug, Insect Sting Allergy, and Anaphylaxis: Basophil Activation Test Discriminates Between Allergy and Tolerance In Peanut-Sensitized Children," *J. Allergy Clin. Immunol.* 134:645-652.

Sher, E. et al. (May 2018). "Efficacy and Safety of AR101 in Peanut Allergy: Results from a Phase 3, Randomized, Double-Blind Placebo Controlled Trial (PALISDAE)," presented at the *Eastern Allergy Conference (EAC)*, Palm Beach, Florida.

Shreffler, W.G. et al. (2004). "Microarray immunoassay: Association Of Clinical History, in vitro IgE Function, and Heterogeneity Of Allergenic Peanut Epitopes," *J. Allergy Clin. Immunol.* 113:776-782.

Sicherer, S.H. et al. (Jul. 1998). "Clinical Features of Acute Allergic Reactions to Peanut and Tree Nuts in Children," *Pediatrics* 102(1):1-6, 8 pages.

Sicherer, S.H. (Nov. 1999). "Food Allergy: When and How To Perform Oral Food Challenges," *Pediatr. Allergy Immunol.* 10(4):226-234.

Sicherer, S.H. (2011, e-pub. Jan. 13, 2011). "Epidemiology Of Food Allergy," *J. Allergy Clin. Immunol.* 127(3):594-602.

Sicherer, S.H. et al. (2014). "Food allergy: Epidemiology, Pathogenesis, Diagnosis, and Treatment," *J. Allergy Clin. Immunol.* 133-291-307.

Singh, H. et al. (Oct. 2011). "Developing RP-HPLC Method For Detection Of Peanut Allergens," in AACC International Annual Meeting, Oct. 16-19, 2011. Retrieved from the Internet <http://www.aaccnet.org/meetings/Documents/2011Abstracts/p11ma199.htm>, last visited Feb. 17, 2016, 1 page. (Abstract Only).

Skolnick, H.S. et al. (2001). "Food and Drug Reactions and Anaphylaxis: The Natural History Of Peanut Allergy," J. Allergy Clin. Immunol. 107:367-374.

Skripak, J.M. et al. (2008, e-pub. Oct. 28, 2008). "A Randomized, Double-Blind, Placebo-Controlled Study Of Milk Oral Immunotherapy For Cow's Milk Allergy," *J. Allergy Clin. Immunol.* 122(6):1154-1160.

Vander Leek, T.K. et al. (Dec. 2000). "The Natural History Of Peanut Allergy In Young Children and its Association With Serum Peanut-Specific IgE," *J. Pediatr.* 137(6):749-755.

Van Der Zee, T. et al. (2011). "The Eliciting Dose Of Peanut In Double-Blind, Placebo-Controlled Food Challenges Decreases With Increasing Age and Specific IgE Level In Children and Young Adults," *J. Allergy Clin. Immunol.* 128:1031-1036.

Van Veen, W.J. et al. (2013). "Predictive Value Of Specific IgE For Clinical Peanut Allergy In Children: Relationship With Eczema,

(56) References Cited

OTHER PUBLICATIONS

Asthma, and Setting (Primary Or Secondary Care)," *Clinical and Translational Allergy* 3:34, 7 pages.

Varshney, P. et al. (2009, e-pub. Nov. 13, 2009). "Adverse Reactions During Peanut Oral Immunotherapy Home Dosing," *J. Allergy Clin. Immunol.* 124(6):1351-1352.

Varshney, P. et al. (2011). "A Randomized Controlled Study Of Peanut Oral Immunotherapy: Clinical Desensitization and Modulation Of The Allergic Response," *J. Allergy Clin. Immunol.* 127:654-660.

Vereda, A. et al. (Sep. 30-Oct. 5, 2018). "Abstract 139:Efficacy and Safety of AR101: Results of the Phase 3 Peanut Allergy Oral Immunotherapy Study for Desensitization (PALISADE) Trial," *Abstract: Allergy Across the Life Course—From Origins Towards Prevention, 32$^{nd}$ Symposium of the Collegium International Allergologium*.

Vickery, B.P. et al. (2013, e-pub. Nov. 27, 2012). "Peanut Oral Immunotherapy Modifies IgE and IgG$_4$ Responses To Major Peanut Allergens," *Journal of Allergy and Clinical Immunology* 131(1):128-134.

Virkud, Y.V. et al. (2017). "Novel Baseline Predictors Of Adverse Events During Oral Immunotherapy In Children With Peanut Allergy," *J. Allergy Clin. Immunol* 139:882-888.

Wainstein, B.K. et al. (Jun. 2010). "Prediction of Anaphylazis During Peanut Food Challenge: Usefulness of the Peanut Skin Prick Test (SPT) and Specific IgE Level," *Pediatr. Allergy Immunol.* 21(4)(Pt. 1):603-611.

U.S. Appl. No. 16/111,102, Walser et al., filed Aug. 23, 2018. (Copy not submitted herewith pursuant to the waiver of 37 C.F.R. § 1.98(a)(2)(iii) issued by the Office on Sep. 21, 2004).

U.S. Appl. No. 16/289,370, Walser et al., filed Feb. 28, 2019. (Copy not submitted herewith pursuant to the waiver of 37 C.F.R. § 1.98(a)(2)(iii) issued by the Office on Sep. 21, 2004).

U.S. Appl. No. 16/396,493, Raff et al., filed Apr. 26, 2019. (Copy not submitted herewith pursuant to the waiver of 37 C.F.R. § 1.98(a)(2)(iii) issued by the Office on Sep. 21, 2004).

Publication Information for Burman, J. et al. (2018). "High Arachis Hypogaea Allergen 2 Immunoglobulin E Levels Predict Responses To Exposure To A Small Amount Of Peanut Protein," Acta Paediatrica 107:2216, retrieved from Internet <https://onlinelibrary.wiley.com/doi/abs/10.1111/apa.14511>, last visited Feb. 7, 2021.

International Preliminary Report on Patentability Search Report for PCT Application PCT/US20187/058777, dated May 5, 2020, filed Nov. 1, 2018, 17 pages.

International Search Report and Written Opinion of the International Searching Authority, dated Feb. 22, 2019, for PCT Application No. PCT/US2018/58777, filed Nov. 1, 2018, 23 pages.

Michaud, E. et al. (Apr. 29, 2015). "Peanut Oral Immunotherapy in Adolescents: Study Protocol For a Randomized Controlled Trial," Trials 16(1):197, 6 pages.

Partial Supplementary European Search Report, dated Aug. 3, 2021, for European Patent Application No. 18871949.6, 18 pages.

Schurlock, A.M. et al. (Nov. 1, 2004). "Peanut Allergenicity," Annals of Allergy, Asthma & Immunology 93(5):S12-S18.

\* cited by examiner

| Considerations by psIgE cohort | | |
|---|---|---|
| | psIgE>100 | psIgE≤100 |
| % of PA population | ~20% | ~80% |
| Severity profile | Same | Same |
| Sensitivity level | Same | Same |
| Need for AR101 | High | High |
| Drop-out rate on AR101 | ~40% | ~0% |

FIG. 1B

METHODS OF ORAL IMMUNOTHERAPY

CROSS-REFERENCE TO RELATED APPLICATIONS

This application claims priority benefit to U.S. Provisional Application No. 62/580,999, filed on Nov. 2, 2017, entitled "METHODS OF ORAL IMMUNOTHERAPY"; U.S. Provisional Application No. 62/631,406, filed on Feb. 15, 2018, entitled "METHODS OF ORAL IMMUNOTHERAPY"; U.S. Provisional Application No. 62/637,903, filed on Mar. 2, 2018, entitled "METHODS OF ORAL IMMUNOTHERAPY"; and U.S. Provisional Application No. 62/674,478, filed on May 21, 2018, entitled "METHODS OF ORAL IMMUNOTHERAPY"; each of which are incorporated herein by reference for all purposes.

FIELD OF THE INVENTION

The present disclosure relates to methods for treating food allergies.

BACKGROUND OF THE INVENTION

Food allergy is an adverse reaction to food that is triggered by the immune system. Food allergies affect 3% of the overall population and up to 4% to 6% of children (Sicherer, "Epidemiology of food allergy," J Allergy Clin Immunol 2011; 127: 594-602). Allergic reactions to food may be IgE mediated (causing immediate symptoms and possible anaphylaxis), non-IgE mediated (cell-mediated reactions with more delayed symptoms), or a combination of both. Previous reports suggest that over 80% of peanut-allergic patients have a peanut-specific IgE level of 100 kU/L or less. See, for example, Hourihane et al., *Clinical characteristic of peanut allergy*, Clinical and Experimental Allergy, vol. 27, no. 6, pp. 634-639 (1997); Maloney et al., *The use of serum-specific IgE measurements for the diagnosis of peanut, tree nut, and seed allergy*, Journal of Allergy and Clinical Immunology, vol. 122, no. 1, pp. 145-151 (2008); and Rance et al., *Improved screening for peanut allergy by the combined use of skin prick tests and specific IgE assays*, Journal of Allergy and Clinical Immunology, vol. 109, no. 6, pp. 1027-1033 (2002). Previous reports further suggest either that peanut-specific IgE has no correlation with reaction severity (see, for example, Clark et al., *Interpretation of tests for nut allergy in one thousand patients, in relation to allergy or tolerance*, Clinical and Experimental Allergy, vol. 33, no. 8, pp. 1041-1045 (2003) and Flinterman et al., *Determination of no-observed-adverse-effect levels and eliciting doses in a representative group of peanut-sensitized children*, Journal of Allergy and Clinical Immunology, vol. 117, no. 2, pp. 448-454 (2006)), or that higher levels of peanut-specific IgE and/or increased epitope diversity are associated with severe reactions (see, for example, Vickery et al., *Peanut oral immunotherapy modifies IgE and IgG4 responses to major peanut allergens*, Journal of Allergy and Clinical Immunology, vol. 131, no. 1, pp. 128-134 (2013).

The current standard of care for treating food allergies includes identifying the responsible food allergen and educating patients on how to avoid ingesting the food unknowingly and how to recognize and treat early signs of an allergic reaction in case of accidental ingestion. Aside from avoidance of the offending food, there is no approved disease-modifying therapy for treating food allergies at this time. In recent years, there is an increasing interest in oral immunotherapy (OIT) for the treatment of food allergy, and several clinical trials have shown promising results. Immunotherapy, in general, entails gradual increasing exposure to allergens in the hopes of desensitization (temporary loss of responsiveness due to continuous exposure) and/or promoting tolerance (permanent immunologic nonresponse). Oral immunotherapy involves the regular administration of small amounts of allergen by the oral route to first induce desensitization, then over time induce tolerance to the allergen. Although OIT appears to be a promising option for the treatment of food allergy, it is associated with high rates of adverse reactions (Skripak et al., "A randomized, double-blind, placebo-controlled study of milk oral immunotherapy for cow's milk allergy. J Allergy Clin Immunol. 2008; 122(6): 1154-1160; Jones et al., "Clinical efficacy and immune regulation with peanut oral immunotherapy," J Allergy Clin Immunol. 2009; 124(2):292-300; and Varshney et al., "Adverse reactions during peanut oral immunotherapy home dosing," J Allergy Clin Immunol. 2009; 124(6):1351-1352). Subjects undergoing OIT on experience adverse reactions at an early stage of the therapy, such as at the beginning of the therapy which is usually initiated with very small amounts of the food allergen, or at a later stage as the dose of the food allergen gradually increases. Consequently, subjects experiencing adverse reactions cannot be benefited by oral immunotherapy alone.

Thus, there is a need in the art for improved methods for treating food allergies. There is also need in the art for distinguishing between subjects with food allergies as likely or substantially less likely to respond favorably to OIT alone.

SUMMARY OF THE INVENTION

Described herein is a method of treating a subject for a peanut allergy, comprising administering to the subject at least one dose of an allergenic peanut composition, wherein the subject is selected for treatment based on having a level of peanut-specific IgEs at or below a predetermined threshold. In some embodiments, the predetermined threshold for the level of peanut-specific IgEs is about 100 kU/L. In some embodiments, the level of peanut-specific IgEs is determined prior to initiating treatment of the peanut allergy. In some embodiments, the does is administered to the subject as part of an oral immunotherapy dosing regimen. In some embodiments, the dose is administered to the subject during an initial escalation phase of the oral immunotherapy dosing regimen. In some embodiments, the dose is administered to the subject during an up-dosing phase of the oral immunotherapy dosing regimen. In some embodiments, the dose is administered to the subject during a maintenance phase of the oral immunotherapy dosing regimen. In some embodiments, the method comprises receiving the level of peanut-specific IgEs. In some embodiments, the method comprises measuring the level of peanut-specific IgEs.

Also described herein is a method of treating a subject for a peanut allergy, comprising administering to the subject at least one dose of an allergenic peanut composition, wherein the subject undergoes heightened monitoring for an allergenic reaction if a level of peanut-specific IgEs in the subject is above a predetermined threshold. In some embodiments, the predetermined threshold of the level of peanut-specific IgEs is about 100 kU/L. In some embodiments, heightened monitoring comprises a longer clinical visit following administration of the dose compared to a subject having a level of peanut-specific IgEs at or below the predetermined threshold. In some embodiments, heightened monitoring comprises active monitoring for the allergic reaction. In some embodiments, active monitoring comprises measuring a heart rate, blood pressure, respiratory rate, or blood oxygen. In some embodiments, the allergic reaction is hypersensitivity, anaphylaxis, a gastrointestinal symptom, or eosinophilic esophagitis. In some embodiments, the dose is administered to the subject as part of an oral immunotherapy dosing regimen. In some embodiments, the dose is administered to the subject during an initial escalation phase of the oral immunotherapy regimen. In some embodiments, the dose is administered to the subject during an up-dosing phase of an oral immunotherapy regimen. In some embodiments, the dose is administered to the subject during a maintenance phase of an oral immunotherapy regimen.

In some embodiments of the methods described above, the method comprises receiving the level of peanut-specific IgEs. In some embodiments, the method comprises measuring the level of peanut-specific IgEs.

Further described herein is a method of assessing the suitability of a treatment for a peanut allergy in a subject, comprising receiving a level of peanut-specific IgEs in the subject; and assessing the suitability of the treatment, wherein the subject having a level of peanut-specific IgEs at or below a predetermined threshold indicates that the treatment is suitable for the subject. In some embodiments, the predetermined threshold of the level of peanut-specific IgEs is about 100 kU/L. In some embodiments, the treatment is an oral immunotherapy dosage regimen. In some embodiments, the method comprises initiating administration of the oral immunotherapy dosage regimen to the subject. In some embodiments, initiating administration of the oral immunotherapy dosage regimen to the subject comprises administering an initial escalation phase of the oral immunotherapy regimen to the subject. In some embodiments, receiving the level of the peanut-specific IgEs in the subject comprises measuring the level of peanut-specific IgEs in the subject. These methods are preferably performed in vitro.

Also described herein is a method of evaluating a symptom in a subject during the course of treatment of a peanut allergy, comprising receiving a level of peanut-specific IgEs in the subject having an adverse event; and determining whether the symptom is related to the treatment, wherein a level of peanut-specific IgEs at or below a predetermined threshold indicates that the adverse event is not caused by the treatment. In some embodiments, the level of peanut-specific IgE is determined prior to initiating the course of treatment. In some embodiments, the level of peanut-specific IgE is determined during the course of treatment. In some embodiments, the level of peanut-specific IgE is determined when the subject is symptomatic. In some embodiments, the predetermined threshold of the level of peanut-specific IgEs is about 100 kU/L. In some embodiments, the treatment is an oral immunotherapy dosage regimen. In some embodiments, the symptom is a gastrointestinal symptom. In some embodiments, the gastrointestinal symptom is vomiting or abdominal pain. In some embodiments, the method comprises delaying a dose increase during an up-dosing phase of the treatment if the symptom is determined to be related to the treatment. In some embodiments, the method comprises reducing or delaying a dose of an allergenic peanut composition administered to the subject if the symptom is determined to be related to the treatment. In some embodiments, the method comprises terminating the treatment if the symptom is determined to be related to the treatment. In some embodiments, receiving the level of peanut-specific IgEs comprises measuring the level of peanut-specific IgEs. These methods are preferably performed in vitro.

Further described herein is a method of monitoring treatment for a peanut allergy in a subject, comprising measuring a level of peanut-specific IgEs in the subject during the course of treatment. In some embodiments, the treatment is an oral immunotherapy dosage regimen. In some embodiments, the method comprises reducing or delaying a dose of an allergenic peanut composition if the level of peanut-specific IgEs is above a predetermined threshold. In some embodiments, the method comprises delaying a dose increase during an up-dosing phase of the treatment if the level of peanut-specific IgEs is above a predetermined threshold. In some embodiments, the method comprises terminating the treatment if the level of peanut-specific IgEs is above a predetermined threshold. In some embodiments, the method comprises increasing the dose if the level of peanut-specific IgEs is at or below a predetermined threshold. In some embodiments, the predetermined threshold is about 100 kU/L. In some embodiments, the level of peanut-specific IgEs is measured following an initial escalation phase of the treatment. In some embodiments, the method comprises the level of peanut-specific IgEs is measured during an up-dosing phase of the treatment. These methods are preferably performed in vitro.

Also described herein is a method of reducing the risk or incidence of an adverse event in a subject receiving treatment for a peanut allergy, comprising: receiving a level of peanut-specific IgEs in the subject; and reducing a dose, delaying a dose, or delaying an increase of a dose of an allergenic peanut composition if the level of peanut-specific IgEs is above a predetermined threshold. In some embodiments, the treatment is oral immunotherapy. In some embodiments, the predetermined level of the peanut-specific IgEs is about 100 kU/L. In some embodiments, receiving the level of the peanut-specific IgEs in the subject comprises measuring the level of peanut-specific IgEs in the subject. In some embodiments, the adverse event is an allergic reaction. In some embodiments, the method comprises reducing the dose of the allergic peanut composition if the level of peanut-specific IgEs is above the predetermined threshold. In some embodiments, the dose of the allergenic peanut composition is reduced during an up-dosing phase of the therapy. In some embodiments, the method comprises delaying the dose of the allergic peanut composition if the level of peanut-specific IgEs is above the predetermined threshold. In some embodiments, the method comprises delaying the increase of the dose of the allergic peanut composition during an up-dosing phase of the therapy if the level of peanut-specific IgEs is above the predetermined threshold. In some embodiments, the method comprises administering the dose to the subject.

Further described herein is a method of adjusting a dose of an allergenic peanut composition, comprising: administering a first dose of the allergenic peanut composition to a subject with a peanut allergy; receiving a level of peanut-specific IgEs in the subject after administration of the first dose; and administering a second dose of the allergenic peanut composition to the subject, wherein the second dose is based on the first dose and the level of peanut-specific IgEs in the subject. In some embodiments, the second dose is lower than the first dose if the level of peanut-specific IgEs is above a predetermined threshold. In some embodiments, the administration of the second dose is delayed if the level of peanut-specific IgEs is above a predetermined threshold. In some embodiments, the second dose is the same as the first dose if the level of peanut-specific IgEs is above a predetermined threshold. In some embodiments, the second dose is increased relative to the first dose if the level of peanut-specific IgEs is at or below the predetermined threshold. In some embodiments, the predetermined threshold is about 100 kU/L. In some embodiments, receiving the level of peanut-specific IgEs in the subject comprises measuring the level of peanut-specific IgEs.

Also described herein is a method of assessing a likelihood of an allergic reaction that requires administration of epinephrine to a subject receiving treatment for a peanut allergy, wherein the treatment comprises administration of at least one dose of an allergenic peanut composition, the method comprising: receiving a level of peanut-specific IgEs in the subject; and assessing the likelihood of an allergic reaction that requires administration of epinephrine to the patient, wherein a level of peanut-specific IgEs at or below a predetermined threshold indicates a reduced likelihood of an allergic reaction that requires administration of epinephrine during treatment, and wherein a level of peanut-specific IgEs above the predetermined threshold indicates an increased likelihood of an allergic reaction that requires administration of epinephrine during treatment. In some embodiments, the method further comprises administering to the subject one or more doses of an allergenic peanut composition if the level of peanut-specific IgEs is at or below the predetermined threshold. In some embodiments, the predetermined threshold of the level of peanut-specific IgEs is about 100 kU/L. In some embodiments, the treatment is an oral immunotherapy dosing regimen. In some embodiments, the method comprises recommending to the subject that the subject have immediate access to at least two doses of injectable epinephrine for treatment of the allergic reaction if the subject has a level of peanut-specific IgEs above the predetermined threshold. In some embodiments, each dose of epinephrine is about 0.15 mg of injectable epinephrine if the subject weighs less than about 30 kilograms, or about 0.3 mg of injectable epinephrine if the subject weighs about 30 kilograms or more.

In some embodiments of the methods described above, the subject is a human. In some embodiments, the subject is about 17 years of age or younger. In some embodiments, is about 4 years of age to about 17 years of age.

In some embodiments of the methods described above, the method comprises measuring the level of peanut-specific IgEs in the subject prior to initiating treatment for the peanut allergy. In some embodiments, the level of peanut-specific IgEs in the subject is a level determined prior to initiating treatment of the peanut allergy. In some embodiments, the level of peanut-specific IgEs in the subject is a level determined during the course of treatment.

In some embodiments of the methods described above, the level of peanut-specific IgEs or the level of peanut-specific IgG4 corresponds to a level as measured by a fluorescence enzyme immunoassay auto-analyzer. In some embodiments, the level of peanut-specific IgEs or the level of peanut-specific IgG4 is measured by a fluorescence enzyme immunoassay auto-analyzer. In some embodiments, the level is measured in vitro.

Also described herein is an allergenic peanut composition for use in treating a subject for a peanut allergy, wherein (as discussed above): the subject is selected for treatment based on having a level of peanut-specific IgEs at or below a predetermined threshold; the subject undergoes heightened monitoring for an allergenic reaction if a level of peanut-specific IgEs in the subject is above a predetermined threshold; a level of peanut-specific IgEs in the subject is measured during the course of treatment and, optionally, a dosage of the composition is reduced or delayed, or an increase in dosage is delayed, if the level of peanut-specific IgEs is above a predetermined threshold; and/or a first and a second dose of the composition are administered, wherein the second dose is based on the first dose and the level of peanut-specific IgEs in the subject.

Also described herein is the use of an allergenic peanut composition in the manufacture of a medicament for treating a subject for a peanut allergy, wherein (as discussed above): the subject is selected for treatment based on having a level of peanut-specific IgEs at or below a predetermined threshold; the subject undergoes heightened monitoring for an allergenic reaction if a level of peanut-specific IgEs in the subject is above a predetermined threshold; a level of peanut-specific IgEs in the subject is measured during the course of treatment and, optionally, a dosage of the composition is reduced or delayed, or an increase in dosage is delayed, if the level of peanut-specific IgEs is above a predetermined threshold; a first and a second dose of the composition are administered, wherein the second dose is based on the first dose and the level of peanut-specific IgEs in the subject.

In some embodiments of the methods described above, the subject is a human.

BRIEF DESCRIPTION OF THE DRAWINGS

FIG. 1B shows considerations for patient cohorts in the treatment of peanut allergy by OIT by peanut-specific IgE levels after preliminary analysis.

DESCRIPTION OF THE INVENTION

Figure 1A:
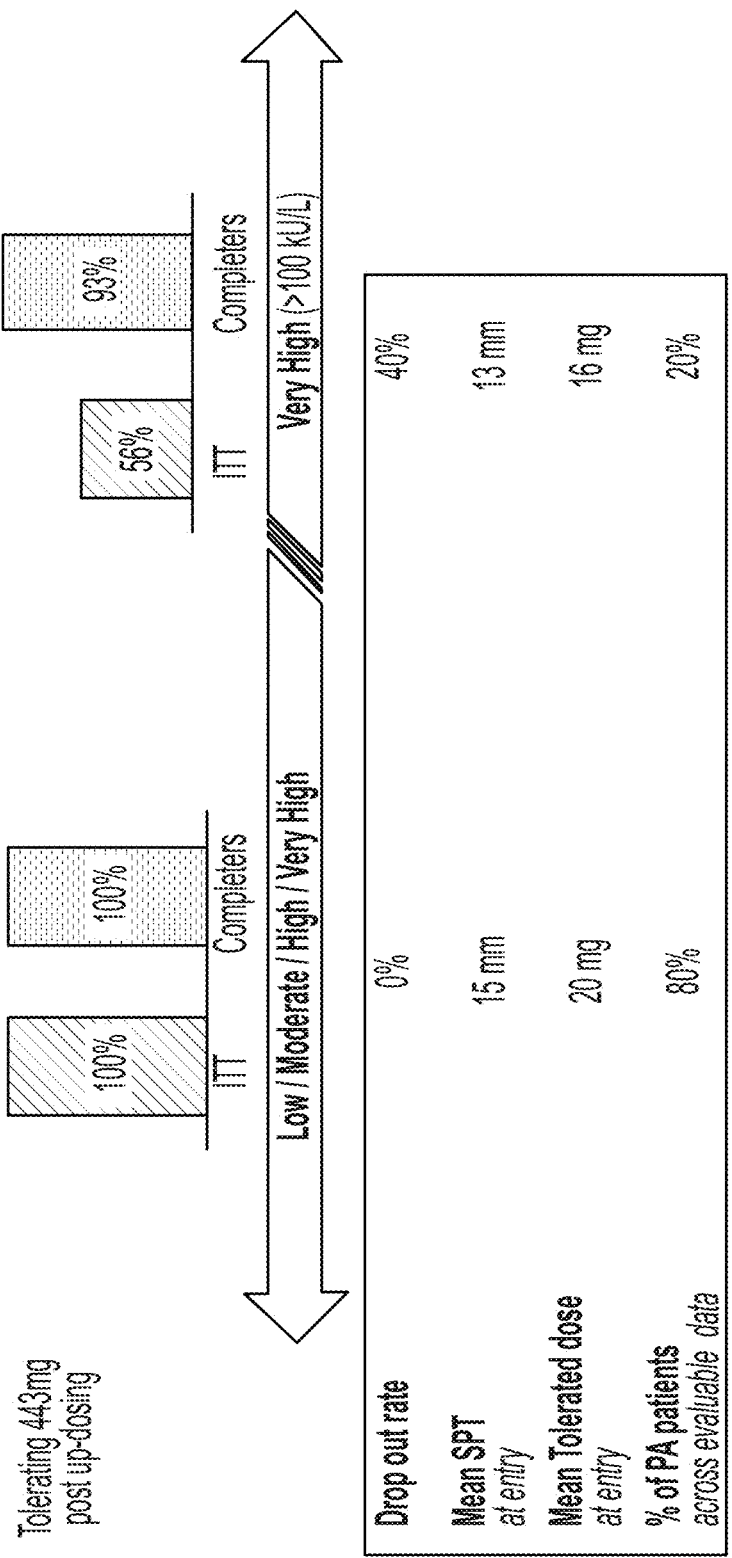
FIG. 1A shows a post-hoc patient cohort preliminary analysis from a phase 2 clinical trial of an oral immunotherapy (OIT) for the treatment of a peanut allergy.

The invention disclosed herein provides in various embodiments improved methods for treating a subject suffering from an allergy such as a food allergy. The inventors have found that patients suffering from an allergy such as a food allergy can be divided into sub-populations or sub-groups of patients as likely or unlikely to respond favorably to oral immunotherapy (OIT) with escalating doses of the food allergen based on the levels of one or more biomarkers. The patients can then be treated with OIT alone if they are likely to respond favorably to the oral administration of escalating doses of the food allergen. The patients who are unlikely to respond favorably to the oral administration of escalating doses of the food allergen can be treated with OIT in a modified manner to as to improve the likelihood of successfully completing OIT. For example, such a method can comprise administering the allergen in an OIT therapy in combination with another therapeutic agent such as an antagonist of one or more immunologic mediators of allergy, so as to improve their likelihood of responding favorably to OIT.

For instance, the inventors have found that subjects suffering from a peanut allergy can be divided at least into two groups: i) subjects likely to respond favorably to oral administration of escalating doses of peanut allergens and ii) subjects substantially less likely to respond favorably to oral administration of escalating doses of peanut allergens.

It has been found that the level of peanut-specific IgEs in a subject can indicate whether the subject is a good candidate for low-risk treatment of a peanut allergy. Patients with a level of peanut-specific IgEs at or below a predetermined threshold (such as about 100 kU/L) can be considered low-risk for an adverse reaction (such as anaphylaxis or eosinophilic esophagitis (EoE)) caused by the treatment. In some embodiments, subjects with a level of peanut-specific IgEs above the predetermined threshold are still administered treatment for the peanut allergy, although in such circumstances it is generally preferred that the subject undergoes heightened monitoring for an allergic reaction or that up-dosing of the allergenic peanut composition be limited or dosing reduced, as further explained herein.

The level of peanut-specific IgEs can also be used to evaluate an adverse event in a subject during the course of treatment of a peanut allergy. The symptoms of an allergic reaction are often similar to more benign or otherwise unrelated symptoms. For example, certain gastrointestinal symptoms in a subject, such as vomiting or abdominal pain, may be caused by an allergic reaction to an allergenic composition administered to the patient, or may be caused by an unrelated viral infection. The level of peanut-specific IgEs in the subject can be used to help indicate the cause of the symptoms. For example, in some embodiments, if the subject has a level of peanut-specific IgEs above a predetermined threshold (such as about 100 kU/L), the likelihood that the symptom is due to an allergic reaction to the peanut allergy treatment is heightened compared to if the level of the peanut-specific IgEs in the subject is at or below the predetermined threshold. If the subject has a level of peanut specific IgEs at or below the predetermined threshold, the likelihood that the symptom is due to an allergic reaction to the peanut allergy treatment is lessened compared to if the level of the peanut-specific IgEs in the subject is above the predetermined threshold. If the symptoms are found to be due to the treatment for peanut allergy, adjustments to the treatment can be made or the treatment a can be terminated. Adjustments the treatment may include reducing a dose or maintaining a dose instead of raising a dose during an up-dosing phase of treatment.

In some embodiments, the level of peanut-specific IgEs in the subject is used to assess the suitability of a treatment for a peanut allergy in a subject, or for assessing the suitability of the subject for treatment of a peanut allergy by immunotherapy (for example, oral immunotherapy). The method of assessing the suitability of a treatment for a peanut allergy in a subject can include receiving a level of peanut specific IgEs in the subject; and assessing the suitability of the treatment, wherein the subject having a level of peanut-specific IgEs at or below a predetermined threshold indicates that the treatment is suitable for the subject. The method of assessing the suitability of a subject for the treatment of a peanut allergy can include receiving a level of peanut specific IgEs in the subject; and assessing the suitability of the subject for the treatment, wherein the subject having a level of peanut-specific IgEs at or below a predetermined threshold indicates that the subject is suitable for the treatment. Additionally, as further described herein, the risk or incidence of an adverse event in a subject receiving treatment for a peanut allergy can be reduced by receiving a level of peanut-specific IgEs in the subject; and reducing a dose, delaying a dose, or delaying an increase of a dose of an allergenic peanut composition if the level of peanut-specific IgEs is above a predetermined threshold.

The level of peanut-specific IgEs can also be used to evaluate a symptom in a subject during the course of treatment for a peanut allergy. For example, a method of evaluating a symptom in a subject during the course of treatment of a peanut allergy can include receiving a level of peanut-specific IgEs in the subject having an adverse event; and determining whether the symptom is related to the treatment, wherein a level of peanut-specific IgEs at or below a predetermined threshold indicates that the adverse event is not caused by the treatment.

As further described herein, the level of peanut-specific IgEs can be used to assess a likelihood of an allergic reaction that requires administration of epinephrine to a subject receiving treatment for a peanut allergy. For example, a method of assessing a likelihood of an allergic reaction that requires administration of epinephrine to a subject receiving treatment for a peanut allergy, wherein the treatment comprises administration of at least one dose of an allergenic peanut composition, can include receiving a level of peanut-specific IgEs in the subject; and assessing the likelihood of an allergic reaction that requires administration of epinephrine to the patient, wherein a level of peanut-specific IgEs at or below a predetermined threshold indicates a reduced likelihood of an allergic reaction that requires administration of epinephrine during treatment, and wherein a level of peanut-specific IgEs above the predetermined threshold indicates an increased likelihood of an allergic reaction that requires administration of epinephrine during treatment.

In certain embodiments, the invention provides methods of treating a subject suffering from a food allergy who is more likely to respond favorably to oral immunotherapy comprising identifying a subject who is more likely to respond favorably to oral immunotherapy and administering to the subject more likely to respond favorably, at least one dose of the food allergen to the subject according to a dosing schedule. In other embodiments, the invention provides methods of treating a subject suffering from a food allergy who is significantly less likely to respond favorably to oral immunotherapy alone, said method comprising identifying the subjects who are significantly less likely to respond favorably to oral immunotherapy, administering at least one dose of the food allergen to the subject according to a dosing schedule and concomitantly administering a second therapeutic agent, for example a therapeutic agent which can improve the response of the subject to oral immunotherapy. The invention further provides methods of diagnosing or identifying a subject suffering from food allergy as likely, unlikely, or substantially less likely to respond favorably to oral immunotherapy alone based on one or more biomarkers.

Receiving a level of IgEs (such as a level of peanut-specific IgEs) can include any method of obtaining the IgE level. For example, in some embodiments, the level of IgE is received from a clinical laboratory that measured the IgE level. In some embodiments, the level of IgE is received by measuring the IgE level.

The level of peanut-specific IgEs can be measured from a patient serum sample (i.e., to measure a serum level of peanut-specific IgEs) or from a patient plasma sample (i.e., to measure a plasma level of peanuts-specific IgEs). Whole blood can be drawn from the patient, and the serum or plasm can be isolated from the whole blood using known methods. The level of the IgEs, including the level of total IgE, the level of peanut-specific IgEs, or the level of antigen-specific IgEs can be measured, for example, using a quantitative immunoassay.

Quantitative immunoassays are known in the art, and can include, but are not limited to, an enzyme-linked immunosorbent assay (ELISA); an alkaline phosphatase immunoassay auto-analyzer, such as an IMMULITE® system (Siemens Healthcare Diagnostics, Erlangen, Germany); a radioallergosorbent test (RAST), or a fluoroenzyme immunoassay auto-analyzer, such as the ImmunoCAP® system (Thermo Fisher Scientific/Phadia, Uppsala, Sweden). A fluorescence enzyme immunoassay (FEIA) auto-analyzer (e.g., ImmunoCAP® system) is a preferred technique, although other techniques may be reliably used. For example, another technique may be used as the level of antibody (e.g., IgE or IgG4) determined by that technique may be normalized to a measurement by a fluorescence enzyme immunoassay auto-analyzer. That is, a level of antibody (e.g., IgE or IgG4) can be determined by a technique, and can correspond to a level as measured by a fluorescence enzyme immunoassay auto-analyzer. The level of the biomarker (e.g., level of peanut-specific IgE and/or peanut-specific IgG4) is preferably determined in vitro.

As used herein, the singular forms "a," "an," and "the" include the plural references unless the context clearly dictates otherwise.

Reference to "about" a value or parameter herein includes (and describes) variations that are directed to that value or parameter per se. For example, description referring to "about X" includes description of "X".

It is understood that aspects and variations of the invention described herein include "consisting" and/or "consisting essentially of" aspects and variations.

The term "receiving" a level or value is understood to encompass any method of obtaining the level or value, for example by measuring the level or value, or by receiving the level or value from another party or entity that measures the level or value.

When a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

The section headings used herein are for organization purposes only and are not to be construed as limiting the subject matter described. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

The disclosures of all publications, patents, and patent applications referred to herein are each hereby incorporated by reference in their entireties. To the extent that any reference incorporated by reference conflicts with the instant disclosure, the instant disclosure shall control.

The following provides an exemplary method of a quantitative immunoassay to determine the level of peanut-specific IgEs in a subject. Whole blood can be withdrawn from the subject, and plasma or serum can be isolated from the whole blood. Peanut allergens from a peanut protein extract can be bound to a solid phase, such as a cellulose derivative with a high allergen binding capacity while maintaining their native structure. The isolated plasma or serum from the subject is introduced to the solid phase, where subject IgE molecules specific for the immobilized peanut allergens are pulled out of solution. Non-specific IgE molecules are then washed away. Antibodies against IgE (for example, an anti-human IgE antibody) that includes a signal-emitting moiety is added to the solid phase and incubated to allow the anti-IgE antibodies to bind to the peanut-specific IgEs bound to the surface. Unbound anti-IgE antibody can be washed away. The remaining immobilized complex comprising the allergen, specific IgE, and labeled anti-IgE antibody is incubated with a signal-developing agent. After stopping the signal-developing reaction, the intensity of the signal of the eluate is measured. Signal, such as fluorescence generated from a fluorophore, is correlated with the IgE level. Serial dilution may be carried out on the subject plasma or serum before the assay to bring the IgE concentration into the linear range of detection for any given assay. The intensity of signal, e.g., fluorescence, may be correlated to peanut-specific IgE serum concentration by comparison with a known control. The level of peanut-specific IgEs may be reported, such as to the subject or a clinician, which receives the level of peanut-specific IgEs.

In one embodiment, subjects likely to respond favorably to oral administration of escalating doses of the peanut allergens have a peanut-specific serum IgE level of less than about 100 kU/L. In another embodiment, subjects likely to respond favorably to oral administration of escalating doses of the peanut allergens have a peanut-specific serum IgE level of about 0.35 kU/L to about 99 kU/L. In yet another embodiment, subjects likely to respond favorably to oral administration of escalating doses of the peanut allergens have a peanut-specific serum IgE level of about 0.35 kU/L to about 50 kU/L, about 0.35 kU/L to about 55 kU/L, about 0.35 kU/L to about 60 kU/L, about 0.35 kU/L to about 65 kU/L, about 0.35 kU/L to about 70 kU/L, about 0.35 kU/L to about 75 kU/L, about 0.35 kU/L to about 80 kU/L, about 0.35 kU/L to about 85 kU/L about 0.35 kU/L to about 90 kU/L about 0.35 kU/L to about 95 kU/L, about 0.35 kU/L to about 99 kU/L, or about 0.35 kU/L to about 100 kU/L, including values and ranges therebetween.

In yet another embodiment, subjects likely to respond favorably to the oral administration of escalating doses of the peanut allergens have a peanut-specific serum IgE level of about 0.35 kU/L to about 125 kU/L, about 0.35 kU/L to about 150 kU/L, about 0.35 kU/L, to about 175 kU/L, about 0.35 kU/L to about 200 kU/L, about 0.35 kU/L to about 225 kU/L, about 0.35 kU/L to about 250 kU/L, about 0.35 kU/L to about 275 kU/L, about 0.35 kU/L to about 300 kU/L, about 0.35 kU/L to about 325 kU/L, about 0.35 kU/L to about 350 kU/L, about 0.35 kU/L to about 375 kU/L, about 0.35 kU/L to about 400 kU/L, about 0.35 kU/L to about 425 kU/L, or about 0.35 kU/L to about 450 kU/L, including values and ranges therebetween. In still another embodiment, subjects likely to respond favorably to the oral administration of escalating doses of the peanut allergens have a peanut-specific serum IgE level of less than about 100 kU/L to about 125 kU/L, less than about 100 kU/L to about 150 kU/L, less than about 100 kU/L to about 175 kU/L, less than about 100 kU/L to about 200 kU/L, less than about 200 kU/L to about 250 kU/L, less than about 200 kU/L to about 300 kU/L, less than about 300 kU/L to about 350 kU/L, or less than about 300 kU/L to about 400 kU/L, including values and ranges therebetween.

In one embodiment, subjects unlikely to respond favorably to oral administration of escalating doses of the peanut allergens have a peanut-specific serum IgE level of about 100 kU/L or more. In another embodiment, subjects unlikely to respond favorably to oral administration of escalating doses of the peanut allergens have a peanut-specific serum IgE level of about 70 kU/L, about 75 kU/L, about 80 kU/L, about 85 kU/L, about 90 kU/L, about 95 kU/L, about 100 kU/L, about 125 kU/L, about 150 kU/L, about 175 kU/L, about 200 kU/L, about 225 kU/L, about 250 kU/L, about 275 kU/L, about 300 kU/L, about 325 kU/L, about 350 kU/L, about 375 kU/L about 400 kU/L, or more, including values and ranges therebetween.

According to one aspect of the invention, treating subjects likely to respond favorably to oral administration of escalating doses of the peanut allergens according to the methods of the invention would result in as success rate of at least about 80%, at least about 85%, at least about 90%, at least about 95% or about 100%, including values therebetween. That is, in one embodiment, at least about 80%, at least about 85%, at least about 90%, at least about 95% or about 100% of the subjects likely to respond favorably to the oral administration of escalating doses of the peanut allergens, when treated according to the methods of the invention would not develop one or more allergic reactions or symptoms after consuming peanuts.

The terms "patient" and "subject" are used interchangeably throughout this disclosure. In some embodiments, the subject is a human subject.

An action "based on" a factor is well-understood to refer to an action that results from taking into account the factor. The factor need not be an exclusive factor, or even a primary factor, for determining whether and/or how the action occurs. Accordingly, the phrase "action X based on factor Y" means that factor Y is taken into account when determining whether and/or how the action X should or would be performed (or conversely, not performed). The factor need not be an exclusive factor in determining whether or how action X should be performed, and may be, but need not be, a primary or secondary factor taken into account. Various types of actions are described herein, such as methods administering a dose comprising an allergenic composition to a subject and methods of identifying a subject suitable for the treatment of a peanut allergy. Various types of factors, such as a level of IgE in the subject, particularly in reference to a threshold, are also described.

The invention provides methods of treating a subject suffering from as food allergy, comprising orally administering at least one dose of at least one allergen to the subject according to a dosing schedule, wherein the subject is likely to respond favorably to the oral administration of the food allergen.

In various embodiments, the subject likely to respond favorably to the oral administration of the food allergen has the food allergen-specific serum IgE levels of about 0.35 kU/L to about 0.69 kU/L, about 0.70 kU/L to about 3.49 kU/L, about 3.50 kU/L to about 17.4 kU/L, about 17.5 kU/L to about 49.9 kU/L, about 50 kU/L to about 99.9 kU/L, about 0.35 kU/L to about 17.4 kU/L, about 0.35 kU/L to about 20 kU/L, about 0.35 kU/L to about 25 kU/L, about 0.35 kU/L to about 30 kU/L, about 0.35 kU/L to about 35 kU/L, about 0.35 kU/L to about 40 kU/L, about 0.35 kU/L to about 45 kU/L, about 0.35 kU/L to about 50 kU/L, about 0.35 kU/L to about 55 kU/L, about 0.35 kU/L to about 60 kU/L, about 0.35 kU/L to about 65 kU/L, about 0.35 kU/L to about 70 kU/L, about 0.35 kU/L to about 75 kU/L, about 0.35 kU/L to about 80 kU/L, about 0.35 kU/L to about 85 kU/L, about 0.35 kU/L to about 90 kU/L, about 0.35 kU/L to about 95 kU/L, or about 0.35 kU/L to about 99 kU/L, including values and ranges therebetween.

In yet another embodiment, subjects likely to respond favorably to the oral administration of escalating doses of the food allergen have a food allergen-specific serum IgE level of about 0.35 kU/L to about 125 kU/L, about 0.35 kU/L to about 150 kU/L, about 0.35 kU/L to about 175 kU/L, about 0.35 kU/L to about 200 kU/L, about 0.35 kU/L to about 225 kU/L, about 0.35 kU/L to about 250 kU/L, about 0.35 kU/L to about 275 kU/L, about 0.35 kU/L to about 300 kU/L, about 0.35 kU/L to about 325 kU/L, about 0.35 kU/L to about 350 kU/L, about 0.35 kU/L to about 375 kU/L, about 0.35 kU/L to about 400 kU/L, about 0.35 kU/L to about 425 kU/L, or about 0.35 kU/L to about 450 kU/L, including values and ranges therebetween.

In still another embodiment, subjects likely to respond favorably to the oral administration of escalating doses of the food allergen have a food allergen-specific serum IgE level of less than about 100 kU/L to about 125 kU/L, less than about 100 kU/L to about 150 kU/L, less than about 100 kU/L to about 175 kU/L, less than about 100 kU/L to about 200 kU/L, less than about 200 kU/L to about 250 kU/L, less than about 200 kU/L to about 300 kU/L, less than about 300 kU/L to about 350 kU/L, or less than about 300 kU/L to about 400 kU/L, including values and ranges therebetween.

The invention provides methods of treating a subject suffering from a food allergy, comprising orally administering at least one dose of at least one allergen to the subject according to a dosing schedule, and concomitantly administering another therapeutic agent; wherein the subject is unlikely to respond favorably to the oral administration of the food allergen.

In one embodiment, the subject unlikely to respond favorably to the oral administration of the food allergen has the food allergen-specific serum IgE levels of about 17 kU/L or more. In various other embodiments, the subject unlikely to respond favorably to the oral administration of the food allergen has the food allergen-specific serum IgE levels of about 50 kU/L or more, about 55 kU/L or more, about 60 kU/L or more, about 65 kU/L or more, about 70 kU/L or more, about 75 kU/L or more, about 80 kU/L or more, about 85 kU/L or more, about 90 kU/L or more, about 95 kU/L or more, about 100 kU/L or more, about 125 kU/L or more, about 150 kU/L or more, about 175 kU/L or more, about 200 kU/L or more, about 225 kU/L or more, about 250 kU/L or more, about 275 kU/L or more, about 300 kU/L or more, about 325 kU/L or more, about 350 kU/L or more, about 375 kU/L or more, or about 400 kU/L or more, including values and ranges therebetween.

According to certain aspects of the invention, patients suffering from a food allergy can be classified as likely or unlikely to respond favorably to OIT with escalating doses of the food allergen based on the levels of one or more biomarkers. The biomarkers that could be used to distinguish the patient population as likely or unlikely to respond favorably to OIT include, but are not limited to, total IgE, food allergen-specific IgEs, food allergen-specific IgG4, cell surface markers on immune cells (e.g. lymphocytes, monocytes, basophils, eosinophils), ratio of IgG/IgE, ratio of food allergen-specific IgE/IgG4, age, and gender.

For instance, patients suffering from a peanut allergy can be classified as likely or unlikely to respond favorably to OIT with escalating doses of peanut allergens based on the levels of one or more biomarkers including, but not limited to, total IgE, peanut-specific IgEs, peanut-specific IgG4, component-resolved peanut IgE (e.g., Ara h1-specific IgE, Ara h2-specific IgE, Ara h3-specific IgE, Ara h8-specific IgE, Ara h9-specific IgE), cell surface markers on immune cells (e.g. lymphocytes, monocytes, basophils, eosinophils), ratio of IgG/IgE, ratio of peanut-specific total IgE/IgG4, ratio of individual peanut component-specific IgE/IgG4, age, and gender.

According to one aspect, a subject suffering from a food allergy who is unlikely to respond favorably to the oral administration of the food allergen is treated by orally administering at least one dose of at least one allergen to the subject according to a dosing schedule, and concomitantly administering another therapeutic agent. In one embodiment, the other therapeutic agent is an antagonist of one or more immunological mediators of allergy.

For instance, the other therapeutic agent could be, but is not limited to, an IgE antagonist such as Omalizumab (Xolair), IL-4 antagonist, IL-5 antagonist, IL-13 antagonist, IL-33 antagonist and combinations thereof. Exemplary IgE antagonists include ligelizumab (Phase 2). Exemplary IL-5 antagonists include Cinquil/reslizumab (approved), Nucala/mepolizumab (approved), and benralizumab (Phase 3). Exemplary IL-4/IL-13 antagonists include dupilumab (Phase 3) and SAR156597 (Phase 2). Exemplary IL-13 antagonists include lebrikizumab (Phase 3) and tralokinumab (Phase 3). Exemplary IL-33 antagonists include AMG 282 (Phase 1) and ANB020 (Phase 1).

The other therapeutic agent can be administered concomitantly, but in separate formulations, or sequentially. In some embodiments, concomitant administration includes prior administration, for instance, administration of the other therapeutic agent within the range of about 60 minutes, 50 minutes, 40 minutes, 30 minutes, 20 minutes, 10 minutes, or 5 minutes prior to administration of the allergen. In certain embodiments, concomitant administration includes prior administration, for instance, administration of the other therapeutic agent about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, and/or about 16 weeks, including ranges therebetween, prior to administration of the allergen. In other embodiments, concomitant administration includes prior administration, for instance, administration of the other therapeutic agent about one week, about two weeks, about one month, about two months, about 3 months, and/or about four months, including ranges therebetween, prior to administration of the allergen.

The invention further provides methods of diagnosing a subject suffering from a food allergy as likely or unlikely to respond favorably to the oral administration of the food allergen based on the levels of one or more biomarkers in the subject.

For instance, the invention provides a method of diagnosing a subject suffering from a food allergy as likely or unlikely to respond favorably to the oral administration of peanut allergens comprising measuring the level of peanut-specific serum IgE in the subject and diagnosing the subject as likely to respond favorably to the oral administration of peanut allergens if the subject as the peanut-specific serum IgE level below a particular threshold or diagnosing the subject as unlikely to respond favorably to the oral administration of peanut allergens if the subject has the peanut-specific serum IgE level above a particular threshold.

In one embodiment, a subject having a peanut allergy is diagnosed as likely to respond favorably to the oral administration of peanut allergens if the subject has the peanut-specific serum IgE level of about 0.35 kU/L to about 17.4 kU/L, about 0.35 kU/L to about 20 kU/L, about 0.35 kU/L to about 25 kU/L, about 0.35 kU/L to about 30 kU/L, about 0.35 kU/L to about 35 kU/L, about 0.35 kU/L to about to about 40 kU/L, about 0.35 kU/L to about 45 kU/L, about 0.35 kU/L to about 50 kU/L, about 0.35 kU/L, to about 55 kU/L, about 0.35 kU/L to about 60 kU/L, about 0.35 kU/L to about 65 kU/L, about 0.35 KU/L to about 70 kU/L, about 0.35 kU/L to about 75 kU/L, about 0.35 kU/L to about 80 kU/L, about 0.35 kU/L to about 85 kU/L, about 0.35 kU/L to about 90 kU/L, about 0.35 kU/L to about 95 kU/L, about 0.35 kU/L to about 99 kU/L, about 0.35 kU/L to about 100 kU/L, including values and ranges therebetween.

In yet another embodiment, a subject having a peanut allergy is diagnosed as likely to respond favorably to the oral administration of peanut allergens if the subject has the peanut-specific serum IgE level of about 0.35 kU/L to about 125 kU/L, about 0.35 kU/L to about 150 kU/L, about 0.35 kU/L to about 175 kU/L, about 0.35 kU/L to about 200 kU/L, about 0.35 kU/L to about 225 kU/L, about 0.35 kU/L to about 250 kU/L, about 0.35 kU/L to about 275 kU/L, about 0.35 kU/L to about 300 kU/L, about 0.35 kU/L to about 325 kU/L, about 0.35 kU/L to about 350 kU/L, about 0.35 kU/L to about 375 kU/L, about 0.35 kU/L to about 400 kU/L, about 0.35 kU/L to about 425 kU/L, or about 0.35 kU/L to about 450 kU/L, including values and ranges therebetween. In still another embodiment, a subject having a peanut allergy is diagnosed as likely to respond favorably to the oral administration of peanut allergens if the subject has the peanut-specific serum IgE level of less than about 100 kU/L to about 125 kU/L, less than about 100 kU/L to about 150 kU/L, less than about 100 kU/L to about 175 kU/L, less than about 100 kU/L to about 200 kU/L, less than about 200 kU/L to about 250 kU/L, less than about 200 kU/L to about 300 kU/L, less than about 300 kU/L to about 350 kU/L, or less than about 300 kU/L to about 400 kU/L, including values and ranges therebetween.

In one embodiment, a subject having a peanut allergy is diagnosed as unlikely to respond favorably to the oral administration of peanut allergens if the subject has the peanut-specific serum IgE level of about 50 kU/L or more, about 55 kU/L or more, about 60 kU/L or more, about 65 kU/L or more, about 70 kU/L or more, about 75 kU/L or more, about 80 kU/L or more, about 85 kU/L or more, about 90 kU/L or more, about 95 kU/L or more, about 100 kU/L or more, about 125 kU/L or more, about 150 kU/L or more, about 175 kU/L or more, about 200 kU/L or more, about 225 kU/L or more, about 250 kU/L or more, about 275 kU/L or more, about 300 kU/L or more, about 325 kU/L or more, about 350 kU/L or more, about 375 kU/L or more, or about 400 kU/L or more, including values and ranges therebetween.

In some embodiments, the subject being treated is suffering from a peanut allergy and at least one dose of an allergen composition comprising peanut flour is administered to the subject orally.

Allergen compositions administered as OIT may comprise a food source comprising one or one or more characterized allergen proteins and pharmaceutically acceptable excipients. For instance, in one embodiment, the allergen composition comprises one or more characterized peanut proteins and pharmaceutically acceptable excipients. In some embodiments, the amount of peanut proteins in the allergen composition ranges from about 0.05% to about 100% w/w.

Allergen compositions for treating peanut allergy may comprise characterized peanut proteins selected from the group consisting of characterized Ara h1 proteins, characterized Ara h2 proteins, characterized Ara h6 proteins, and combinations thereof.

In some embodiments, allergen compositions for treating peanut allergy comprise one or more characterized Ara h1 proteins in an amount of from about 0.035 to about 65 mg. In some other embodiments, allergen compositions comprise one or more characterized Ara h2 proteins in an amount of from about 0.035 to about 60 mg. In yet some other embodiments, allergen compositions comprise one or more characterized Ara h6 proteins in an amount of from about 0.015 to about 40 mg.

Methods of Identifying a Subject Suitable for Treatment

In some embodiments, a subject with a peanut allergy is identified as suitable for treatment or selected for treatment of a peanut allergy based on having a level of peanut-specific IgEs at or below a predetermined threshold (such as about 100 kU/L). Further, a subject with a peanut allergy can be identified as not suitable for treatment or not selected for treatment of a peanut allergy based on having a level of peanut-specific IgEs above the predetermined threshold. In some embodiments, the level of peanut-specific IgEs is a primary factor in determining whether a subject is identified as suitable for treatment or selected for treatment of the peanut allergy. In some embodiments, the level of peanut-specific IgEs is an exclusive factor in determining whether the subject is identified as suitable for treatment or selected for treatment of the peanut allergy. In some embodiments, the subject with a peanut allergy is identified as suitable for treatment or selected for treatment only if the subject has a level of peanut-specific IgEs at or below a predetermined threshold (such as about 100 kU/L). For example, in some embodiments, the subject with a peanut allergy is identified as suitable for treatment of the peanut allergy only if the subject has a level of peanut-specific IgEs at or below the predetermined threshold (such as about 100 kU/L). In some embodiments, the subject with a peanut allergy is selected for treatment of the peanut allergy only if the subject has a level of peanut-specific IgE at or below the predetermined threshold (such as about 100 kU/L). In some embodiments, the treatment is an oral immunotherapy dosing regimen. In some embodiments, the method further comprises receiving the level of peanut-specific IgEs, or measuring the level of peanut-specific IgEs.

In some embodiments, the level of peanut-specific IgEs is a level in the subject prior to initiation of the treatment. In some embodiments, the level of peanut-specific IgEs is determined in the subject at a time proximal to the selection or identification of the subject for treatment, for example within about 7 days, within about 5 days, within about 72 hours, within about 48 hours, within about 24 hours, within about 12 hours, within about 6 hours, within about 4 hours, within about 3 hours, within about 2 hours, or within about 1 hour of selecting the subject for treatment or identifying the subject as suitable for treatment. In some embodiments, the method includes receiving or measuring a level of peanut-specific IgEs in a subject prior to initiation of the treatment, and selecting the subject for treatment based on having a level of peanut-specific IgEs at or below a predetermined threshold (such as about 100 kU/L).

In some embodiments, there is a method of identifying a subject with a peanut allergy suitable for treatment of the peanut allergy, comprising evaluating a level of peanut-specific IgEs in the subject, wherein the subject is identified as suitable for treatment based on having a level of peanut-specific IgEs at or below a predetermined threshold (such as about 100 kU/L). In some embodiments, the level of peanut-specific IgEs is a primary factor in determining whether a subject is identified as suitable for treatment of the peanut allergy. In some embodiments, the level of peanut-specific IgEs is an exclusive factor in determining whether the subject is identified as suitable for treatment of the peanut allergy. In some embodiments, the subject with a peanut allergy is identified as suitable for treatment only if the subject has a level of peanut-specific IgEs at or below the predetermined threshold (such as about 100 kU/L). In some embodiments, the level of peanut-specific IgEs is a level in the subject prior to initiation of the treatment. In some embodiments, the level of peanut-specific IgEs is determined in the subject at a time proximal to the identifying the subject for treatment.

In some embodiments, there is a method of selecting a subject with a peanut allergy for treatment of the peanut allergy, comprising evaluating a level of peanut-specific IgEs in the subject, wherein the subject is selected for treatment based on having a level of peanut-specific IgEs at or below a predetermined threshold. In some embodiments, the level of peanut-specific IgEs is a primary factor in determining whether a subject is selected for treatment of the peanut allergy. In some embodiments, the level of peanut-specific IgEs is an exclusive factor in determining whether the subject is selected for treatment of the peanut allergy. In some embodiments, the subject with a peanut allergy is selected for treatment only if the subject has a level of peanut-specific IgEs at or below the predetermined threshold (such as about 100 kU/L). In some embodiments, the level of peanut-specific IgEs is a level in the subject prior to initiation of the treatment. In some embodiments, the level of peanut-specific IgEs is determined in the subject at a time proximal to the identifying the subject for treatment.

In some embodiments, there is a method of identifying a subject with a peanut allergy suitable for treatment of the peanut allergy using an oral immunotherapy dosage regimen, comprising evaluating a level of peanut-specific IgEs in the subject, wherein the subject is identified as suitable for treatment using the oral immunotherapy dosing regimen based on having a level of peanut-specific IgEs at or below a predetermined threshold (such as about 100 kU/L). In some embodiments, the level of peanut-specific IgEs is a primary factor in determining whether a subject is identified as suitable for treatment of the peanut allergy. In some embodiments, the level of peanut-specific IgEs is an exclusive factor in determining whether the subject is identified as suitable for treatment of the peanut allergy. In some embodiments, the subject with a peanut allergy is identified as suitable for treatment only if the subject has a level of peanut-specific IgEs at or below the predetermined threshold (such as about 100 kU/L). In some embodiments, the level of peanut-specific IgEs is a level in the subject prior to initiation of the treatment. In some embodiments, the level of peanut-specific IgEs is determined in the subject at a time proximal to the identifying the subject for treatment.

In some embodiments, there is a method of selecting a subject with a peanut allergy for treatment of the peanut allergy using an oral immunotherapy dosage regimen, comprising evaluating a level of peanut-specific IgEs in the subject, wherein the subject is selected for treatment using the oral immunotherapy dosing regimen based on having a level of peanut-specific IgEs at or below a predetermined threshold (such as about 100 kU/L). In some embodiments, the level of peanut-specific IgEs is a primary factor in determining whether a subject is selected for treatment of the peanut allergy. In some embodiments, the level of peanut-specific IgEs is an exclusive factor in determining whether the subject is selected for treatment of the peanut allergy. In some embodiments, the subject with a peanut allergy is selected for treatment only if the subject has a level of peanut-specific IgEs at or below the predetermined threshold (such as about 100 kU/L). In some embodiments, the level of peanut-specific IgEs is a level in the subject prior to initiation of the treatment. In some embodiments, the level of peanut-specific IgEs is determined in the subject at a time proximal to the identifying the subject for treatment.

In some embodiments, there is a method of identifying a subject with a peanut allergy suitable for treatment of the peanut allergy, comprising: receiving a level of peanut-specific IgEs in the subject; and identifying the subject as suitable for treatment based on having a level of peanut-specific IgEs at or below a predetermined threshold (such as about 100 kU/L). In some embodiments, the level of peanut-specific IgEs is a primary factor in determining whether a subject is identified as suitable for treatment of the peanut allergy. In some embodiments, the level of peanut-specific IgEs is an exclusive factor in determining whether the subject is identified as suitable for treatment of the peanut allergy. In some embodiments, the subject with a peanut allergy is identified as suitable for treatment only if the subject has a level of peanut-specific IgEs at or below the predetermined threshold (such as about 100 kU/L). In some embodiments, the level of peanut-specific IgEs is a level in the subject prior to initiation of the treatment. In some embodiments, the level of peanut-specific IgEs is determined in the subject at a time proximal to the identifying the subject for treatment.

In some embodiments, there is a method of selecting a subject with a peanut allergy for treatment of the peanut allergy, comprising: receiving a level of peanut-specific IgEs in the subject; and selecting the subject for treatment based on having a level of peanut-specific IgEs at or below a predetermined threshold (such as about 100 kU/L). In some embodiments, the level of peanut-specific IgEs is a primary factor in determining whether a subject is selected for treatment of the peanut allergy. In some embodiments, the level of peanut-specific IgEs is an exclusive factor in determining whether the subject is selected for treatment of the peanut allergy. In some embodiments, the subject with a peanut allergy is selected for treatment only if the subject has a level of peanut-specific IgEs at or below the predetermined threshold (such as about 100 kU/L). In some embodiments, the level of peanut-specific IgEs is a level in the subject prior to initiation of the treatment. In some embodiments, the level of peanut-specific IgEs is determined in the subject at a time proximal to the identifying the subject for treatment.

In some embodiments, there is a method of identifying a subject with a peanut allergy as suitable for treatment of the peanut allergy using an oral immunotherapy dosage regimen, comprising: receiving a level of peanut-specific IgEs in the subject; and identifying the subject as suitable for treatment using the oral immunotherapy dosage regimen based on having a level of peanut-specific IgEs at or below a predetermined threshold (such as about 100 kU/L). In some embodiments, the level of peanut-specific IgEs is a primary factor in determining whether a subject is identified as suitable for treatment of the peanut allergy. In some embodiments, the level of peanut-specific IgEs is an exclusive factor in determining whether the subject is identified as suitable for treatment of the peanut allergy. In some embodiments, the subject with a peanut allergy is identified as suitable for treatment only if the subject has a level of peanut-specific IgEs at or below the predetermined threshold (such as about 100 kU/L). In some embodiments, the level of peanut-specific IgEs is a level in the subject prior to initiation of the treatment. In some embodiments, the level of peanut-specific IgEs is determined in the subject at a time proximal to the identifying the subject for treatment.

In some embodiments, there is a method of selecting a subject with a peanut allergy for treatment of the peanut allergy using an oral immunotherapy dosage regimen, comprising: receiving a level of peanut-specific IgEs in the subject; and selecting the subject for treatment using the oral immunotherapy dosage regimen based on having a level of peanut-specific IgEs at or below a predetermined threshold (such as about 100 kU/L). In some embodiments, the level of peanut-specific IgEs is a primary factor in determining whether a subject is selected for treatment of the peanut allergy. In some embodiments, the level of peanut-specific IgEs is an exclusive factor in determining whether the subject is selected for treatment of the peanut allergy. In some embodiments, the subject with a peanut allergy is selected for treatment only if the subject has a level of peanut-specific IgEs at or below the predetermined threshold (such as about 100 kU/L). In some embodiments, the level of peanut-specific IgEs is a level in the subject prior to initiation of the treatment. In some embodiments, the level of peanut-specific IgEs is determined in the subject at a time proximal to the identifying the subject for treatment.

In some embodiments, there is a method of identifying a subject with a peanut allergy suitable for treatment of the peanut allergy, comprising: measuring a level of peanut-specific IgEs in the subject; and identifying the subject as suitable for treatment based on having a level of peanut-specific IgEs at or below a predetermined threshold (such as about 100 kU/L). In some embodiments, the level of peanut-specific IgEs is a primary factor in determining whether a subject is identified as suitable for treatment of the peanut allergy. In some embodiments, the level of peanut-specific IgEs is an exclusive factor in determining whether the subject is identified as suitable for treatment of the peanut allergy. In some embodiments, the subject with a peanut allergy is identified as suitable for treatment only if the subject has a level of peanut-specific IgEs at or below the predetermined threshold (such as about 100 kU/L). In some embodiments, the level of peanut-specific IgEs is a level in the subject prior to initiation of the treatment. In some embodiments, the level of peanut-specific IgEs is determined in the subject at a time proximal to the identifying the subject for treatment.

In some embodiments, there is a method of selecting a subject with a peanut allergy for treatment of the peanut allergy, comprising: measuring a level of peanut-specific IgEs in the subject; and selecting the subject for treatment based on having a level of peanut-specific IgEs at or below a predetermined threshold (such as about 100 kU/L). In some embodiments, the level of peanut-specific IgEs is a primary factor in determining whether a subject is selected for treatment of the peanut allergy. In some embodiments, the level of peanut-specific IgEs is an exclusive factor in determining whether the subject is selected for treatment of the peanut allergy. In some embodiments, the subject with a peanut allergy is selected for treatment only if the subject has a level of peanut-specific IgEs at or below the predetermined threshold (such as about 100 kU/L). In some embodiments, the level of peanut-specific IgEs is a level in the subject prior to initiation of the treatment. In some embodiments, the level of peanut-specific IgEs is determined in the subject at a time proximal to the identifying the subject for treatment.

In some embodiments, there is a method of identifying a subject with a peanut allergy as suitable for treatment of the peanut allergy using an oral immunotherapy dosage regimen, comprising: measuring a level of peanut-specific IgEs in the subject; and identifying the subject as suitable for treatment using the oral immunotherapy dosage regimen based on having a level of peanut-specific IgEs at or below a predetermined threshold (such as about 100 kU/L). In some embodiments, the level of peanut-specific IgEs is a primary factor in determining whether a subject is identified as suitable for treatment of the peanut allergy. In some embodiments, the level of peanut-specific IgEs is an exclusive factor in determining whether the subject is identified as suitable for treatment of the peanut allergy. In some embodiments, the subject with a peanut allergy is identified as suitable for treatment only if the subject has a level of peanut-specific IgEs at or below the predetermined threshold (such as about 100 kU/L). In some embodiments, the level of peanut-specific IgEs is a level in the subject prior to initiation of the treatment. In some embodiments, the level of peanut-specific IgEs is determined in the subject at a time proximal to the identifying the subject for treatment.

In some embodiments, there is a method of selecting a subject with a peanut allergy for treatment of the peanut allergy using an oral immunotherapy dosage regimen, comprising: measuring a level of peanut-specific IgEs in the subject; and selecting the subject for treatment using the oral immunotherapy dosage regimen based on having a level of peanut-specific IgEs at or below a predetermined threshold (such as about 100 kU/L). In some embodiments, the level of peanut-specific IgEs is a primary factor in determining whether a subject is selected for treatment of the peanut allergy. In some embodiments, the level of peanut-specific IgEs is an exclusive factor in determining whether the subject is selected for treatment of the peanut allergy. In some embodiments, the subject with a peanut allergy is selected for treatment only if the subject has a level of peanut-specific IgEs at or below the predetermined threshold (such as about 100 kU/L). In some embodiments, the level of peanut-specific IgEs is a level in the subject prior to initiation of the treatment. In some embodiments, the level of peanut-specific IgEs is determined in the subject at a time proximal to the identifying the subject for treatment.

Methods of Assessing Suitability of a Treatment for a Subject

The suitability of a treatment for a peanut allergy for a subject with a peanut allergy can be assessed in view of the level of peanut-specific IgEs in a subject. The level of peanut-specific IgE in the patient need not be an exclusive factor in the suitability of treatment, but can be a factor taken into consideration when assessing the suitability of the treatment for the subject. In some embodiments, a level of peanut-specific IgEs in the subject at or below a predetermined threshold (such as about 100 kU/L) indicates that the treatment is suitable for the subject. In some embodiments, the treatment is suitable for the subject only if the level of peanut-specific IgEs in the subject is at or below the predetermined threshold. In some embodiments, a method of assessing the suitability of a treatment comprises receiving the level of peanut-specific IgEs, or measuring the level of peanut-specific IgEs. In some embodiments, a level of peanut-specific IgEs in the subject above a predetermined threshold (such as about 100 kU/L) indicates that the treatment is not suitable for the subject.

In some embodiments, the level of peanut-specific IgEs is a level in the subject prior to initiation of the treatment or prior to the assessment of the suitability of the treatment for the subject. In some embodiments, the level of peanut-specific IgEs is determined in the subject at a time proximal to the assessment of the treatment for the subject, for example within about 7 days, within about 5 days, within about 72 hours, within about 48 hours, within about 24 hours, within about 12 hours, within about 6 hours, within about 4 hours, within about 3 hours, within about 2 hours, or within about 1 hour prior to assessing the suitability of the treatment for the subject. In some embodiments, the method includes receiving or measuring a level of peanut-specific IgEs in a subject prior to assessing suitability of the treatment for the subject.

In some embodiments, the treatment is an oral immunotherapy dosing regimen. In some embodiments, the treatment is a phase (or sub-phase) of an oral immunotherapy dosing regimen, or other treatment. As further explained herein, in some embodiments, a treatment regimen can include one or more phases, such as an initial escalation phase (which may comprise one or more sub-phase), an up-dosing phase (which may comprise one or more sub-phases), and/or a maintenance phase. In some embodiments, the suitability of the next phase or sub-phase of the treatment regimen can be determined based on the level of peanut-specific IgEs in the subject. In some embodiments, the level of peanut-specific IgEs is received or measured following or prior to one or more phases or sub-phases of the treatment regimen.

In some embodiments, a method of assessing the suitability of a treatment for a peanut allergy in a subject with a peanut allergy comprises: receiving a level of peanut-specific IgEs in the subject; and assessing the suitability of the treatment, wherein the subject having a level of peanut specific IgEs at or below a predetermined threshold (such as about 100 kU/L) indicates that the treatment is suitable for the subject. In some embodiments, the treatment is suitable for the subject if the level of peanut-specific IgE is at or below the predetermined threshold. In some embodiments, the treatment is a phase (such as an initial escalation phase, an up-dosing phase, or a maintenance phase) or a sub-phase (such as a dosage increase during an initial escalation phase or a dosage increase during an up-dosing phase) of a treatment regimen. In some embodiments, the level of peanut-specific IgEs is determined at a time proximal to assessing the suitability of the treatment for the subject.

In some embodiments, a method of assessing the suitability of an oral immunotherapy dosing regimen for a peanut allergy in a subject with a peanut allergy comprises: receiving a level of peanut-specific IgEs in the subject; and assessing the suitability of the oral immunotherapy dosing regimen, wherein the subject having a level of peanut specific IgEs at or below a predetermined threshold (such as about 100 kU/L) indicates that the oral immunotherapy dosing regimen is suitable for the subject. In some embodiments, the treatment is suitable for the subject if the level of peanut-specific IgE is at or below the predetermined threshold. In some embodiments, the level of peanut-specific IgEs is determined at a time proximal to assessing the suitability of the treatment for the subject.

In some embodiments, a method of assessing the suitability of a phase (such as an initial escalation phase, an up-dosing phase, or a maintenance phase) or sub-phase (such as a dosage increase during an initial escalation phase or a dosage increase during an up-dosing phase) of an oral immunotherapy dosing regimen for treatment of a peanut allergy in a subject with a peanut allergy comprises: receiving a level of peanut-specific IgEs in the subject prior to the phase or sub-phase; and assessing the suitability of the phase or sub-phase of the oral immunotherapy dosing regimen, wherein the subject having a level of peanut specific IgEs at or below a predetermined threshold (such as about 100 kU/L) indicates that the phase or sub-phase is suitable for the subject. In some embodiments, the phase or sub-phase is suitable for the subject if the level of peanut-specific IgE is at or below the predetermined threshold. In some embodiments, the level of peanut-specific IgEs is determined at a time proximal to assessing the suitability of the phase or sub-phase for the subject. In some embodiments, the level of peanut-specific IgEs is determined at a time proximal to the start of the oral immunotherapy dosing regimen.

In some embodiments, a method of assessing the suitability of a treatment for a peanut allergy in a subject with a peanut allergy comprises: measuring a level of peanut-specific IgEs in the subject; and assessing the suitability of the treatment, wherein the subject having a level of peanut specific IgEs at or below a predetermined threshold (such as about 100 kU/L) indicates that the treatment is suitable for the subject. In some embodiments, the treatment is suitable for the subject if the level of peanut-specific IgE is at or below the predetermined threshold. In some embodiments, the treatment is a phase (such as an initial escalation phase, an up-dosing phase, or a maintenance phase) or a sub-phase (such as a dosage increase during an initial escalation phase or a dosage increase during an up-dosing phase) of a treatment regimen. In some embodiments, the level of peanut-specific IgEs is determined at a time proximal to assessing the suitability of the treatment for the subject.

In some embodiments, a method of assessing the suitability of an oral immunotherapy dosing regimen for a peanut allergy in a subject with a peanut allergy comprises: measuring a level of peanut-specific IgEs in the subject; and assessing the suitability of the oral immunotherapy dosing regimen, wherein the subject having a level of peanut specific IgEs at or below a predetermined threshold (such as about 100 kU/L) indicates that the oral immunotherapy dosing regimen is suitable for the subject. In some embodiments, the treatment is suitable for the subject if the level of peanut-specific IgE is at or below the predetermined threshold. In some embodiments, the level of peanut-specific IgEs is determined at a time proximal to assessing the suitability of the treatment for the subject.

In some embodiments, a method of assessing the suitability of a phase (such as an initial escalation phase, an up-dosing phase, or a maintenance phase) or sub-phase (such as a dosage increase during an initial escalation phase or a dosage increase during an up-dosing phase) of an oral immunotherapy dosing regimen for treatment of a peanut allergy in a subject with a peanut allergy comprises: measuring a level of peanut-specific IgEs in the subject prior to the phase or sub-phase; and assessing the suitability of the phase or sub-phase of the oral immunotherapy dosing regimen, wherein the subject having a level of peanut specific IgEs at or below a predetermined threshold (such as about 100 kU/L) indicates that the phase or sub-phase is suitable for the subject. In some embodiments, the phase or sub-phase is suitable for the subject if the level of peanut-specific IgE is at or below the predetermined threshold. In some embodiments, the level of peanut-specific IgEs is determined at a time proximal to assessing the suitability of the phase or sub-phase for the subject. In some embodiments, the level of peanut-specific IgEs is determined at a time proximal to the start of the oral immunotherapy dosing regimen.

Methods of Treatment

A subject having a peanut allergy can be treated for the peanut allergy by administering a series of doses of an allergenic peanut composition to the subject during the course of a therapy regimen. The therapy can include increasing the dose of the allergenic peanut composition over a period of time, thereby desensitizing the subject to peanut antigens. The therapy may be multi-phasic, for example by including two, three, or more phases, such as an initial escalation phase, an up-dosing phase, and/or a maintenance phase. The phases, such as the initial escalation phase or the up-dosing phase can include one or more sub-phases, in which a dose of the allergenic peanut composition is periodically increased. In some embodiments, the treatment therapy is an oral immunotherapy dosing regimen.

The initial escalation phase can include administration of a plurality of small doses of the allergenic peanut composition to the subject, which may occur in the same day. The small doses can be spaced by a period of time, such as about 10 minutes to about 60 minutes, or about 20 minutes to about 30 minutes. The initial escalation phase may include 1, 2, 3, 4, or 5 or more doses. The doses may be, for example between about 0.1 mg peanut protein to about 6 mg peanut protein.

The up-dosing phase of an oral immunotherapy can be divided into a plurality of sub-phases. Treatment during the up-dosing phase can include administering to the subject a plurality of doses of an allergenic peanut composition, which are periodically increased. For example, each sub-phase can include administering a daily dose of the allergenic peanut composition for a period of time, such as two weeks. After the completion of the sub-phase, treatment can be advanced into a subsequent sub-phase in which an increased daily dose of the allergenic peanut composition is administered for a period of time, such as about two weeks. In some embodiments, the up-dosing phase of the treatment comprises between 2 sub-phases and 10 sub-phases. In some embodiments, the doses administered during the up-dosing phase range from about 3 mg peanut protein to about 300 mg peanut protein.

Treatment of the peanut allergy can include a maintenance phase in which a dose of the allergenic peanut composition is regularly administered to the subject. The maintenance dose can be at the same dose or a higher dose as the dose administered during the final sub-phase of the up-dosing phase. The maintenance dose can be, for example, about 200 mg to about 500 mg peanut protein, such as about 250 mg to about 400 mg, or about 300 mg peanut protein. In some embodiments, the maintenance dose is administered daily. In some embodiments, the maintenance dose is administered for about 24 weeks.

The level of peanut-specific IgE in the subject can be a factor taken into consideration when selecting how and/or whether the subject should be treated during the course of treatment. For example, in some embodiments, the subject is selected for a treatment regimen based on having a level of peanut-specific IgEs at or below a predetermined threshold (such as about 100 kU/L). In some embodiments, the subject is selected for the treatment regimen only if the level of peanut-specific IgEs is at or below the predetermined threshold. A level of peanut-specific IgE above the predetermined threshold does not necessarily exclude a subject from treatment. For example, in some embodiments, the subject undergoes heightened monitoring for an allergic reaction (such as a hypersensitivity, anaphylaxis (for example anaphylactic shock), gastrointestinal symptoms (such as abdominal pain or vomiting), or eosinophilic esophagitis (EoE)). The level of peanut-specific IgE in the subject can also be taken into consideration as to whether the subject can be advanced to a subsequent phase or sub-phase of the treatment regimen.

In some embodiments, there is a method of treating a subject for a peanut allergy, comprising administering to the subject at least one dose of an allergenic peanut composition, wherein the subject is selected for treatment based on having a level of peanut-specific IgEs at or below a predetermined threshold (such as about 100 kU/L). In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of peanut-specific IgEs is determined at a time proximal to the administration of the dose.

In some embodiments, there is a method of treating a subject for a peanut allergy using an oral immunotherapy dosing regimen, comprising orally administering to the subject at least one dose of an allergenic peanut composition, wherein the subject is selected for treatment based on having a level of peanut-specific IgEs at or below a predetermined threshold (such as about 100 kU/L). In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of peanut-specific IgEs is determined at a time proximal to the administration of the dose.

In some embodiments, there is a method of treating a subject for a peanut allergy using an oral immunotherapy dosing regimen, comprising orally administering to the subject at least one dose of an allergenic peanut composition during an initial escalation phase of the oral immunotherapy dosing regimen, wherein the subject is selected for treatment based on having a level of peanut-specific IgEs at or below a predetermined threshold (such as about 100 kU/L) at the start of the initial escalation phase. In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of the peanut-specific IgEs is determined at a time proximal to the initiation of the initial escalation phase of the treatment. In some embodiments, the level of peanut-specific IgEs is determined at a time proximal to the administration of the dose.

In some embodiments, there is a method of treating a subject for a peanut allergy using an oral immunotherapy dosing regimen, comprising orally administering to the subject at least one dose of an allergenic peanut composition during an up-dosing phase of the oral immunotherapy dosing regimen, wherein the subject is selected for treatment based on having a level of peanut-specific IgEs at or below a predetermined threshold (such as about 100 kU/L). In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of the peanut-specific IgEs is determined at a time proximal to the initiation of an initial escalation phase of the treatment. In some embodiments, the level of the peanut-specific IgEs is determined at a time proximal to the initiation of an up-dosing phase of the treatment. In some embodiments, the level of the peanut-specific IgEs is determined at a time proximal to the initiation of an up-dosing sub-phase of the treatment. In some embodiments, the level of peanut-specific IgEs is determined at a time proximal to the administration of the dose.

In some embodiments, there is a method of treating a subject for a peanut allergy using an oral immunotherapy dosing regimen, comprising orally administering to the subject at least one dose of an allergenic peanut composition during a maintenance phase of the oral immunotherapy dosing regimen, wherein the subject is selected for treatment based on having a level of peanut-specific IgEs at or below a predetermined threshold (such as about 100 kU/L). In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of the peanut-specific IgEs is determined at a time proximal to the initiation of an initial escalation phase of the treatment. In some embodiments, the level of the peanut-specific IgEs is determined at a time proximal to the initiation of an up-dosing phase of the treatment. In some embodiments, the level of the peanut-specific IgEs is determined at a time proximal to the initiation of an up-dosing sub-phase of the treatment. In some embodiments, the level of the peanut-specific IgEs is determined at a time proximal to the initiation of a maintenance phase of the treatment. In some embodiments, the level of peanut-specific IgEs is determined at a time proximal to the administration of the dose.

In some embodiments, there is a method of treating a subject for a peanut allergy, comprising: receiving a level of peanut-specific IgEs in the subject; and administering to the subject at least one dose of an allergenic peanut composition, wherein the subject is selected for treatment based on having a level of peanut-specific IgEs at or below a predetermined threshold (such as about 100 kU/L). In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of peanut-specific IgEs is determined at a time proximal to the administration of the dose.

In some embodiments, there is a method of treating a subject for a peanut allergy using an oral immunotherapy dosing regimen, comprising: receiving a level of peanut-specific IgEs in the subject; and orally administering to the subject at least one dose of an allergenic peanut composition, wherein the subject is selected for treatment based on having a level of peanut-specific IgEs at or below a predetermined threshold (such as about 100 kU/L). In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of peanut-specific IgEs is determined at a time proximal to the administration of the dose.

In some embodiments, there is a method of treating a subject for a peanut allergy using an oral immunotherapy dosing regimen, comprising: receiving a level of peanut-specific IgEs in the subject; and orally administering to the subject at least one dose of an allergenic peanut composition during an initial escalation phase of the oral immunotherapy dosing regimen, wherein the subject is selected for treatment based on having a level of peanut-specific IgEs at or below a predetermined threshold (such as about 100 kU/L) at the start of the initial escalation phase. In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of the peanut-specific IgEs is determined at a time proximal to the initiation of the initial escalation phase of the treatment. In some embodiments, the level of peanut-specific IgEs is determined at a time proximal to the administration of the dose.

In some embodiments, there is a method of treating a subject for a peanut allergy using an oral immunotherapy dosing regimen, comprising: receiving a level of peanut-specific IgEs in the subject; and orally administering to the subject at least one dose of an allergenic peanut composition during an up-dosing phase of the oral immunotherapy dosing regimen, wherein the subject is selected for treatment based on having a level of peanut-specific IgEs at or below a predetermined threshold (such as about 100 kU/L). In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of the peanut-specific IgEs is determined at a time proximal to the initiation of an initial escalation phase of the treatment. In some embodiments, the level of the peanut-specific IgEs is determined at a time proximal to the initiation of an up-dosing phase of the treatment. In some embodiments, the level of the peanut-specific IgEs is determined at a time proximal to the initiation of an up-dosing sub-phase of the treatment. In some embodiments, the level of peanut-specific IgEs is determined at a time proximal to the administration of the dose.

In some embodiments, there is a method of treating a subject for a peanut allergy using an oral immunotherapy dosing regimen, comprising: receiving a level of peanut-specific IgEs in the subject; and orally administering to the subject at least one dose of an allergenic peanut composition during a maintenance phase of the oral immunotherapy dosing regimen, wherein the subject is selected for treatment based on having a level of peanut-specific IgEs at or below a predetermined threshold (such as about 100 kU/L). In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of the peanut-specific IgEs is determined at a time proximal to the initiation of an initial escalation phase of the treatment. In some embodiments, the level of the peanut-specific IgEs is determined at a time proximal to the initiation of an up-dosing phase of the treatment. In some embodiments, the level of the peanut-specific IgEs is determined at a time proximal to the initiation of an up-dosing sub-phase of the treatment. In some embodiments, the level of the peanut-specific IgEs is determined at a time proximal to the initiation of a maintenance phase of the treatment. In some embodiments, the level of peanut-specific IgEs is determined at a time proximal to the administration of the dose.

In some embodiments, there is a method of treating a subject for a peanut allergy, comprising: measuring a level of peanut-specific IgEs in the subject; and administering to the subject at least one dose of an allergenic peanut composition, wherein the subject is selected for treatment based on having a level of peanut-specific IgEs at or below a predetermined threshold (such as about 100 kU/L). In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of peanut-specific IgEs is determined at a time proximal to the administration of the dose.

In some embodiments, there is a method of treating a subject for a peanut allergy using an oral immunotherapy dosing regimen, comprising: measuring a level of peanut-specific IgEs in the subject; and orally administering to the subject at least one dose of an allergenic peanut composition, wherein the subject is selected for treatment based on having a level of peanut-specific IgEs at or below a predetermined threshold (such as about 100 kU/L). In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of peanut-specific IgEs is determined at a time proximal to the administration of the dose.

In some embodiments, there is a method of treating a subject for a peanut allergy using an oral immunotherapy dosing regimen, comprising: measuring a level of peanut-specific IgEs in the subject; and orally administering to the subject at least one dose of an allergenic peanut composition during an initial escalation phase of the oral immunotherapy dosing regimen, wherein the subject is selected for treatment based on having a level of peanut-specific IgEs at or below a predetermined threshold (such as about 100 kU/L) at the start of the initial escalation phase. In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of the peanut-specific IgEs is determined at a time proximal to the initiation of the initial escalation phase of the treatment. In some embodiments, the level of peanut-specific IgEs is determined at a time proximal to the administration of the dose.

In some embodiments, there is a method of treating a subject for a peanut allergy using an oral immunotherapy dosing regimen, comprising: measuring a level of peanut-specific IgEs in the subject; and orally administering to the subject at least one dose of an allergenic peanut composition during an up-dosing phase of the oral immunotherapy dosing regimen, wherein the subject is selected for treatment based on having a level of peanut-specific IgEs at or below a predetermined threshold (such as about 100 kU/L). In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of the peanut-specific IgEs is determined at a time proximal to the initiation of an initial escalation phase of the treatment. In some embodiments, the level of the peanut-specific IgEs is determined at a time proximal to the initiation of an up-dosing phase of the treatment. In some embodiments, the level of the peanut-specific IgEs is determined at a time proximal to the initiation of an up-dosing sub-phase of the treatment. In some embodiments, the level of peanut-specific IgEs is determined at a time proximal to the administration of the dose.

In some embodiments, there is a method of treating a subject for a peanut allergy using an oral immunotherapy dosing regimen, comprising: measuring a level of peanut-specific IgEs in the subject; and orally administering to the subject at least one dose of an allergenic peanut composition during a maintenance phase of the oral immunotherapy dosing regimen, wherein the subject is selected for treatment based on having a level of peanut-specific IgEs at or below a predetermined threshold (such as about 100 kU/L). In some embodiments, the level of peanut-specific IgEs is a primary factor in determining whether the dose should be administered. In some embodiments, the level of peanut-specific IgEs is an exclusive factor in determining whether the dose should be administered. In some embodiments, the dose is administered to the subject only if the level of peanut-specific IgEs is at or below the predetermined threshold. In some embodiments, the level of peanut-specific IgEs is determined prior to the initiation of treatment. In some embodiments, the level of peanut-specific IgEs is determined at a time proximal to the initiation of treatment. In some embodiments, the level of the peanut-specific IgEs is determined at a time proximal to the initiation of an initial escalation phase of the treatment. In some embodiments, the level of the peanut-specific IgEs is determined at a time proximal to the initiation of an up-dosing phase of the treatment. In some embodiments, the level of the peanut-specific IgEs is determined at a time proximal to the initiation of an up-dosing sub-phase of the treatment. In some embodiments, the level of the peanut-specific IgEs is determined at a time proximal to the initiation of a maintenance phase of the treatment. In some embodiments, the level of peanut-specific IgEs is determined at a time proximal to the administration of the dose.

Individuals allergic to peanut allergens and peanut allergenic compositions risk an allergic response upon exposure to the allergenic compounds. Although the level of peanut-specific IgEs determined prior to or during the course of treatment can be used to predict the risk of an adverse event subjects may nevertheless suffer from an adverse event during the course of treatment. A severe or life threatening adverse event related to peanut allergy is often treated by administering injectable epinephrine (adrenaline) to the subject. Under certain circumstances, a single dose of epinephrine may not be sufficient, and a second dose is administered to the subject to treat the allergic response. Doses are generally about 0.15 mg of injectable epinephrine for subjects less than about 30 kilograms, or about 0.3 mg of injectable epinephrine if the subject weighs about 30 kilograms or more.

The level of IgEs in a subject receiving treatment (for example, an oral immunotherapy dosing regimen) for a peanut allergy by administering at least one dose of an allergic peanut composition to the subject can be used to assess the likelihood of an allergic reaction that requires administration of epinephrine to the subject. The method includes receiving a level of peanut-specific IgEs in the subject (which may be determined prior to or during the course of treatment); and assessing the likelihood of an allergic reaction that requires administration of epinephrine to the patient, wherein a level of peanut-specific IgEs at or below a predetermined threshold indicates a reduced likelihood of an allergic reaction that requires administration of epinephrine during treatment, and wherein a level of peanut-specific IgEs above the predetermined threshold indicates an increased likelihood of an allergic reaction that requires administration of epinephrine during treatment. The predetermined threshold of the level of peanut-specific IgEs may be, for example, about 100 kU/L. The method can also include administering to the subject at least one dose of an allergic peanut composition. In some embodiments, the method includes measuring the level of peanut-specific of IgEs. If the subject has a level of peanut-specific IgEs above the predetermined threshold, and therefore has an increased likelihood of an allergic reaction that requires administering of epinephrine during treatment, the subject is not precluded from being treated. However, it may be recommended or prescribed to the subject that the subject have immediate access to at least two doses of epinephrine if the subject has a level of peanut-specific IgEs above the predetermined threshold. The epinephrine is generally injected in the patient for treatment of the allergic reaction by subcutaneous injection.

In some embodiments, the subjects treated for the peanut allergy, for example by oral immunotherapy are 18 years of age or older. In some embodiments, the subjects treated for the peanut allergy are 17 years of age or younger (such as between about 4 years of age and about 17 years of age, between about 4 years of age and 11 years of age, or between about 12 years of age and about 17 years of age).

Methods of Monitoring a Subject for an Adverse Event

As mentioned above, a level of peanut-specific IgEs in a subject above the predetermined threshold does not necessarily exclude the subject from treatment of a peanut allergy. However, in some embodiments, a subject having a level of peanut-specific IgEs above the predetermined threshold (such as about 100 kU/L) indicates that the subject is in need of heightened monitoring for an allergic reaction during the course of the immunotherapy or following administration of a dose of the allergenic peanut composition. Such heightened monitoring may include, for example, active monitoring of the subject for symptoms of an allergic reaction (such as hypersensitivity, anaphylaxis, gastrointestinal symptoms, or eosinophilic esophagitis) in a clinical setting after administration of the dose of the allergenic peanut composition, which may be longer monitoring period than for a subject with a level of peanut-specific IgEs below the predetermined threshold; an increased frequency of clinical visits after beginning an up-dosing sub-phase; monitoring of heart rate and/or respiratory rate of the subject for a period of time after administration of the dose of the allergenic peanut composition; monitoring blood oxygen of the subject for a period of time after administration of the dose of the allergenic peanut composition; or monitoring of blood pressure of the subject for a period of time after administration of the dose of the allergenic peanut composition.

During the course of treatment, such as by oral immunotherapy, the level of peanut-specific IgEs can increase before decreasing. For example, the level of peanut-specific IgEs in a subject at the end of an up-dosing phase may be substantially higher (such as above a predetermined threshold such as about 100 kU/L) than the level of peanut-specific IgEs in the subject prior to the start of treatment. However, it has been found that the level of peanut-specific IgEs decreases during the maintenance phase of treatment. Since a level of peanut-specific IgEs above a predetermined threshold (such as about 100 kU/L) indicates a need for heightened monitoring and a level of peanut-specific IgEs below the predetermined threshold can indicate a decreased need (compared to a subject with a level of peanut-specific IgEs above the predetermined threshold) or no need for heightened monitoring, monitoring of the level of peanut-specific IgEs can be a useful indicator for monitoring the subject during the course of treatment. For example, monitoring the subject for an adverse event can include measuring a level of peanut-specific IgEs in the subject during the course of treatment, such as during an up-dosing phase of treatment or a maintenance phase of treatment, wherein a level of peanut-specific IgEs above a predetermined threshold (such as about 100 kU/L) indicates a need for heightened monitoring, a delayed or skipped dose of the allergenic peanut composition, or a decreased dose of the allergenic peanut composition.

By way of example, a level of peanut-specific IgEs are monitored in subject during a maintenance phase of a treatment for a peanut allergy, such as an oral immunotherapy treatment regimen. The peanut-specific IgE level can be measured, for example, weekly, every two weeks, or monthly during the maintenance phase. During the maintenance phase of the treatment phase, the level of peanut-specific IgEs decreases. If the subject has a level of peanut-specific IgEs below the predetermined threshold (such as about 100 kU/L), heightened monitoring is not needed and can be suspended if previously employed. If the subject has a level of peanut-specific IgEs above the predetermined threshold (such as about 100 kU/L), the subject can be subjected to heightened monitoring a delayed or skipped dose of the allergenic peanut composition, or a decreased dose of the allergenic peanut composition until the level of peanut-specific IgEs is below the predetermined threshold.

The level of peanut-specific IgEs may be determined in the subject at a time proximal to the start of treatment, a time proximal to the administration of the dose, or at a time proximal to the start of a phase or sub-phase of a treatment regimen. For example, in some embodiments, the level of peanut-specific IgEs is determined approximately within 7 days, within 5 days, within 72 hours, within 48 hours, within 24 hours, within 12 hours, within 6 hours, within 4 hours, within 3 hours, within 2 hours, or within 1 hour prior to the initiation of the treatment, the administration of the dose, or initiation of a phase or sub-phase of the treatment regimen.

In some embodiments, there is a method of treating a subject for a peanut allergy, comprising administering to the subject at least one dose of an allergenic peanut composition, wherein the subject undergoes heightened monitoring for an allergic reaction if a level of peanut-specific IgEs in the subject is above a predetermined threshold (such as about 100 kU/L). In some embodiments, the level of peanut-specific IgEs is determined prior to the start of treatment. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising administering to the subject at least one dose of an allergenic peanut composition as part of an oral immunotherapy dosing regimen, wherein the subject undergoes heightened monitoring for an allergic reaction if a level of peanut-specific IgEs in the subject is above a predetermined threshold (such as about 100 kU/L). In some embodiments, the level of peanut-specific IgEs is determined prior to the start of treatment. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising administering to the subject at least one dose of an allergenic peanut composition as part of an initial escalation phase of an oral immunotherapy dosing regimen, wherein the subject undergoes heightened monitoring for an allergic reaction if a level of peanut-specific IgEs in the subject is above a predetermined threshold (such as about 100 kU/L). In some embodiments, the level of peanut-specific IgEs is determined prior to the start of the oral immunotherapy dosing regimen. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising administering to the subject at least one dose of an allergenic peanut composition as part of an up-dosing phase of an oral immunotherapy dosing regimen, wherein the subject undergoes heightened monitoring for an allergic reaction if a level of peanut-specific IgEs in the subject is above a predetermined threshold (such as about 100 kU/L). In some embodiments, the level of peanut-specific IgEs is determined prior to the start of the oral immunotherapy dosing regimen. In some embodiments, the level of peanut-specific IgEs is determined proximal to the start of the up-dosing phase of the oral immunotherapy dosing regimen. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising administering to the subject at least one dose of an allergenic peanut composition as part of a maintenance phase of an oral immunotherapy dosing regimen, wherein the subject undergoes heightened monitoring for an allergic reaction if a level of peanut-specific IgEs in the subject is above a predetermined threshold (such as about 100 kU/L). In some embodiments, the level of peanut-specific IgEs is determined prior to the start of treatment. In some embodiments, the level of peanut-specific IgEs is determined proximal to the start of the maintenance phase of the oral immunotherapy dosing regimen. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: receiving a level of peanut-specific IgEs in the subject; and administering to the subject at least one dose of an allergenic peanut composition, wherein the subject undergoes heightened monitoring for an allergic reaction if the level of peanut-specific IgEs in the subject is above a predetermined threshold (such as about 100 kU/L). In some embodiments, the level of peanut-specific IgEs is determined prior to the start of treatment. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: receiving a level of peanut-specific IgEs in the subject; and administering to the subject at least one dose of an allergenic peanut composition as part of an oral immunotherapy dosing regimen, wherein the subject undergoes heightened monitoring for an allergic reaction if the level of peanut-specific IgEs in the subject is above a predetermined threshold (such as about 100 kU/L). In some embodiments, the level of peanut-specific IgEs is determined prior to the start of treatment. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: receiving a level of peanut-specific IgEs in the subject; and administering to the subject at least one dose of an allergenic peanut composition as part of an initial escalation phase of an oral immunotherapy dosing regimen, wherein the subject undergoes heightened monitoring for an allergic reaction if the level of peanut-specific IgEs in the subject is above a predetermined threshold (such as about 100 kU/L). In some embodiments, the level of peanut-specific IgEs is determined prior to the start of the oral immunotherapy dosing regimen. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: receiving a level of peanut-specific IgEs in the subject; and administering to the subject at least one dose of an allergenic peanut composition as part of an up-dosing phase of an oral immunotherapy dosing regimen, wherein the subject undergoes heightened monitoring for an allergic reaction if the level of peanut-specific IgEs in the subject is above a predetermined threshold (such as about 100 kU/L). In some embodiments, the level of peanut-specific IgEs is determined prior to the start of the oral immunotherapy dosing regimen. In some embodiments, the level of peanut-specific IgEs is determined proximal to the start of the up-dosing phase of the oral immunotherapy dosing regimen. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: receiving a level of peanut-specific IgEs in the subject; and administering to the subject at least one dose of an allergenic peanut composition as part of a maintenance phase of an oral immunotherapy dosing regimen, wherein the subject undergoes heightened monitoring for an allergic reaction if the level of peanut-specific IgEs in the subject is above a predetermined threshold (such as about 100 kU/L). In some embodiments, the level of peanut-specific IgEs is determined prior to the start of treatment. In some embodiments, the level of peanut-specific IgEs is determined proximal to the start of the maintenance phase of the oral immunotherapy dosing regimen. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: measuring a level of peanut-specific IgEs in the subject; and administering to the subject at least one dose of an allergenic peanut composition, wherein the subject undergoes heightened monitoring for an allergic reaction if the level of peanut-specific IgEs in the subject is above a predetermined threshold (such as about 100 kU/L). In some embodiments, the level of peanut-specific IgEs is determined prior to the start of treatment. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: measuring a level of peanut-specific IgEs in the subject; and administering to the subject at least one dose of an allergenic peanut composition as part of an oral immunotherapy dosing regimen, wherein the subject undergoes heightened monitoring for an allergic reaction if the level of peanut-specific IgEs in the subject is above a predetermined threshold (such as about 100 kU/L). In some embodiments, the level of peanut-specific IgEs is determined prior to the start of treatment. In some embodiments, the level of peanut-specific IgEs is determined proximal to administration of the dose.

In some embodiments, there is a method of treating a subject for a peanut allergy, comprising: measuring a level of peanut-specific IgEs in the subject; and administering to the subject at least one dose of an allergenic peanut composition as part of an initial escalation phase of an oral immunotherapy dosing regimen, wherein the subject undergoes heightened monitoring for an allergic reaction if the level of peanut-specific IgEs in the subject is above a predetermined threshold (such as about 100 kU/L). In some embodiments, the level of peanut-specific IgEs is determined prior to the start of the oral immunotherapy dosing regimen. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: measuring a level of peanut-specific IgEs in the subject; and administering to the subject at least one dose of an allergenic peanut composition as part of an up-dosing phase of an oral immunotherapy dosing regimen, wherein the subject undergoes heightened monitoring for an allergic reaction if the level of peanut-specific IgEs in the subject is above a predetermined threshold (such as about 100 kU/L). In some embodiments, the level of peanut-specific IgEs is determined prior to the start of the oral immunotherapy dosing regimen. In some embodiments, the level of peanut-specific IgEs is determined proximal to the start of the up-dosing phase of the oral immunotherapy dosing regimen. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: measuring a level of peanut-specific IgEs in the subject; and administering to the subject at least one dose of an allergenic peanut composition as part of a maintenance phase of an oral immunotherapy dosing regimen, wherein the subject undergoes heightened monitoring for an allergic reaction if the level of peanut-specific IgEs in the subject is above a predetermined threshold (such as about 100 kU/L). In some embodiments, the level of peanut-specific IgEs is determined prior to the start of treatment. In some embodiments, the level of peanut-specific IgEs is determined proximal to the start of the maintenance phase of the oral immunotherapy dosing regimen. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: measuring a level of peanut-specific IgEs in the subject; and administering to the subject at least one dose of an allergenic peanut composition, wherein the subject undergoes heightened monitoring for an allergic reaction if the level of peanut-specific IgEs in the subject is above a predetermined threshold (such as about 100 kU/L). In some embodiments, the level of peanut-specific IgEs is determined prior to the start of treatment. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: measuring a level of peanut-specific IgEs in the subject; administering to the subject at least one dose of an allergenic peanut composition as part of an oral immunotherapy dosing regimen; and monitoring the subject, wherein the subject undergoes heightened monitoring for an allergic reaction if the level of peanut-specific IgEs in the subject is above a predetermined threshold (such as about 100 kU/L) compared to a subject that has a level of peanut-specific IgE at or less than the predetermined threshold. In some embodiments, the level of peanut-specific IgEs is determined prior to the start of treatment. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: measuring a level of peanut-specific IgEs in the subject; administering to the subject at least one dose of an allergenic peanut composition as part of an initial escalation phase of an oral immunotherapy dosing regimen; and monitoring the subject, wherein the subject undergoes heightened monitoring for an allergic reaction if the level of peanut-specific IgEs in the subject is above a predetermined threshold (such as about 100 kU/L) compared to a subject that has a level of peanut-specific IgE at or less than the predetermined threshold. In some embodiments, the level of peanut-specific IgEs is determined prior to the start of the oral immunotherapy dosing regimen. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: measuring a level of peanut-specific IgEs in the subject; administering to the subject at least one dose of an allergenic peanut composition as part of an up-dosing phase of an oral immunotherapy dosing regimen; and monitoring the subject, wherein the subject undergoes heightened monitoring for an allergic reaction if the level of peanut-specific IgEs in the subject is above a predetermined threshold (such as about 100 kU/L) compared to a subject that has a level of peanut-specific IgE at or less than the predetermined threshold. In some embodiments, the level of peanut-specific IgEs is determined prior to the start of the oral immunotherapy dosing regimen. In some embodiments, the level of peanut-specific IgEs is determined proximal to the start of the up-dosing phase of the oral immunotherapy dosing regimen. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

In some embodiments, there is a method of treating a subject for a peanut allergy, comprising: measuring a level of peanut-specific IgEs in the subject; administering to the subject at least one dose of an allergenic peanut composition as part of a maintenance phase of an oral immunotherapy dosing regimen; and monitoring the subject, wherein the subject undergoes heightened monitoring for an allergic reaction if the level of peanut-specific IgEs in the subject is above a predetermined threshold (such as about 100 kU/L) compared to a subject that has a level of peanut-specific IgE at or less than the predetermined threshold. In some embodiments, the level of peanut-specific IgEs is determined prior to the start of treatment. In some embodiments, the level of peanut-specific IgEs is determined proximal to the start of the maintenance phase of the oral immunotherapy dosing regimen. In some embodiments, the level of peanut-specific IgEs is determined proximal to administration of the dose. In some embodiments, heightened monitoring comprises a longer clinical visit following administration of the dose compared to a subject having a level of peanut-specific IgEs at or below the predetermined threshold. In some embodiments, heightened monitoring comprises active monitoring of one or more symptoms related to an allergic reaction.

Ongoing Monitoring During the Course of Treatment

In some embodiments, biomarkers described herein, such a level of peanut-specific IgE, antigen-specific IgE (such as Ara h1, Ara h2, and/or Ara h6 specific IgE), peanut-specific IgG4, antigen-specific IgG4 (such as Ara h1, Ara h2, and/or Ara h6 specific IgG4), the ratio of peanut-specific IgE to peanut-specific IgG4 ("psIgE/psIgG4"), or the ratio of antigen-specific IgE to antigen-specific IgG4 in the subject can be monitored during the course of treatment of the peanut allergy, such as an oral immunotherapy dosing regimen. The level of the biomarker can be measured one or more (such as 2, 3, 4, 5, 6, 7, 8, 9, or 10 or more) times during the course of treatment. In some embodiments, the level of the biomarker in the subject is measured during or after an initial escalation phase of the treatment, before, during, or after an up-dosing phase or up-dosing sub-phase of the treatment, or before or during a maintenance phase of the treatment.

The level of peanut-specific IgEs in the subject can also be useful for monitoring the subject during the course of treatment of the peanut allergy, for example during the course of an oral immunotherapy dosing regimen. The level of peanut-specific IgEs can be used, for example, to help reduce the risk or incidence of an adverse event in a subject receiving treatment for the peanut allergy, to evaluate a symptom that may arise during the course of treatment of the peanut allergy, or to adjust a dose or dosing schedule of administration of an allergenic peanut composition.

The level of peanut-specific IgEs in the subject is also associated with a likelihood of an allergic reaction (such as a hypersensitivity, anaphylaxis (for example anaphylactic shock), gastrointestinal symptoms (such as abdominal pain or vomiting), or eosinophilic esophagitis (EoE)). Therefore, a reduction of the level of peanut-specific IgEs during the course of treatment indicates the patient is less likely to have an allergic reaction, and the level of peanut-specific IgEs can be measured to monitor this likelihood. The reduction of the level of peanut-specific IgEs can be measured for example, at two or more time points during the course of treatment. In some embodiments, the level of peanut-specific IgE is measured at the start of maintenance phase of treatment and during the maintenance phase of treatment.

A subject that has a level of peanut-specific IgEs at or below a predetermined threshold (such as about 100 kU/L) has a low risk of an adverse event related to treatment of the peanut allergy compared to a subject having a level of peanut-specific IgEs above the predetermined threshold. The risk of an adverse event in a subject being related to the treatment regimen (such as an oral immunotherapy dosing regimen) is sufficiently small that the level of peanut-specific IgEs in the subject can be used as a factor taken into consideration when determining whether the symptom is related to the treatment regimen. The symptom could be a symptom of an allergic reaction, but could also be a symptom of another cause. For example, a gastrointestinal symptom, such as vomiting or abdominal pain, could be caused by an allergic reaction to the dose of allergenic peanut composition administered during the course of treatment, or could be caused by another source, such as a gastrointestinal virus. The level of peanut-specific IgEs in the subject can be used as a factor in determining the source of the symptoms. In some embodiments, the level of peanut-specific IgEs is determined at a time proximal to and/or prior to the start of the treatment regimen. In some embodiments, the level of peanut-specific IgE is a level at or proximal to the initiation of treatment, and in some embodiments the level of peanut-specific IgE is a level during or proximal to the symptom adverse event. In some embodiments, the level of peanut-specific IgEs is determined approximately within 7 days, within 5 days, within 72 hours, within 48 hours, within 24 hours, within 12 hours, within 6 hours, within 4 hours, within 3 hours, within 2 hours, or within 1 hour prior to the start of the treatment regimen. In some embodiments, the level of peanut-specific IgEs is determined during or proximal to the symptom or adverse event.

If the symptom is determined to be related to the treatment for the peanut allergy, or if the level of IgE in the subject is above the predetermined threshold, the treatment, such as the amount of the dose or the dosing schedule, can be adjusted or terminated. For example, in some embodiments, administration of a dose is delayed or skipped if the symptom is determined to be related to the treatment or if the level of IgE in the subject is above the predetermined threshold. In some embodiments, a dose increase is delayed during an up-dosing phase of the treatment if the symptom is determined to be related to the treatment or if the level of IgE in the subject is above the predetermined threshold. A delay may include, for example, a temporary pause in administration of a dose for a period of time, such as about 60 days or less, about 45 days or less, about 30 days or less, about 15 days or less. In some embodiments, a delay includes a temporary pause in administration of the dose for a period of time of about 10 days or more, about 15 days or more, about 30 days or more, or about 45 days or more. In some embodiment, treatment is terminated if it is determined that the symptom is related to the treatment.

The level of peanut-specific IgEs in a subject can be used to monitor treatment for a peanut allergy in a subject. In some embodiments, a method of monitoring treatment for a peanut allergy in a subject comprises measuring a level of peanut-specific IgEs in the subject during the course of treatment for the peanut allergy. In some embodiments, a method of monitoring treatment for a peanut allergy in a subject using an oral immunotherapy treatment regimen comprises measuring a level of peanut-specific IgEs in the subject during the course of treatment. In some embodiments, the level of peanut-specific IgEs in the subject is measured during or after an initial escalation phase of the treatment, before, during, or after an up-dosing phase or up-dosing sub-phase of the treatment, or before or during a maintenance phase of the treatment. In some embodiments, the method includes adjusting a dose of an allergenic peanut composition based on the level of peanut-specific IgEs in the subject. For example, in some embodiments, the dose is reduced (for example, during an up-dosing phase or a maintenance phase of a treatment regimen) if the level of peanut-specific IgEs in the subject is above a pre-determined threshold (such as about 100 kU/L). In some embodiments, the dose is not increased or an increase of the dose is delayed during an initial escalation phase or an up-dosing phase of a treatment regimen if the level of peanut-specific IgEs in the subject is above the pre-determined threshold (such as about 100 kU/L). In some embodiments, the dose of the allergenic peanut composition is increased if or only if the level of peanut-specific IgEs in the subject is at or below the pre-determined threshold (such as about 100 kU/L).

In some embodiments, there is a method of evaluating a symptom in an subject during the course of treatment of a peanut allergy, comprising: receiving a level of peanut-specific IgEs in the subject having a symptom; and determining whether the symptom is related to the treatment, wherein a level of peanut-specific IgEs at or below a predetermined threshold (such as about 100 kU/L) indicates that the symptom is not caused by the treatment. In some embodiments, the symptom is a gastrointestinal symptom, such as vomiting or abdominal pain. In some embodiments, administration of a dose is delayed or skipped if the symptom is determined to be related to the treatment. In some embodiments, a dose increase is delayed during an up-dosing phase of the treatment if the symptom is determined to be related to the treatment. In some embodiment, treatment is terminated if it is determined that the symptom is related to the treatment.

In some embodiments, there is a method of evaluating a symptom in an subject during the course of treatment of a peanut allergy using an oral immunotherapy dosing regimen, comprising: receiving a level of peanut-specific IgEs in the subject having a symptom; and determining whether the symptom is related to the treatment, wherein a level of peanut-specific IgEs at or below a predetermined threshold (such as about 100 kU/L) indicates that the symptom is not caused by the oral immunotherapy dosing regimen. In some embodiments, the symptom is a gastrointestinal symptom, such as vomiting or abdominal pain.

In some embodiments, there is a method of evaluating a symptom in an subject during the course of treatment of a peanut allergy, comprising: measuring a level of peanut-specific IgEs in the subject having a symptom; and determining whether the symptom is related to the treatment, wherein a level of peanut-specific IgEs at or below a predetermined threshold (such as about 100 kU/L) indicates that the symptom is not caused by the treatment. In some embodiments, the symptom is a gastrointestinal symptom, such as vomiting or abdominal pain. In some embodiments, administration of a dose is delayed or skipped if the symptom is determined to be related to the treatment. In some embodiments, a dose increase is delayed during an up-dosing phase of the treatment if the symptom is determined to be related to the treatment. In some embodiment, treatment is terminated if it is determined that the symptom is related to the treatment.

In some embodiments, there is a method of evaluating a symptom in an subject during the course of treatment of a peanut allergy using an oral immunotherapy dosing regimen, comprising: measuring a level of peanut-specific IgEs in the subject having a symptom; and determining whether the symptom is related to the treatment, wherein a level of peanut-specific IgEs at or below a predetermined threshold (such as about 100 kU/L) indicates that the symptom is not caused by the oral immunotherapy dosing regimen. In some embodiments, the symptom is a gastrointestinal symptom, such as vomiting or abdominal pain. In some embodiments, administration of a dose is delayed or skipped if the symptom is determined to be related to the treatment. In some embodiments, a dose increase is delayed during an up-dosing phase of the treatment if the symptom is determined to be related to the treatment. In some embodiment, treatment is terminated if it is determined that the symptom is related to the treatment.

As the risk or incidence of an adverse event in a subject receiving treatment for a peanut allergy is associated with the level of peanut-specific IgEs in the subject, the risk or incidence of an adverse event can be reduced by reducing a dose, delaying administration of a dose, or not increasing a dose during treatment. In some embodiments, the level of peanut-specific IgEs is determined proximal to the time of reducing, delaying, or not increasing the dose, such as about within 72 hours prior, within 48 hours prior, within 24 hours prior, within 12 hours prior, within 6 hours prior, within 4 hours prior, within 3 hours prior, within 2 hours prior, or within 1 hour prior to reducing, delaying, or not increasing the dose. Generally, the dose is reduced, the dose is delayed, or the increase of the dose is delayed only if the subject experiences a compounding factor in addition to a level of peanut-specific IgEs above the predetermined threshold. Such a compounding factor can include, for example, inflammation (which may be systemic inflammation or localized inflammation, for example due to a localized injury or surgery), an infection (for example, a viral, fungal, parasitic, or bacterial infection), an allergic reaction (which may be due to peanut or other allergy causing agent), or a menstruation period. Both the compounding factor and the level of peanut-specific IgEs can be taken into consideration when deciding whether to delay the dose, decrease the dose, or delay increasing a dose of the peanut composition.

In some embodiments, a method of reducing the risk or incidence of an adverse event in a subject receiving treatment for a peanut allergy comprises: receiving a level of peanut-specific IgEs in the subject; and reducing or delaying a dose of an allergenic peanut composition if the level of the peanut-specific IgEs is above a predetermined threshold (such as about 100 kU/L). In some embodiments, the level of the peanut-specific IgEs is determined during the course of treatment. In some embodiments, the level of the peanut-specific IgEs is determined in response to a symptom of an allergic reaction. In some embodiments, the dose is reduced or delayed during an up-dosing phase of the treatment. In some embodiments, the adverse event is an allergic reaction, such as anaphylaxis, a gastrointestinal symptom (such as vomiting or abdominal pain), or eosinophilic esophagitis.

In some embodiments, a method of reducing the risk or incidence of an adverse event in a subject receiving treatment for a peanut allergy comprises: receiving a level of peanut-specific IgEs in the subject; and delaying increasing a dose of an allergenic peanut composition during an up-dosing phase of the treatment if the level of the peanut-specific IgEs is above a predetermined threshold (such as about 100 kU/L). In some embodiments, the level of the peanut-specific IgEs is determined during the course of treatment. In some embodiments, the level of the peanut-specific IgEs is determined in response to a symptom of an allergic reaction. In some embodiments, the adverse event is an allergic reaction, such as anaphylaxis, a gastrointestinal symptom (such as vomiting or abdominal pain), or eosinophilic esophagitis.

In some embodiments, a method of reducing the risk or incidence of an adverse event in a subject receiving oral immunotherapy for a peanut allergy comprises: receiving a level of peanut-specific IgEs in the subject; and reducing or delaying a dose of an allergenic peanut composition if the level of the peanut-specific IgEs is above a predetermined threshold (such as about 100 kU/L). In some embodiments, the level of the peanut-specific IgEs is determined during the course of treatment. In some embodiments, the level of the peanut-specific IgEs is determined in response to a symptom of an allergic reaction. In some embodiments, the dose is reduced or delayed during an up-dosing phase of the treatment. In some embodiments, the adverse event is an allergic reaction, such as anaphylaxis, a gastrointestinal symptom (such as vomiting or abdominal pain), or eosinophilic esophagitis.

In some embodiments, a method of reducing the risk or incidence of an adverse event in a subject receiving oral immunotherapy for a peanut allergy comprises: receiving a level of peanut-specific IgEs in the subject; and delaying increasing a dose of an allergenic peanut composition during an up-dosing phase of the treatment if the level of the peanut-specific IgEs is above a predetermined threshold (such as about 100 kU/L). In some embodiments, the level of the peanut-specific IgEs is determined during the course of treatment. In some embodiments, the level of the peanut-specific IgEs is determined in response to a symptom of an allergic reaction. In some embodiments, the adverse event is an allergic reaction, such as anaphylaxis, a gastrointestinal symptom (such as vomiting or abdominal pain), or eosinophilic esophagitis.

In some embodiments, a method of reducing the risk or incidence of an adverse event in a subject receiving treatment for a peanut allergy comprises: measuring a level of peanut-specific IgEs in the subject; and reducing or delaying a dose of an allergenic peanut composition if the level of the peanut-specific IgEs is above a predetermined threshold (such as about 100 kU/L). In some embodiments, the dose is reduced during an up-dosing phase of the treatment. In some embodiments, the adverse event is an allergic reaction, such as anaphylaxis or eosinophilic esophagitis. In some embodiments, the level of the peanut-specific IgEs is determined during the course of treatment. In some embodiments, the level of the peanut-specific IgEs is determined in response to a symptom of an allergic reaction. In some embodiments, the dose is reduced or delayed during an up-dosing phase of the treatment. In some embodiments, the adverse event is an allergic reaction, such as anaphylaxis, a gastrointestinal symptom (such as vomiting or abdominal pain), or eosinophilic esophagitis.

In some embodiments, a method of reducing the risk or incidence of an adverse event in a subject receiving treatment for a peanut allergy comprises: measuring a level of peanut-specific IgEs in the subject; and delaying increasing a dose of an allergenic peanut composition during an up-dosing phase of the treatment if the level of the peanut-specific IgEs is above a predetermined threshold (such as about 100 kU/L). In some embodiments, the level of the peanut-specific IgEs is determined during the course of treatment. In some embodiments, the level of the peanut-specific IgEs is determined in response to a symptom of an allergic reaction. In some embodiments, the adverse event is an allergic reaction, such as anaphylaxis, a gastrointestinal symptom (such as vomiting or abdominal pain), or eosinophilic esophagitis.

In some embodiments, a method of reducing the risk or incidence of an adverse event in a subject receiving oral immunotherapy for a peanut allergy comprises: measuring a level of peanut-specific IgEs in the subject; and reducing or delaying a dose of an allergenic peanut composition if the level of the peanut-specific IgEs is above a predetermined threshold (such as about 100 kU/L). In some embodiments, the dose is reduced during an up-dosing phase of the treatment. In some embodiments, the adverse event is an allergic reaction, such as anaphylaxis or eosinophilic esophagitis. In some embodiments, the level of the peanut-specific IgEs is determined during the course of treatment. In some embodiments, the level of the peanut-specific IgEs is determined in response to a symptom of an allergic reaction. In some embodiments, the dose is reduced or delayed during an up-dosing phase of the treatment. In some embodiments, the adverse event is an allergic reaction, such as anaphylaxis, a gastrointestinal symptom (such as vomiting or abdominal pain), or eosinophilic esophagitis.

In some embodiments, a method of reducing the risk or incidence of an adverse event in a subject receiving oral immunotherapy for a peanut allergy comprises: measuring a level of peanut-specific IgEs in the subject; and delaying increasing a dose of an allergenic peanut composition during an up-dosing phase of the treatment if the level of the peanut-specific IgEs is above a predetermined threshold (such as about 100 kU/L). In some embodiments, the level of the peanut-specific IgEs is determined during the course of treatment. In some embodiments, the level of the peanut-specific IgEs is determined in response to a symptom of an allergic reaction. In some embodiments, the adverse event is an allergic reaction, such as anaphylaxis, a gastrointestinal symptom (such as vomiting or abdominal pain), or eosinophilic esophagitis.

During the course of treatment, a later dose or dosing schedule can be adjusted based on a previous dose and a level of peanut-specific IgE determined in response to the administration of the earlier dose. In some embodiments, there method of adjusting a dose of an allergenic peanut composition, comprising: administering a first dose of the allergenic peanut composition to a subject with a peanut allergy; receiving a level of peanut-specific IgEs in the subject after administration of the first dose; and administering a second dose of the allergenic peanut composition to the subject, wherein the second dose is based on the first dose and the level of peanut-specific IgEs in the subject. In some embodiments, the second dose is lower than the first dose if the level of peanut-specific IgEs is above a predetermined threshold. In some embodiments, the administration of the second dose is delayed if the level of peanut-specific IgEs is above a predetermined threshold. In some embodiments, the second dose is the same as the first dose if the level of peanut-specific IgEs is above a predetermined threshold. In some embodiments, the second dose is increased relative to the first dose if the level of peanut-specific IgEs is at or below the predetermined threshold. In some embodiments, the predetermined threshold is about 100 kU/L. In some embodiments, receiving the level of peanut-specific IgEs in the subject comprises measuring the level of peanut-specific IgEs.

The level of peanut-specific IgG4 can additionally or alternatively be determined prior to treatment, determined or monitored during the course of treatment, or determined at the end of treatment. For example, the level of peanut-specific IgG4 can be determined during or following an up-dosing phase and/or during or following a maintenance phase of the treatment. During the course of treatment, the level of peanut-specific IgG4 generally increases, and an increase in the level of peanut-specific IgG4 is an indicator of successful oral immunotherapy treatment. Therefore, the level of peanut-specific IgG4 can be used to monitor treatment of the peanut allergy. The level of peanut-specific IgG4 may be a total level of one or more (or all) of peanut allergen specific IgG4. For example, the level of peanut-specific IgG4 may be a level of Ara h1-specific IgG4, Ara h2-specific IgG4, Ara h3-specific IgG4, Ara h6-specific IgG4, Ara h8-specific IgG4, or any other peanut allergen specific IgG4; or the level of peanut-specific IgG4 may be a total of any one or more peanut levels of an allergen specific IgG4.

Exemplary Treatment Regimens

In some embodiments, the subject being treated for a food allergy is unlikely to tolerate oral immunotherapy, i.e., the subject is unlikely to respond favorably to OIT alone. For instance, the subject being treated for peanut allergy may not be capable of tolerate about 1 mg or lower amounts of peanut allergens. In some embodiments, the subject being treated for peanut allergy may not tolerate about 6 mg or higher amounts of peanut allergens. In other embodiments, the subject being treated for peanut allergy may not tolerate about 12 mg, 20 mg, 40 mg, 80 mg, 120 mg, 160 mg, 200 mg, 240 mg, 300 mg, 400 mg, 500 mg, 600 mg, 700 mg, 900 mg, 1200 mg, 1500 mg, 1800 mg, 2000 mg or higher amounts of peanut allergens.

The terms "a method for treating a subject suffering from a food allergy," "a method for desensitizing a subject suffering from a food allergy," and "a method for preventing or reducing the risk or severity of food allergy reaction in a subject" may be used interchangeably throughout this application.

A food allergen is administered according to a dosing schedule. The dosing schedule for an individual patient may vary depending on the age, health conditions, the nature and type of food allergen etc. An exemplary dosing schedule for treating peanut allergy comprises: (a) administering to a subject suffering from peanut allergy escalating doses of about 0.5 mg, about 1.0 mg, about 1.5 mg, about 3.0 mg, and about 6 mg of the peanut proteins in about 30 minute intervals on day 1; (b) optionally, administering a maximum tolerated dose (or a 3.0 mg dose) from day 1 for up to 2 weeks; and (c) administering single doses of about 12 mg, about 20 mg, about 40 mg, about 80 mg, about 120 mg, about 160 mg, about 200 mg, about 240 mg, and about 300 mg of the peanut proteins at two week intervals.

Another exemplary dosing schedule for treating peanut allergy comprises: (a) administering to the subject escalating doses of about 0.5 mg, about 1.0 mg, about 1.5 mg, about 3.0 mg, and about 6 mg of the peanut proteins in about 30-minute intervals on day 1; (b) optionally, administering a maximum tolerated dose from day 1 for up to 2 weeks; (c) administering single doses of about 12 mg, about 20 mg, about 40 mg, about 80 mg, about 120 mg, about 160 mg, about 200 mg, about 240 mg, and about 300 mg of the peanut proteins at two week intervals up to 21 weeks; (d) administering a maintenance dose of about 300 mg of the peanut proteins for up to 24 weeks; and (e) administering single doses of about 400 mg, about 475 mg, about 575 mg, about 775 mg, about 950 mg, about 1250 mg, about 1425 mg, about 1625 mg, and about 2000 mg at two week intervals.

U.S. Pre-grant Publication No. 2014/0271721 discloses oral immunotherapy methods and dosing schedules for treating peanut allergy; this publication is incorporated by reference herein in its entirety for all purposes.

Compositions/Formulations

Compositions and methods for treating peanut allergy are described in detail in U.S. Pre-grant Publication No. 2014/027172 and PCT Publication No. WO 2014/159609, both of which are incorporated by reference herein in their entireties. Methods for preparing peanut protein formulations are described in detail for U.S. Pre-grant Publication No. 2014/0271836, which is incorporated by reference herein in its entirety.

A composition for treating food allergy may comprise the food allergen, or alternatively, one or more proteins isolated from the food allergen, and optionally, may further comprise one or more diluents, one or more glidants, and one or more lubricants. For instance, in one embodiment, a composition for treating peanut allergy comprises peanut flour, or alternatively, one or more proteins isolated from peanut flour, one or more diluents, one or more glidants, and one or more lubricants.

A composition for treating peanut allergy may contain, in one aspect, peanut flour, or alternatively, one or more proteins isolated from peanut flour. In one embodiment, peanut flour comprises Arah1, Arah2 and Arah6 proteins. In another embodiment, peanut flour contains as active ingredients: Arah1, Arah2 and Arah6 proteins.

In one embodiment, a final formulation for treating peanut allergy, comprises peanut flour (containing characterized peanut allergen proteins Ara h1, Ara h2 and Ara h6) formulated with a diluent, a glidant and a lubricant in graduated doses, comprising capsules containing 0.5 mg, 1 mg, 10 mg, 100 mg, 475 mg, 500 mg, or 1000 mg of peanut flour. Each capsule may be opened and the content mixed into taste-masking food immediately prior to administration.

In another embodiment, a final formulation for treating peanut allergy, consists of peanut flour (containing characterized peanut allergen proteins Ara h1, Ara h2 and Ara h6) formulated with a bulking and a flow agent in graduated doses, comprising capsules containing 0.5 mg, 1 mg, 10 mg, 100 mg, 475 mg, 500 mg, or 1000 mg of peanut flour. Each capsule may be opened and the content mixed into taste-masking food immediately prior to administration.

In one embodiment, the dose of the composition for treating peanut allergy is 0.5 mg and the concentration of Ara h1 comprises from about 0.035 to about 0.075 mg.

In another embodiment, the dose of the composition for treating peanut allergy is 1.0 mg and the concentration of Ara h1 comprises from about 0.075 to about 0.15 mg.

In another embodiment, the dose of the composition for treating peanut allergy is 10.0 mg and the concentration of Ara h1 comprises from about 0.5 to about 1.5 mg.

In another embodiment, the dose of the composition for treating peanut allergy is 100.0 mg and the concentration of Ara h1 comprises from about 7.5 to about 15 mg.

In another embodiment, the dose of the composition for treating peanut allergy is 475 mg and the concentration of Ara h1 comprises from about 35 to about 60 mg.

In one embodiment, dose of the composition for treating peanut allergy is 0.5 mg and the concentration of Ara h2 comprises from about 0.035 to about 0.075 mg.

In another embodiment, the dose of the composition for treating peanut allergy is 1.0 mg and the concentration of Ara h2 comprises from about 0.075 to about 0.175 mg.

In another embodiment, the dose of the composition for treating peanut allergy is 10.0 mg and the concentration of Ara h2 comprises from about 0.5 to about 1.75 mg.

In another embodiment, the dose of the composition for treating peanut allergy is 100.0 mg and the concentration of Ara h2 comprises from about 7.5 to about 1.15 mg.

In another embodiment, the dose of the composition for treating peanut allergy is 475 mg and the concentration of Ara h2 comprises from about 45 to about 65 mg.

In another embodiment, the dose of the composition for treating peanut allergy is 0.5 mg and the concentration of Ara h6 comprises from about 0.015 to about 0.06 mg.

In another embodiment, the dose of the composition for treating peanut allergy is 1.0 mg and the concentration of Ara h6 comprises from about 0.025 to about 1.0 mg.

In another embodiment, the dose of the composition for treating peanut allergy is 10.0 mg and the concentration of Ara h6 comprises from about 0.35 to about 1.0 mg.

In another embodiment, the dose of the composition for treating peanut allergy is 100.0 mg and the concentration of Ara h6 comprises from about 3.5 to about 10 mg.

In another embodiment, the dose of the composition for treating peanut allergy is 475 mg and the concentration of Ara h6 comprises from about 15 to 40 mg.

In yet another embodiment, the ratio of Ara h2:Ara h6 in a composition for treating peanut allergy is about 2.

Amounts of Ara h proteins are based upon peanut protein being about 50% w/w of the flour and the ratio of Ara h proteins in the extractable protein is representative of the composition within the composition.

All patent and non-patent documents referenced throughout this disclosure are incorporated by reference herein in their entirety for all purposes.

Kits

Further provided herein are kits that include an allergenic peanut formulation or peanut composition as described herein and instructions for use. The instructions for use can instructions for any of the methods described herein, such as methods of treating a subject for a peanut allergy (for example by oral immunotherapy) including selecting the subject for treatment based on having a level of peanut-specific IgEs at or below a predetermined threshold (such as about 100 kU/L); instructions for administering the composition or formulation to a subject with a peanut allergy, wherein the subject undergoes heightened monitoring for an allergic reaction if the peanut-specific IgEs in the subject is above a predetermined threshold (such as about 100 kU/L); a method of assessing the suitability of a treatment for a subject with a peanut allergy, wherein the subject having a level of peanut-specific IgEs at or below a predetermined threshold (such as about 100 kU/L) indicates that the treatment is suitable for the subject; a method for evaluating a symptom in a subject during the course of treatment of a peanut allergy, including determining whether the symptom is related to the treatment, wherein a level of peanut-specific IgEs at or below a predetermined threshold indicates that the adverse event is not caused by the treatment; methods of monitoring treatment for a peanut allergy in a subject, including measuring a level of peanut-specific IgEs in the subject during the course of treatment; a method of reducing the risk or incidence of an adverse event in a subject receiving treatment for a peanut allergy, including reducing a dose, delaying a dose, or delaying an increase of a dose of the allergenic peanut composition if the level of peanut-specific IgEs is above a predetermined threshold; or a method of adjusting a dose of an allergenic peanut composition, including administering a first dose of the allergenic peanut composition to a subject with a peanut allergy, receiving a level of peanut-specific IgEs in the subject after administration of the first dose, and administering a second dose of the allergenic peanut composition to the subject, wherein the second dose is based on the first dose and the level of peanut-specific IgEs in the subject.

EXEMPLARY EMBODIMENTS

The following embodiments are exemplary and not intended to limit the scope of the invention described herein.

Embodiment 1

A method of treating a subject for a peanut allergy, comprising:
administering to the subject at least one dose of an allergenic peanut composition, wherein the subject is selected for treatment based on having a level of peanut-specific IgEs at or below a predetermined threshold.

Embodiment 2

A method of treating a subject for a peanut allergy, comprising:
selecting a subject for treatment based on having a level of peanut-specific IgEs at or below a predetermined threshold; and
administering to the selected subject at least one dose of an allergenic peanut composition.

Embodiment 3

A method of treating a subject for a peanut allergy, comprising:
measuring a level of peanut-specific IgEs for the subject;
selecting the subject for treatment based on having a level of peanut-specific IgEs at or below a predetermined threshold; and
administering to the selected subject at least one dose of an allergenic peanut composition.

Embodiment 4

A method of treating a subject for a peanut allergy, comprising:
measuring a level of peanut-specific IgEs for the subject prior to the start of treatment;
selecting the subject for treatment based on having a level of peanut-specific IgEs at or below a predetermined threshold prior to the start of treatment;
administering to the selected subject a plurality of doses of an allergenic peanut composition; and
monitoring the level of peanut-specific IgEs in the selected subject during the course of treatment.

Embodiment 5

A method of treating a subject for a peanut allergy, comprising:
measuring a level of peanut-specific IgEs for the subject prior to the start of treatment;
selecting the subject for treatment based on having a level of peanut-specific IgEs at or below a predetermined threshold prior to the start of treatment;
administering to the selected subject a plurality of doses of an allergenic peanut composition; and
monitoring the level of peanut-specific IgEs in the selected subject during the course of treatment, wherein:
(1) the subject undergoes heightened monitoring for an allergic reaction if the level of peanut-specific IgEs in the subject rises above the predetermined threshold during the course of treatment; or
(2) reducing a dose, delaying a dose, or delaying a dose increase of the allergic peanut composition administered to the subject if the level of peanut-specific IgEs in the subject rises above the predetermined threshold during the course of treatment.

Embodiment 6

The method of any one of embodiments 1-5, wherein the predetermined threshold for the level of peanut-specific IgEs is about 100 kU/L.

Embodiment 7

The method of any one of embodiments 1-6, wherein the level of peanut-specific IgEs is determined prior to initiating treatment of the peanut allergy.

Embodiment 8

The method of any one of embodiments 1-7, wherein the does is administered to the subject as part of an oral immunotherapy dosing regimen.

Embodiment 9

The method of embodiment 8, wherein the dose is administered to the subject during an initial escalation phase of the oral immunotherapy dosing regimen.

Embodiment 10

The method of embodiment 9, wherein the dose is administered to the subject during an up-dosing phase of the oral immunotherapy dosing regimen.

Embodiment 11

The method of embodiment 9, wherein the dose is administered to the subject during a maintenance phase of the oral immunotherapy dosing regimen.

Embodiment 12

The method of any one of embodiments 1-11, comprising receiving the level of peanut-specific IgEs.

Embodiment 13

The method of any one of embodiments 1, 2, and 6-12, comprising measuring the level of peanut-specific IgEs.

Embodiment 14

A method of treating a subject for a peanut allergy, comprising:
administering to the subject at least one dose of an allergenic peanut composition, wherein the subject undergoes heightened monitoring for an allergenic reaction if a level of peanut-specific IgEs in the subject is above a predetermined threshold.

Embodiment 15

The method of embodiment 14, wherein the predetermined threshold of the level of peanut-specific IgEs is about 100 kU/L.

Embodiment 16

The method of embodiment 14 or 15, wherein heightened monitoring comprises a longer clinical visit following administration of the dose compared to a subject having a level of peanut-specific IgEs at or below the predetermined threshold.

Embodiment 17

The method of any one of embodiments 14-16, wherein heightened monitoring comprises active monitoring for the allergic reaction.

Embodiment 18

The method of embodiment 17, wherein active monitoring comprises measuring a heart rate, blood pressure, respiratory rate, or blood oxygen.

Embodiment 19

The method of any one of embodiments 14-18, wherein the allergic reaction is hypersensitivity, anaphylaxis, a gastrointestinal symptom, or eosinophilic esophagitis.

Embodiment 20

The method of any one of embodiments 14-19, wherein the dose is administered to the subject as part of an oral immunotherapy dosing regimen.

Embodiment 21

The method of embodiment 20, wherein the dose is administered to the subject during an initial escalation phase of the oral immunotherapy regimen.

Embodiment 22

The method of embodiment 20, wherein the dose is administered to the subject during an up-dosing phase of an oral immunotherapy regimen.

Embodiment 23

The method of embodiment 20, wherein the dose is administered to the subject during a maintenance phase of an oral immunotherapy regimen.

Embodiment 24

The method of any one of embodiments 14-23, comprising receiving the level of peanut-specific IgEs.

Embodiment 25

The method of any one of embodiments 14-24, comprising measuring the level of peanut-specific IgEs.

Embodiment 26

The method of any one of embodiments 14-25, wherein the level of peanut-specific IgEs in the subject is determine prior to initiating treatment of the subject.

Embodiment 27

The method of any one of embodiments 14-25, wherein the level of peanut-specific IgEs in the subject is determined during the course of treatment.

Embodiment 28

A method of assessing the suitability of a treatment for a peanut allergy in a subject, comprising:
receiving a level of peanut-specific IgEs in the subject; and
assessing the suitability of the treatment, wherein the subject having a level of peanut-specific IgEs at or below a predetermined threshold indicates that the treatment is suitable for the subject.

Embodiment 29

The method of embodiment 28, wherein the predetermined threshold of the level of peanut-specific IgEs is about 100 kU/L.

Embodiment 30

The method of embodiment 28 or 29, wherein the treatment is an oral immunotherapy dosage regimen.

Embodiment 31

The method of embodiment 30, comprising initiating administration of the oral immunotherapy dosage regimen to the subject.

Embodiment 32

The method of embodiment 31, wherein initiating administration of the oral immunotherapy dosage regimen to the subject comprises administering an initial escalation phase of the oral immunotherapy regimen to the subject.

Embodiment 33

The method of any one of embodiments 28-32, comprising measuring the level of peanut-specific IgEs in the subject.

Embodiment 34

A method of evaluating a symptom in a subject during the course of treatment of a peanut allergy, comprising:
receiving a level of peanut-specific IgEs in the subject having an adverse event; and
determining whether the symptom is related to the treatment, wherein a level of peanut-specific IgEs at or below a predetermined threshold indicates that the adverse event is not caused by the treatment.

Embodiment 35

A method of evaluating a symptom in a subject during the course of treatment of a peanut allergy, comprising:
administering to a subject a plurality of doses of an allergenic peanut composition;
receiving a level of peanut-specific IgEs in the subject having an adverse event; and
determining whether the symptom is related to the treatment, wherein a level of peanut-specific IgEs at or below a predetermined threshold indicates that the adverse event is not caused by the treatment; and
reducing a dose, delaying a dose, or delaying a dose increase of the allergenic peanut composition administered to the subject if the level of peanut-specific IgEs in the subject is above the predetermined threshold.

Embodiment 36

The method of embodiment 34 or 35, wherein the level of peanut-specific IgE is determined prior to initiating the course of treatment.

Embodiment 37

The method of embodiment 34 or 35, wherein the level of peanut-specific IgE is determined during the course of treatment.

Embodiment 38

The method of embodiment 34 or 35, wherein the level of peanut-specific IgE is determined when the subject is symptomatic.

Embodiment 39

The method of any one of embodiments 34-38, wherein the predetermined threshold of the level of peanut-specific IgEs is about 100 kU/L.

Embodiment 40

The method of any one of embodiments 34-39, wherein the treatment is an oral immunotherapy dosage regimen.

Embodiment 41

The method of any one of embodiments 34-40, wherein the symptom is a gastrointestinal symptom.

Embodiment 42

The method of embodiment 41, wherein the gastrointestinal symptom is vomiting or abdominal pain.

Embodiment 43

The method of any one of embodiments 34-42, comprising delaying a dose increase during an up-dosing phase of the treatment if the symptom is determined to be related to the treatment.

Embodiment 44

The method of any one of embodiments 34-42, comprising reducing or delaying a dose of an allergenic peanut composition administered to the subject if the symptom is determined to be related to the treatment.

Embodiment 45

The method of any one of embodiments 34-42, comprising terminating the treatment if the symptom is determined to be related to the treatment.

Embodiment 46

The method of any one of embodiments 34-45, comprising measuring the level of peanut-specific IgEs.

Embodiment 47

A method of monitoring treatment for a peanut allergy in a subject, comprising:
measuring a level of peanut-specific IgEs in the subject during the course of treatment.

Embodiment 48

The method of embodiment 47, wherein the treatment is an oral immunotherapy dosage regimen.

Embodiment 49

The method of embodiment 47 or 48, comprising reducing or delaying a dose of an allergenic peanut composition if the level of peanut-specific IgEs is above a predetermined threshold.

Embodiment 50

The method of embodiment 47 or 48, comprising delaying a dose increase during an up-dosing phase of the treatment if the level of peanut-specific IgEs is above a predetermined threshold.

Embodiment 51

The method of embodiment 47 or 48, comprising terminating the treatment if the level of peanut-specific IgEs is above a predetermined threshold.

Embodiment 52

The method of embodiment 47 or 48, comprising increasing the dose if the level of peanut-specific IgEs is at or below a predetermined threshold.

Embodiment 53

The method of any one of embodiments 47-52, wherein the predetermined threshold is about 100 kU/L.

Embodiment 54

The method of any one of embodiment 47-53 wherein the level of peanut-specific IgEs is measured following an initial escalation phase of the treatment.

Embodiment 55

The method of any one of embodiments 47-54, wherein the level of peanut-specific IgEs is measured during an up-dosing phase of the treatment.

Embodiment 56

The method of any one of embodiments 47-55, wherein the level of peanut-specific IgEs is measured during a maintenance phase of the treatment.

Embodiment 57

A method of reducing the risk or incidence of an adverse event in a subject receiving treatment for a peanut allergy, comprising:
receiving a level of peanut-specific IgEs in the subject; and
reducing a dose, delaying a dose, or delaying an increase of a dose of an allergenic peanut composition if the level of peanut-specific IgEs is above a predetermined threshold.

Embodiment 58

The method of embodiment 57, wherein the treatment is oral immunotherapy.

Embodiment 59

The method of embodiment 57 or 58, wherein the predetermined level of the peanut-specific IgEs is about 100 kU/L.

Embodiment 60

The method of any one of embodiments 57-59, comprising measuring the level of peanut-specific IgEs in the subject.

Embodiment 61

The method of any one of embodiments 57-60, wherein the adverse event is an allergic reaction.

Embodiment 62

The method of any one of embodiments 57-61, comprising reducing the dose of the allergic peanut composition if the level of peanut-specific IgEs is above the predetermined threshold.

Embodiment 63

The method of embodiment 62, wherein the dose of the allergenic peanut composition is reduced during an up-dosing phase of the treatment.

Embodiment 64

The method of embodiment 62, wherein the dose of the allergenic peanut composition is reduced during a maintenance phase of the treatment.

Embodiment 65

The method of any one of embodiments 57-61, comprising delaying the dose of the allergic peanut composition if the level of peanut-specific IgEs is above the predetermined threshold.

Embodiment 66

The method of embodiment 65, wherein the dose is delayed during an up-dosing phase of the treatment.

Embodiment 67

The method of embodiment 65, wherein the dose is delayed during a maintenance phase of the treatment.

Embodiment 68

The method of any one of embodiments 57-61, comprising delaying the increase of the dose of the allergic peanut composition during an up-dosing phase of the therapy if the level of peanut-specific IgEs is above the predetermined threshold.

Embodiment 69

The method of any one of embodiments 57-68, comprising administering the dose to the subject.

Embodiment 70

A method of adjusting a dose of an allergenic peanut composition, comprising:

administering a first dose of the allergenic peanut composition to a subject with a peanut allergy;

receiving a level of peanut-specific IgEs in the subject after administration of the first dose; and administering a second dose of the allergenic peanut composition to the subject, wherein the second dose is based on the first dose and the level of peanut-specific IgEs in the subject.

Embodiment 71

The method of embodiment 70, wherein the second dose is lower than the first dose if the level of peanut-specific IgEs is above a predetermined threshold.

Embodiment 72

The method of embodiment 70 or 71, wherein the administration of the second dose is delayed if the level of peanut-specific IgEs is above a predetermined threshold.

Embodiment 73

The method of embodiment 70, wherein the second dose is the same as the first dose if the level of peanut-specific IgEs is above a predetermined threshold.

Embodiment 74

The method of embodiment 70, wherein the second dose is increased relative to the first dose if the level of peanut-specific IgEs is at or below the predetermined threshold.

Embodiment 75

The method of any one of embodiments 70-74, wherein the predetermined threshold is about 100 kU/L.

Embodiment 76

The method of any one of embodiments 70-75, comprising measuring the level of peanut-specific IgEs.

Embodiment 77

A method of monitoring treatment for a peanut allergy in a subject, comprising:

measuring a level of peanut-specific IgG4s or a peanut-specific IgE to peanut-specific IgG4 ratio in the subject during the course of treatment.

Embodiment 78

The method of embodiment 77, comprising measuring the level of peanut-specific IgG4s in the subject during the course of treatment.

Embodiment 79

The method of embodiment 77, comprising measuring the peanut-specific IgE to peanut-specific IgG4 ratio in the subject during the course of treatment.

Embodiment 80

The method of any one of embodiments 77-79, wherein the treatment is an oral immunotherapy dosing regimen.

Embodiment 81

The method of any one of embodiment 77-80 wherein the level of peanut-specific IgG4s or the peanut-specific IgE to peanut-specific IgG4 ratio is measured following an initial escalation phase of the treatment.

Embodiment 82

The method of any one of embodiments 77-81, wherein the level of peanut-specific IgG4s or the peanut-specific IgE to peanut-specific IgG4 ratio is measured during an up-dosing phase of the treatment.

Embodiment 83

The method of any one of embodiments 77-82, wherein the level of peanut-specific IgG4s or the peanut-specific IgE to peanut-specific IgG4 ratio is measured during a maintenance phase of the treatment.

Embodiment 84

The method of any one of embodiments 1-83, wherein the subject is a human.

Embodiment 85

The method of any one of embodiments 1-84, wherein the subject is about 17 years of age or younger.

Embodiment 86

The method of embodiment 85, wherein the subject is about 4 years of age to about 17 years of age.

Embodiment 87

The method of any one of embodiments 1-86, wherein the level of peanut-specific IgEs or the level of peanut-specific IgG4s corresponds to a level as measured by a fluorescence enzyme immunoassay auto-analyzer.

Embodiment 88

The method of any one of embodiments 1-87, wherein the level of peanut-specific IgEs or the level of peanut-specific IgG4s is measured by a fluorescence enzyme immunoassay auto-analyzer.

Embodiment 89

A method of treating a subject suffering from a food allergy, comprising:
orally administering at least one dose of at least one allergen to the subject according to a dosing schedule, wherein said patient is determined to be likely to tolerate oral immunotherapy based upon one or more biomarkers as described herein.

Embodiment 90

The method of embodiment 89, wherein said treating is initiating oral immunotherapy in the subject.

Embodiment 91

The method of embodiment 89 or 90, wherein the subject determined to be likely to respond favorably to the oral administration of the food allergen has a food allergen-specific serum IgE level of about 0.35 kU/L to about 17.4 kU/L, about 0.35 kU/L to about 50 kU/L, or about 0.35 kU/L to about 99.9 kU/L.

Embodiment 92

The method of embodiment 89 or 90, wherein the subject determined to be likely to respond favorably to the oral administration of the food allergen has a food allergen-specific serum IgE level of about 0.35 kU/L to about 17.4 kU/L, about 0.35 kU/L to about 20 kU/L, about 0.35 kU/L to about 25 kU/L, about 0.35 kU/L to about 30 kU/L, about 0.35 kU/L to about 35 kU/L, about 0.35 kU/L to about to about 40 kU/L, about 0.35 kU/L to about 45 kU/L, about 0.35 kU/L to about 50 kU/L, about 0.35 kU/L to about 55 kU/L, about 0.35 kU/L to about 60 kU/L, about 0.35 kU/L to about 65 kU/L, about 0.35 kU/L to about 70 kU/L, about 0.35 kU/L to about 75 kU/L, about 0.35 kU/L to about 80 kU/L, about 0.35 kU/L to about 85 kU/L, about 0.35 kU/L to about 90 kU/L, about 0.35 kU/L to about 95 kU/L, or about 0.35 kU/L to about 99 kU/L.

Embodiment 93

The method of embodiments 89 or 90, wherein the subject determined to be likely to respond favorably to the oral administration of the food allergen has a food allergen-specific serum IgE level of about 0.35 kU/L to about 125 kU/L, about 0.35 kU/L to about 150 kU/L, about 0.35 kU/L to about 175 kU/L, about 0.35 kU/L to about 200 kU/L, about 0.35 kU/L to about 225 kU/L, about 0.35 kU/L to about 250 kU/L, about 0.35 kU/L to about 275 kU/L, about 0.35 kU/L to about 300 kU/L, about 0.35 kU/L to about 325 kU/L, about 0.35 kU/L to about 350 kU/L, about 0.35 kU/L to about 375 kU/L, about 0.35 kU/L to about 400 kU/L, about 0.35 kU/L to about 425 kU/L, or about 0.35 kU/L to about 450 kU/L.

Embodiment 94

A method of treating a subject suffering from a food allergy, comprising:
orally administering at least one dose of at least one allergen to the subject according to a dosing schedule, and coadministering a therapeutic agent that is an antagonist of one or more immunological mediators of allergy, wherein said patient is determined to be unlikely to tolerate oral immunotherapy based upon one or more biomarkers as described herein.

Embodiment 95

The method of embodiment 94, wherein the subject unlikely to respond favorably to the oral administration of the food allergen has a food allergen-specific serum IgE level of about 50 kU/L or more, about 55 kU/L or more, about 60 kU/L or more, about 65 kU/L or more, about 70 kU/L or more, about 75 kU/L or more, about 80 kU/L or more, about 85 kU/L or more, about 90 kU/L or more, about 95 kU/L or more, or about 100 kU/L or more, about 125 kU/L or more, about 150 kU/L or more, about 175 kU/L or more, about 200 kU/L or more, about 225 kU/L or more, about 250 kU/L or more, about 275 kU/L or more, about 300 kU/L or more, about 325 kU/L or more, about 350 kU/L or more, about 375 kU/L or more, or about 400 kU/L or more.

Embodiment 96

The method of embodiment 94 or 95, wherein the subject unlikely to respond favorably to the oral administration of the food allergen has a food allergen-specific serum IgE level of about 100 kU/L or more.

Embodiment 97

The method of any one of embodiments 89-96, wherein the subject is allergic to one or more peanut allergens.

Embodiment 98

The method of any one of embodiments 89-97, wherein the subject suffering from a food allergy is likely or unlikely to respond favorably to the oral administration of the food allergen based on the levels of one or more biomarkers selected from the group consisting of: total IgE, allergen-specific IgE, allergen-specific IgG4, ratio of IgG to IgE, the ratio of allergen-specific IgE to IgG4, and cell surface markers on immune cells.

Embodiment 99

The method of any one of embodiments 89-97, wherein the subject is allergic to one or more peanut allergens and is likely or unlikely to respond favorably to the oral administration of the peanut allergen based on the levels of one or more biomarkers selected from the group consisting of: total IgE, peanut-specific IgE, Ara h1-specific IgE, Ara h2-specific IgE, Ara h3-specific IgE, Ara h8-specific IgE, Ara h9-specific IgE, peanut-specific IgG4, ratio of IgG to IgE, the ratio of allergen-specific IgE to IgG4 and cell surface markers on immune cells.

Embodiment 100

The method of any one of embodiments 94-99, wherein the therapeutic agent is an IgE antagonist.

Embodiment 101

The method of any one of embodiments 89-100, wherein the at least one dose of at least one allergen is an allergen composition comprising one or more peanut proteins.

Embodiment 102

The method of embodiment 101, wherein the allergen composition comprises one or more characterized peanut proteins and pharmaceutically acceptable excipients.

Embodiment 103

The method of any one of embodiments 89-102, wherein the dosing schedule comprises:
(a) administering to the subject escalating doses of about 0.5 mg, about 1.0 mg, about 1.5 mg, about 3.0 mg, and about 6 mg of the peanut proteins in about 30-minute intervals on day 1;
(b) optionally, administering a maximum tolerated dose or about 3 mg of the peanut proteins from day 1 for up to 2 weeks; and
(c) administering single doses of about 12 mg, about 20 mg, about 40 mg, about 80 mg, about 120 mg, about 160 mg, about 200 mg, about 240 mg, and about 300 mg of the peanut proteins at two week intervals.

Embodiment 104

The method of any one of embodiments 89-103, wherein the dosing schedule comprises:
(a) administering to the subject escalating doses of about 0.5 mg, about 1.0 mg, about 1.5 mg, about 3.0 mg, and about 6 mg of the peanut proteins in about 30-minute intervals on day 1;
(b) optionally, administering a maximum tolerated dose or about 3 mg of the peanut proteins from day 1 for up to 2 weeks;
(c) administering single doses of about 12 mg, about 20 mg, about 40 mg, about 80 mg, about 120 mg, about 160 mg, about 200 mg, about 240 mg, and about 300 mg of the peanut proteins at two week intervals to 21 weeks;
(d) administering a maintenance dose of about 300 mg of the peanut proteins for up to 24 weeks; and
(e) administering single doses of about 400 mg, about 475 mg, about 575 mg, about 775 mg, about 950 mg, about 1250 mg, about 1425 mg, about 1625 mg, and about 2000 mg at two week intervals.

Embodiment 105

A method of diagnosing a subject suffering from a food allergy as likely or unlikely to respond favorably to oral immunotherapy comprising, measuring levels of one or more biomarkers in the subject selected from the group consisting of: total IgE, allergen-specific IgE, allergen-specific IgG4, ratio of IgG to IgE, and the ratio of allergen-specific IgE to IgG4, cell surface markers on immune cells, and combinations thereof.

Embodiment 106

A method of diagnosing a subject suffering from a peanut allergy as likely or unlikely to respond favorably to oral immunotherapy comprising, measuring levels of one or more biomarkers in the subject selected from the group consisting of: total IgE, peanut-specific IgE, Ara h1-specific IgE, Ara h2-specific IgE, Ara h3-specific IgE, Ara h8-specific IgE, Ara h9-specific IgE, peanut-specific IgG4, ratio of IgG to IgE, the ratio of allergen-specific IgE to IgG4 and cell surface markers on immune cells.

Embodiment 107

The method of embodiment 106, wherein the subject suffering from the peanut allergy is diagnosed as incapable of responding favorably to oral immunotherapy alone when the subject has a peanut-specific serum IgE level of about 100 kU/L or more, about 125 kU/L or more, about 150 kU/L or more, about 175 kU/L or more, about 200 kU/L or more, about 225 kU/L or more, about 250 kU/L or more, about 275 kU/L or more, about 300 kU/L or more, about 325 kU/L or more, about 350 kU/L or more, about 375 kU/L or more, or about 400 kU/L or more.

Embodiment 108

A method of treating a subject suffering from a peanut allergy, comprising: orally administering at least one dose of at least one allergen to the subject according to a dosing schedule, and coadministering a therapeutic agent that is an antagonist of one or more immunological mediators of allergy, wherein the subject has a peanut-specific serum IgE level of about 100 kU/L or more, about 125 kU/L or more, about 150 kU/L or more, about 175 kU/L or more, about 200 kU/L or more, about 225 kU/L or more, about 250 kU/L or more, about 275 kU/L or more, about 300 kU/L or more, about 325 kU/L or more, about 350 kU/L or more, about 375 kU/L or more, or about 400 kU/L or more.

Embodiment 109

The method of embodiment 108, wherein the therapeutic agent is an IgE antagonist.

Embodiment 110

The method of embodiment 100 or 109, wherein the IgE antagonist is omalizumab.

Embodiment 111

A method of assessing a likelihood of an allergic reaction that requires administration of epinephrine to a subject receiving treatment for a peanut allergy, wherein the treatment comprises administration of at least one dose of an allergenic peanut composition, the method comprising:
receiving a level of peanut-specific IgEs in the subject; and
assessing the likelihood of an allergic reaction that requires administration of epinephrine to the patient, wherein a level of peanut-specific IgEs at or below a predetermined threshold indicates a reduced likelihood of an allergic reaction that requires administration of epinephrine during treatment, and wherein a level of peanut-specific IgEs above the predetermined threshold indicates an increased likelihood of an allergic reaction that requires administration of epinephrine during treatment.

Embodiment 112

A method of assessing a likelihood of an allergic reaction that requires administration of epinephrine to a subject receiving treatment for a peanut allergy, wherein the treatment comprises administration of at least one dose of an allergenic peanut composition, the method comprising:
receiving a level of peanut-specific IgEs in the subject; and
assessing the likelihood of an allergic reaction that requires administration of epinephrine to the patient, wherein a level of peanut-specific IgEs at or below a predetermined threshold indicates a reduced likelihood of an allergic reaction that requires administration of epinephrine during treatment, and wherein a level of peanut-specific IgEs above the predetermined threshold indicates an increased likelihood of an allergic reaction that requires administration of epinephrine during treatment; and
administering to the subject one or more doses of an allergenic peanut composition if the level of peanut-specific IgEs is at or below the predetermined threshold.

Embodiment 113

The method of embodiment 111 or 112, wherein the predetermined threshold of the level of peanut-specific IgEs is about 100 kU/L.

Embodiment 114

The method of any one of embodiments 111-113, wherein the treatment is an oral immunotherapy dosing regimen.

Embodiment 115

The method of any one of embodiments 111-114, further comprising administering to the subject at least one dose of an allergenic peanut composition.

Embodiment 116

The method of any one of embodiments 111-115, wherein the subject is a human.

Embodiment 117

The method of any one of embodiments 111-116, wherein the subject is about 17 years of age or younger.

Embodiment 118

The method of embodiment 117, wherein the subject is about 4 years of age to about 17 years of age.

Embodiment 119

The method of any one of embodiments 111-118, comprising recommending to the subject that the subject have immediate access to at least two doses of injectable epinephrine for treatment of the allergic reaction if the subject has a level of peanut-specific IgEs above the predetermined threshold.

Embodiment 120

The method of embodiment 119, wherein each dose of epinephrine is about 0.15 mg of injectable epinephrine if the subject weighs less than about 30 kilograms, or about 0.3 mg of injectable epinephrine if the subject weighs about 30 kilograms or more.

Embodiment 121

The method of any one of embodiments 111-120, comprising measuring the level of peanut-specific IgEs in the subject prior to initiating treatment for the peanut allergy.

Embodiment 122

The method of any one of embodiments 111-121, wherein the level of peanut-specific IgEs in the subject is a level determined prior to initiating treatment of the peanut allergy.

Embodiment 123

The method of any one of embodiments 111-122, wherein the level of peanut-specific IgEs in the subject is a level determined during the course of treatment.

Embodiment 124

The method of any one of embodiments 111-123, wherein the level of peanut-specific IgEs corresponds to a level as measured by a fluorescence enzyme immunoassay auto-analyzer.

Embodiment 125

The method of any one of embodiments 111-124, wherein the level of peanut-specific IgEs is measured by a fluorescence enzyme immunoassay auto-analyzer.

Embodiment 126

A method of treating a subject for an allergy to an allergenic food, comprising:
administering to the subject at least one dose of an allergenic food composition, wherein the subject is selected for treatment based on having a level of allergenic food-specific IgEs at or below a predetermined threshold.

Embodiment 127

A method of treating a subject for an allergy to an allergenic food, comprising:
selecting a subject for treatment based on having a level of allergenic food-specific IgEs at or below a predetermined threshold; and
administering to the selected subject at least one dose of an allergenic food composition.

Embodiment 128

A method of treating a subject for an allergy to an allergenic food, comprising:
measuring a level of allergenic food-specific IgEs for the subject;
selecting the subject for treatment based on having a level of allergenic food-specific IgEs at or below a predetermined threshold; and
administering to the selected subject at least one dose of an allergenic food composition.

Embodiment 129

A method of treating a subject for an allergy to an allergenic food, comprising:

measuring a level of allergenic food-specific IgEs for the subject prior to the start of treatment;

selecting the subject for treatment based on having a level of allergenic food-specific IgEs at or below a predetermined threshold prior to the start of treatment;

administering to the selected subject a plurality of doses of an allergenic food composition; and monitoring the level of allergenic food-specific IgEs in the selected subject during the course of treatment.

Embodiment 130

A method of treating a subject for an allergy to an allergenic food, comprising:

measuring a level of allergenic food-specific IgEs for the subject prior to the start of treatment;

selecting the subject for treatment based on having a level of allergenic food-specific IgEs at or below a predetermined threshold prior to the start of treatment;

administering to the selected subject a plurality of doses of an allergenic food composition; and monitoring the level of allergenic food-specific IgEs in the selected subject during the course of treatment, wherein:

(1) the subject undergoes heightened monitoring for an allergic reaction if the level of allergenic food-specific IgEs in the subject rises above the predetermined threshold during the course of treatment; or (2) reducing a dose, delaying a dose, or delaying a dose increase of the allergic food composition administered to the subject if the level of allergenic food-specific IgEs in the subject rises above the predetermined threshold during the course of treatment.

Embodiment 131

The method of any one of embodiments 126-130, wherein the predetermined threshold for the level of allergenic food-specific IgEs is about 100 kU/L.

Embodiment 132

The method of any one of embodiments 126-131, wherein the level of allergenic food-specific IgEs is determined prior to initiating treatment of the allergy to the allergenic food.

Embodiment 133

The method of any one of embodiments 126-132, wherein the does is administered to the subject as part of an oral immunotherapy dosing regimen.

Embodiment 134

The method of embodiment 133, wherein the dose is administered to the subject during an initial escalation phase of the oral immunotherapy dosing regimen.

Embodiment 135

The method of embodiment 133, wherein the dose is administered to the subject during an up-dosing phase of the oral immunotherapy dosing regimen.

Embodiment 136

The method of embodiment 133, wherein the dose is administered to the subject during a maintenance phase of the oral immunotherapy dosing regimen.

Embodiment 137

The method of any one of embodiments 126-136, comprising receiving the level of allergenic food-specific IgEs.

Embodiment 138

The method of any one of embodiments 126, 27, and 131-137, comprising measuring the level of allergenic food-specific IgEs.

Embodiment 139

A method of treating a subject for an allergy to a food allergy, comprising:

administering to the subject at least one dose of an allergenic food composition, wherein the subject undergoes heightened monitoring for an allergenic reaction if a level of allergenic food-specific IgEs in the subject is above a predetermined threshold.

Embodiment 140

The method of embodiment 139, wherein the predetermined threshold of the level of allergenic food-specific IgEs is about 100 kU/L.

Embodiment 141

The method of embodiment 139 or 140, wherein heightened monitoring comprises a longer clinical visit following administration of the dose compared to a subject having a level of allergenic food-specific IgEs at or below the predetermined threshold.

Embodiment 142

The method of any one of embodiments 139-141, wherein heightened monitoring comprises active monitoring for the allergic reaction.

Embodiment 143

The method of embodiment 142, wherein active monitoring comprises measuring a heart rate, blood pressure, respiratory rate, or blood oxygen.

Embodiment 144

The method of any one of embodiments 139-143, wherein the allergic reaction is hypersensitivity, anaphylaxis, a gastrointestinal symptom, or eosinophilic esophagitis.

Embodiment 145

The method of any one of embodiments 139-144, wherein the dose is administered to the subject as part of an oral immunotherapy dosing regimen.

Embodiment 146

The method of embodiment 145, wherein the dose is administered to the subject during an initial escalation phase of the oral immunotherapy regimen.

Embodiment 147

The method of embodiment 145, wherein the dose is administered to the subject during an up-dosing phase of an oral immunotherapy regimen.

Embodiment 148

The method of embodiment 145, wherein the dose is administered to the subject during a maintenance phase of an oral immunotherapy regimen.

Embodiment 149

The method of any one of embodiments 139-148, comprising receiving the level of allergenic food-specific IgEs.

Embodiment 150

The method of any one of embodiments 139-149, comprising measuring the level of allergenic food-specific IgEs.

Embodiment 151

The method of any one of embodiments 139-150, wherein the level of allergenic food-specific IgEs in the subject is determine prior to initiating treatment of the subject.

Embodiment 152

The method of any one of embodiments 139-150, wherein the level of allergenic food-specific IgEs in the subject is determined during the course of treatment.

Embodiment 153

A method of assessing the suitability of a treatment for an allergy to an allergenic food in a subject, comprising:
receiving a level of allergenic food-specific IgEs in the subject; and
assessing the suitability of the treatment, wherein the subject having a level of allergenic food-specific IgEs at or below a predetermined threshold indicates that the treatment is suitable for the subject.

Embodiment 154

The method of embodiment 153, wherein the predetermined threshold of the level of allergenic food-specific IgEs is about 100 kU/L.

Embodiment 155

The method of embodiment 153 or 154, wherein the treatment is an oral immunotherapy dosage regimen.

Embodiment 156

The method of embodiment 155, comprising initiating administration of the oral immunotherapy dosage regimen to the subject.

Embodiment 157

The method of embodiment 156, wherein initiating administration of the oral immunotherapy dosage regimen to the subject comprises administering an initial escalation phase of the oral immunotherapy regimen to the subject.

Embodiment 158

The method of any one of embodiments 153-157, comprising measuring the level of allergenic food-specific IgEs in the subject.

Embodiment 159

A method of evaluating a symptom in a subject during the course of treatment of an allergy for an allergenic food, comprising:
receiving a level of allergenic food-specific IgEs in the subject having an adverse event; and
determining whether the symptom is related to the treatment, wherein a level of allergenic food-specific IgEs at or below a predetermined threshold indicates that the adverse event is not caused by the treatment.

Embodiment 160

A method of evaluating a symptom in a subject during the course of treatment of an allergy for an allergenic food, comprising:
administering to a subject a plurality of doses of an allergenic food composition;
receiving a level of allergenic food-specific IgEs in the subject having an adverse event; and
determining whether the symptom is related to the treatment, wherein a level of allergenic food-specific IgEs at or below a predetermined threshold indicates that the adverse event is not caused by the treatment; and
reducing a dose, delaying a dose, or delaying a dose increase of the allergenic food composition administered to the subject if the level of allergenic food-specific IgEs in the subject is above the predetermined threshold.

Embodiment 161

The method of embodiment 159 or 160, wherein the level of allergenic food-specific IgE is determined prior to initiating the course of treatment.

Embodiment 162

The method of embodiment 159 or 160, wherein the level of allergenic food-specific IgE is determined during the course of treatment.

Embodiment 163

The method of embodiment 159 or 160, wherein the level of allergenic food-specific IgE is determined when the subject is symptomatic.

Embodiment 164

The method of any one of embodiments 159-163, wherein the predetermined threshold of the level of allergenic food-specific IgEs is about 100 kU/L.

Embodiment 165

The method of any one of embodiments 159-164, wherein the treatment is an oral immunotherapy dosage regimen.

Embodiment 166

The method of any one of embodiments 159-165, wherein the symptom is a gastrointestinal symptom.

Embodiment 167

The method of embodiment 166, wherein the gastrointestinal symptom is vomiting or abdominal pain.

Embodiment 168

The method of any one of embodiments 159-167, comprising delaying a dose increase during an up-dosing phase of the treatment if the symptom is determined to be related to the treatment.

Embodiment 169

The method of any one of embodiments 159-167, comprising reducing or delaying a dose of an allergenic food composition administered to the subject if the symptom is determined to be related to the treatment.

Embodiment 170

The method of any one of embodiments 159-167, comprising terminating the treatment if the symptom is determined to be related to the treatment.

Embodiment 171

The method of any one of embodiments 159-170, comprising measuring the level of allergenic food-specific IgEs.

Embodiment 172

A method of monitoring treatment for an allergy for an allergenic food in a subject, comprising:
measuring a level of allergenic food-specific IgEs in the subject during the course of treatment.

Embodiment 173

The method of embodiment 172, wherein the treatment is an oral immunotherapy dosage regimen.

Embodiment 174

The method of embodiment 172 or 173, comprising reducing or delaying a dose of an allergenic food composition if the level of allergenic food-specific IgEs is above a predetermined threshold.

Embodiment 175

The method of embodiment 172 or 173, comprising delaying a dose increase during an up-dosing phase of the treatment if the level of allergenic food-specific IgEs is above a predetermined threshold.

Embodiment 176

The method of embodiment 172 or 173, comprising terminating the treatment if the level of allergenic food-specific IgEs is above a predetermined threshold.

Embodiment 177

The method of embodiment 172 or 173, comprising increasing the dose if the level of allergenic food-specific IgEs is at or below a predetermined threshold.

Embodiment 178

The method of any one of embodiments 172-177, wherein the predetermined threshold is about 100 kU/L.

Embodiment 179

The method of any one of embodiment 172-178 wherein the level of allergenic food-specific IgEs is measured following an initial escalation phase of the treatment.

Embodiment 180

The method of any one of embodiments 172-179, wherein the level of allergenic food-specific IgEs is measured during an up-dosing phase of the treatment.

Embodiment 181

The method of any one of embodiments 172-180, wherein the level of allergenic food-specific IgEs is measured during a maintenance phase of the treatment.

Embodiment 182

A method of reducing the risk or incidence of an adverse event in a subject receiving treatment for a food allergy, comprising:
receiving a level of allergenic food-specific IgEs in the subject; and
reducing a dose, delaying a dose, or delaying an increase of a dose of an allergenic food composition if the level of allergenic food-specific IgEs is above a predetermined threshold.

Embodiment 183

The method of embodiment 182, wherein the treatment is oral immunotherapy.

Embodiment 184

The method of embodiment 182 or 183, wherein the predetermined level of the allergenic food-specific IgEs is about 100 kU/L.

Embodiment 185

The method of any one of embodiments 182-184, comprising measuring the level of allergenic food-specific IgEs in the subject.

Embodiment 186

The method of any one of embodiments 182-185, wherein the adverse event is an allergic reaction.

Embodiment 187

The method of any one of embodiments 182-186, comprising reducing the dose of the allergic food composition if the level of allergenic food-specific IgEs is above the predetermined threshold.

Embodiment 188

The method of embodiment 187, wherein the dose of the allergenic food composition is reduced during an up-dosing phase of the treatment.

Embodiment 189

The method of embodiment 187, wherein the dose of the allergenic food composition is reduced during a maintenance phase of the treatment.

Embodiment 190

The method of any one of embodiments 182-189, comprising delaying the dose of the allergic food composition if the level of allergenic food-specific IgEs is above the predetermined threshold.

Embodiment 191

The method of embodiment 190, wherein the dose is delayed during an up-dosing phase of the treatment.

Embodiment 192

The method of embodiment 190, wherein the dose is delayed during a maintenance phase of the treatment.

Embodiment 193

The method of any one of embodiments 182-192, comprising delaying the increase of the dose of the allergic food composition during an up-dosing phase of the therapy if the level of allergenic food-specific IgEs is above the predetermined threshold.

Embodiment 194

The method of any one of embodiments 182-193, comprising administering the dose to the subject.

Embodiment 195

A method of adjusting a dose of an allergenic food composition, comprising:
administering a first dose of the allergenic food composition to a subject with a food allergy;
receiving a level of allergenic food-specific IgEs in the subject after administration of the first dose; and
administering a second dose of the allergenic food composition to the subject, wherein the second dose is based on the first dose and the level of allergenic food-specific IgEs in the subject.

Embodiment 196

The method of embodiment 195, wherein the second dose is lower than the first dose if the level of allergenic food-specific IgEs is above a predetermined threshold.

Embodiment 197

The method of embodiment 195 or 196, wherein the administration of the second dose is delayed if the level of allergenic food-specific IgEs is above a predetermined threshold.

Embodiment 198

The method of embodiment 195, wherein the second dose is the same as the first dose if the level of allergenic food-specific IgEs is above a predetermined threshold.

Embodiment 199

The method of embodiment 195, wherein the second dose is increased relative to the first dose if the level of allergenic food-specific IgEs is at or below the predetermined threshold.

Embodiment 200

The method of any one of embodiments 195-199, wherein the predetermined threshold is about 100 kU/L.

Embodiment 201

The method of any one of embodiments 195-200, comprising measuring the level of allergenic food-specific IgEs.

Embodiment 202

A method of monitoring treatment for a allergy to an allergenic food in a subject, comprising:
measuring a level of allergenic food-specific IgG4s or an allergenic food-specific IgE to allergenic food-specific IgG4 ratio in the subject during the course of treatment.

Embodiment 203

The method of embodiment 202, comprising measuring the level of allergenic food-specific IgG4s in the subject during the course of treatment.

Embodiment 204

The method of embodiment 202, comprising measuring the allergenic food-specific IgE to allergenic food-specific IgG4 ratio in the subject during the course of treatment.

Embodiment 205

The method of any one of embodiments 202-204, wherein the treatment is an oral immunotherapy dosing regimen.

Embodiment 206

The method of any one of embodiment 202-205 wherein the level of allergenic food-specific IgG4s or the allergenic food-specific IgE to allergenic food-specific IgG4 ratio is measured following an initial escalation phase of the treatment.

Embodiment 207

The method of any one of embodiments 202-206, wherein the level of allergenic food-specific IgG4s or the allergenic food-specific IgE to allergenic food-specific IgG4 ratio is measured during an up-dosing phase of the treatment.

Embodiment 208

The method of any one of embodiments 202-207, wherein the level of allergenic food-specific IgG4s or the allergenic food-specific IgE to allergenic food-specific IgG4 ratio is measured during a maintenance phase of the treatment.

Embodiment 209

A method of assessing a likelihood of an allergic reaction that requires administration of epinephrine to a subject receiving treatment for a food allergy, wherein the treatment comprises administration of at least one dose of an allergenic food composition, the method comprising:
receiving a level of allergenic food-specific IgEs in the subject; and
assessing the likelihood of an allergic reaction that requires administration of epinephrine to the patient, wherein a level of allergenic food-specific IgEs at or below a predetermined threshold indicates a reduced likelihood of an allergic reaction that requires administration of epinephrine during treatment, and wherein a level of allergenic food-specific IgEs above the predetermined threshold indicates an increased likelihood of an allergic reaction that requires administration of epinephrine during treatment.

Embodiment 210

A method of assessing a likelihood of an allergic reaction that requires administration of epinephrine to a subject receiving treatment for a food allergy, wherein the treatment comprises administration of at least one dose of an allergenic food composition, the method comprising:
receiving a level of allergenic food-specific IgEs in the subject; and
assessing the likelihood of an allergic reaction that requires administration of epinephrine to the patient, wherein a level of allergenic food-specific IgEs at or below a predetermined threshold indicates a reduced likelihood of an allergic reaction that requires administration of epinephrine during treatment, and wherein a level of allergenic food-specific IgEs above the predetermined threshold indicates an increased likelihood of an allergic reaction that requires administration of epinephrine during treatment; and
administering to the subject one or more doses of an allergenic food composition if the level of allergenic food-specific IgEs is at or below the predetermined threshold.

Embodiment 211

The method of embodiment 209 or 210, wherein the predetermined threshold of the level of allergenic food-specific IgEs is about 100 kU/L.

Embodiment 212

The method of any one of embodiments 209-211, wherein the treatment is an oral immunotherapy dosing regimen.

Embodiment 213

The method of any one of embodiments 209-212, further comprising administering to the subject at least one dose of an allergenic food composition.

Embodiment 214

The method of any one of embodiments 209-213, comprising recommending to the subject that the subject have immediate access to at least two doses of injectable epinephrine for treatment of the allergic reaction if the subject has a level of allergenic food-specific IgEs above the predetermined threshold.

Embodiment 215

The method of embodiment 214, wherein each dose of epinephrine is about 0.15 mg of injectable epinephrine if the subject weighs less than about 30 kilograms, or about 0.3 mg of injectable epinephrine if the subject weighs about 30 kilograms or more.

Embodiment 216

The method of any one of embodiments 209-215, comprising measuring the level of allergenic food-specific IgEs in the subject prior to initiating treatment for the food allergy.

Embodiment 217

The method of any one of embodiments 209-216, wherein the level of allergenic food-specific IgEs in the subject is a level determined prior to initiating treatment of the food allergy.

Embodiment 218

The method of any one of embodiments 209-216, wherein the level of allergenic food-specific IgEs in the subject is a level determined during the course of treatment.

Embodiment 219

The method of any one of embodiments 126-218, wherein the subject is a human.

Embodiment 220

The method of any one of embodiments 126-219, wherein the subject is about 17 years of age or younger.

Embodiment 221

The method of embodiment 220, wherein the subject is about 4 years of age to about 17 years of age.

Embodiment 222

The method of any one of embodiments 126-221, wherein the level of allergenic food-specific IgEs or the level of allergenic food-specific IgG4s corresponds to a level as measured by a fluorescence enzyme immunoassay autoanalyzer.

Embodiment 223

The method of any one of embodiments 126-222, wherein the level of allergenic food-specific IgEs or the level of allergenic food-specific IgG4s is measured by a fluorescence enzyme immunoassay auto-analyzer.

Embodiments 224

The method of any one of embodiments 1-223, wherein the level of the biomarker, the level of the peanut-specific IgE, the level of the allergenic food-specific IgE, the level of the peanut-specific IgG4, and/or the level of the allergenic food-specific IgG4 is determined in vitro.

Embodiment 225

An allergenic peanut composition for use in treating a subject for a peanut allergy, wherein at least one dose of an allergenic peanut composition is administered to the subject, wherein the subject is selected for treatment based on having a level of peanut-specific IgEs at or below a predetermined threshold.

Embodiment 226

An allergenic peanut composition for use in treating a subject for a peanut allergy, wherein a subject is selected for treatment based on having a level of peanut-specific IgEs at or below a predetermined threshold; and wherein at least one dose of the allergenic peanut composition is administered to the subject.

Embodiment 227

An allergenic peanut composition for use in treating a subject for a peanut allergy, wherein a level of peanut-specific IgEs for the subject is measured in vitro; the subject is selected for treatment based on having a level of peanut-specific IgEs at or below a predetermined threshold; and at least one dose of an allergenic peanut composition is administered to the selected subject.

Embodiment 228

An allergenic peanut composition for use in treating a subject for a peanut allergy, wherein a level of peanut-specific IgEs for the subject is measured in vitro; the subject is selected for treatment based on having a level of peanut-specific IgEs at or below a predetermined threshold; at least one dose of an allergenic peanut composition is administered to the selected subject; and the level of peanut-specific IgEs in the selected subject is monitored in vitro during the course of treatment.

Embodiment 229

An allergenic peanut composition for use in treating a subject for a peanut allergy, wherein a level of peanut-specific IgEs for the subject is measured in vitro; the subject is selected for treatment based on having a level of peanut-specific IgEs at or below a predetermined threshold; at least one dose of an allergenic peanut composition is administered to the selected subject; and the level of peanut-specific IgEs in the selected subject is monitored in vitro during the course of treatment; and wherein (1) the subject undergoes heightened monitoring for an allergic reaction if the level of peanut-specific IgEs in the subject rises above the predetermined threshold during the course of treatment; or (2) a dose of the allergenic peanut composition is reduced, a dose of the allergenic peanut composition administered to the subject is delayed, or an increase of a dose of the allergenic composition is delayed if the level of peanut-specific IgEs in the subject rises above the predetermined threshold during the course of treatment.

Embodiment 230

Use of an allergenic peanut composition in the manufacture of a medicament for treating a subject for a peanut allergy, wherein at least one dose of an allergenic peanut composition is administered to the subject, wherein the subject is selected for treatment based on having a level of peanut-specific IgEs at or below a predetermined threshold.

Embodiment 231

Use of an allergenic peanut composition in the manufacture of a medicament for treating a subject for a peanut allergy, wherein a subject is selected for treatment based on having a level of peanut-specific IgEs at or below a predetermined threshold; and wherein at least one dose of the allergenic peanut composition is administered to the subject.

Embodiment 232

Use of an allergenic peanut composition in the manufacture of a medicament for treating a subject for a peanut allergy, wherein a level of peanut-specific IgEs for the subject is measured in vitro; the subject is selected for treatment based on having a level of peanut-specific IgEs at or below a predetermined threshold; and at least one dose of an allergenic peanut composition is administered to the selected subject.

Embodiment 233

Use of an allergenic peanut composition in the manufacture of a medicament for treating a subject for a peanut allergy, wherein a level of peanut-specific IgEs for the subject is measured in vitro; the subject is selected for treatment based on having a level of peanut-specific IgEs at or below a predetermined threshold; at least one dose of an allergenic peanut composition is administered to the selected subject; and the level of peanut-specific IgEs in the selected subject is monitored in vitro during the course of treatment.

Embodiment 234

Use of an allergenic peanut composition in the manufacture of a medicament for treating a subject for a peanut allergy, wherein a level of peanut-specific IgEs for the subject is measured in vitro; the subject is selected for treatment based on having a level of peanut-specific IgEs at or below a predetermined threshold; at least one dose of an allergenic peanut composition is administered to the selected subject; and the level of peanut-specific IgEs in the selected subject is monitored in vitro during the course of treatment; and wherein (1) the subject undergoes heightened monitoring for an allergic reaction if the level of peanut-specific IgEs in the subject rises above the predetermined threshold during the course of treatment; or (2) a dose of the allergenic peanut composition is reduced, a dose of the allergenic peanut composition administered to the subject is delayed, or an increase of a dose of the allergenic composition is delayed if the level of peanut-specific IgEs in the subject rises above the predetermined threshold during the course of treatment.

Embodiment 235

An allergenic peanut composition for use in treating a subject for a peanut allergy, wherein at least one dose of the allergenic peanut composition is administered to the subject, and wherein the subject undergoes heightened monitoring for an allergenic reaction if a level of peanut-specific IgEs in the subject is above a predetermined threshold.

Embodiment 236

Use of an allergenic peanut composition in the manufacture of a medicament for use in treating a subject for a peanut allergy, wherein at least one dose of the allergenic peanut composition is administered to the subject, and wherein the subject undergoes heightened monitoring for an allergenic reaction if a level of peanut-specific IgEs in the subject is above a predetermined threshold.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods described herein.

Example 1: Treatment of a Patient Allergic to Peanuts

Figure 2:
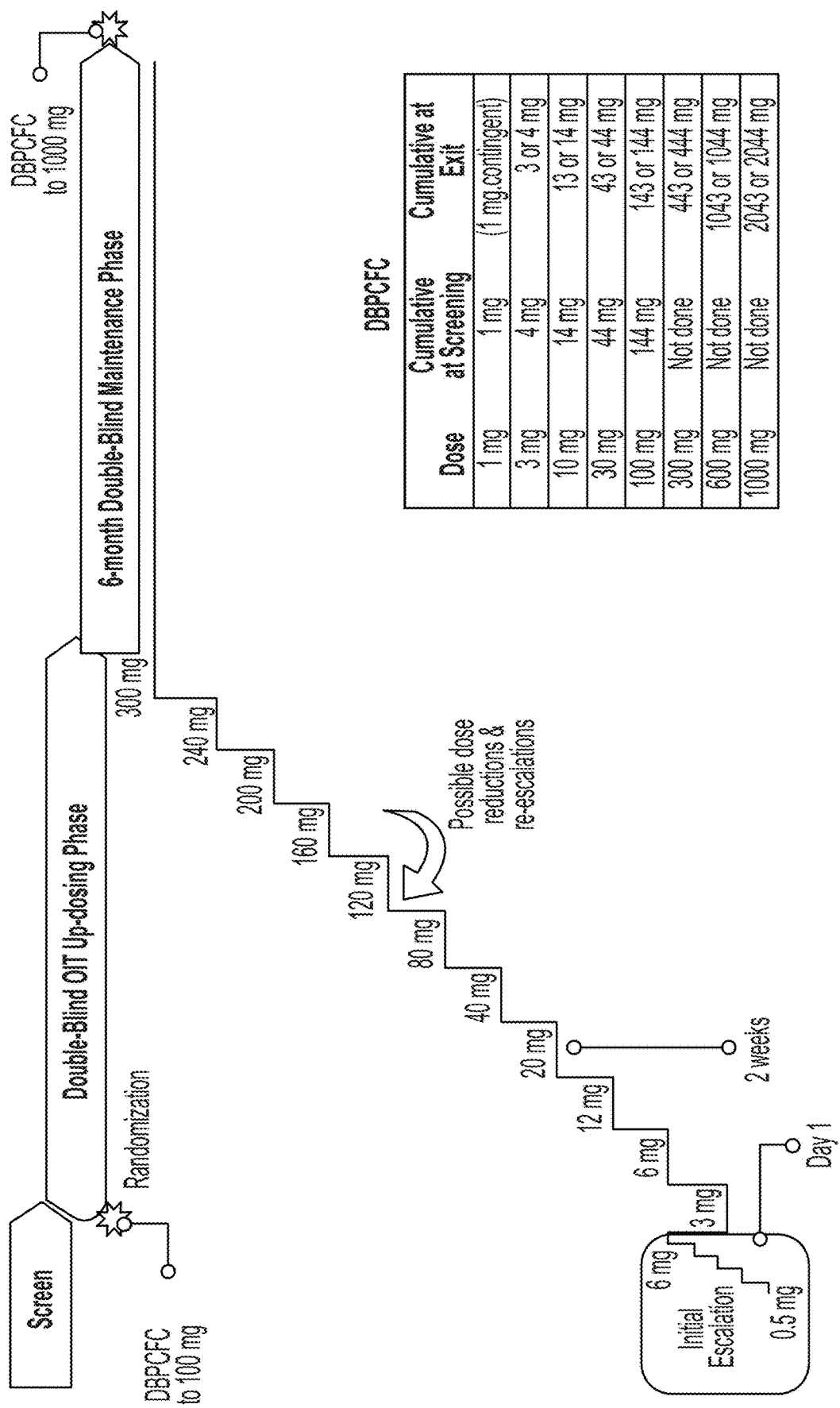
FIG. 2 illustrates an exemplary treatment protocol for treating a peanut allergy patient with oral immunotherapy (OIT).

A peanut allergic patient would be screened according to the methods described above. If the patient is likely to respond favorably to the oral administration of escalating doses of peanut allergens, then the patient would be treated according to protocol set forth below. If the patient is unlikely to respond favorably to the oral administration of escalating doses of peanut allergens, then the patient would not receive a medical intervention. An exemplar treatment protocol for treating a peanut allergy patient with oral immunotherapy (OIT) is shown in FIG. 2.

Exemplary Treatment Protocol for Treating a Peanut Allergy Patient with OIT:

Initial Escalation (2 Days):

Eligible subjects will initiate OIT starting at a dose of 0.5 mg of peanut protein, and then increase the dose incrementally at 20 to 30 minute intervals over the course of a single day to a maximum dose of 6 mg. Subjects who fail to tolerate at least a 3 mg dose will be considered escalation failures. Subjects who tolerate both the 3 mg and 6 mg doses of study product, or who tolerate the 3 mg, but not the 6 mg dose, will undergo confirmatory testing of the tolerability of a 3 mg dose the following day (see Initial Escalation Schedule below).

Up-Dosing:

Subjects will receive daily oral dosing of peanut or placebo OIT for about 5 months (20 weeks, if up-dosing proceeds without holding at, or reducing, a dose level; 40 weeks, maximum). All escalation doses (see escalation table below) will occur in a clinical research center (CRC) or other monitored setting (unless required by a specific institution, no distinction will be drawn between an investigational site, study center office, clinic, or CRC, provided the capability requirements for monitoring and emergency intervention are met by the facility). All up-dosing activities will be performed under the direct observation.

Maintenance:

Those subjects who reach the target maintenance dose of 300 mg/d of study product will enter an approximately 24-week Maintenance Period of continued dosing at 300 mg/d.

TABLE 1

Initial Escalation Period, Day-1, Dosing Schedule

| Day-1 Dose # | Study Product Dose (mg peanut protein or placebo) | Cumulative Study Product Dose (mg peanut protein or placebo) |
|---|---|---|
| 1 | 0.5 | 0.5 |
| 2 | 1 | 1.5 |
| 3 | 1.5 | 3 |
| 4 | 3 | 6 |
| 5 | 6 | 12 |

TABLE 2

Up-dosing Period Dosing Schedule

| Up-dosing Dose # | Study Product Dose (mg peanut protein or placebo) | Interval (weeks) | % Increase |
|---|---|---|---|
| 1 | 3 | 2 | |
| 2 | 6 | 2 | 100% |
| 3 | 12 | 2 | 100% |
| 4 | 20 | 2 | 67% |
| 5 | 40 | 2 | 100% |
| 6 | 80 | 2 | 100% |
| 7 | 120 | 2 | 50% |
| 8 | 160 | 2 | 33% |
| 9 | 200 | 2 | 25% |
| 10 | 240 | 2 | 20% |
| 11 | 300 | 24-Week Maintenance Period | 25% |

Example 2: Treatment of a Peanut Allergy Patient Unlikely to Respond Favorably to the Oral Administration of Escalating Doses of Peanut Allergens A peanut allergic patient would be screened according to the methods described above. If the patient is likely to respond favorably to the oral administration of escalating doses of peanut allergens, then the patient would be treated according to the protocol set forth in Example 1. If the patient is unlikely to respond favorably to the oral administration of escalating doses of peanut allergens, then the patient would be treated with omalizumab before and/or during the OIT treatment protocol set forth in Example 1.

Example 3: Detection of Peanut-Specific IgE in a Subject

Blood samples are collected from subjects seeking oral immunotherapy for a peanut allergy and stored at about 4° C. for same week processing or about −20° C. for longer-term storage. The blood samples are transported to a facility with an immunoautoanalyser or similar device for quantitative immunoassay. Immunoassay solid phases comprising peanut protein extract are prepared. Blood samples are processed and injected onto the solid phase for assay following manufacturer or known protocols for capture of peanut-specific IgE from subject serum or plasma. After washing of the solid phase, anti-IgE antibodies comprising a fluorescent moiety are added to the solid phase. After washing, a developing reagent is added to the solid phase and incubated. The developing reaction is stopped and fluorescent readings are correlated to serum concentration based on comparison to a commercial control. Concentrations are reported in units of kU/L. The subject's peanut-specific IgE level is received by the subject's medical practitioner.

Example 4: Oral Immunotherapy in Subjects Presenting Symptoms

Subjects undergoing an oral immunotherapy dosage regimen for treatment of a known peanut allergy who present symptoms similar to an allergenic reaction, including but not limited to gastrointestinal distress, anaphylaxis, or eosinophilic esophagitis, have a level of peanut-specific IgEs measured. Blood samples are collected, serial diluted if necessary, processed, and assayed from the subject for peanut-specific IgE as described in Example 3. The facility processing the blood sample reports a peanut-specific IgE level to a clinician. If the level of peanut-specific IgE exceeds 100 kU/L, the clinician suspends administration of the oral immunotherapy dosage. After a 30 day delay, administration of the oral immunotherapy dosage is resumed.

Example 5: Heightened Monitoring of a Subject in Response to a Level of Peanut-Specific IgEs A level of peanut-specific IgEs is measured in a subject seeking oral immunotherapy. Blood samples are collected from the subject, serial diluted if necessary, processed, and assayed for peanut-specific IgE serum concentration as described in Example 3. The facility processing the blood sample reports a peanut-specific IgE level to a clinician. If the level of peanut-specific IgE is equal to or less than a threshold value of 100 kU/L, the subject begins a normal course of oral immunotherapy under standard medical supervision. If the subject's level of peanut-specific IgEs exceeds a threshold value of 100 kU/L, the clinician will administer the oral immunotherapy dosage to the subject while increasing monitoring of the subject relative to the subject with a level of peanut-specific IgEs at or below the threshold. Heightened monitoring can include at least weekly testing of a level of peanut-specific IgEs; active monitoring for symptoms of an allergic reaction (such as hypersensitivity, anaphylaxis, gastrointestinal symptoms, or eosinophilic esophagitis) in a clinical setting after administration of the dose of the allergenic peanut composition, which may be for a longer monitoring period than for a subject with a level of peanut-specific IgEs below the predetermined threshold; or monitoring of heart rate and/or respiratory rate of the subject for a period of time after administration of the dose of the allergenic peanut composition.

Example 6: Reducing the Risk or Incidence of an Adverse Event in a Subject Receiving Treatment for a Peanut Allergy A level of peanut-specific IgEs is measured in a subject being treated for a peanut allergy using oral immunotherapy. Blood samples are collected from the subject, serial diluted if necessary, processed, and assayed for peanut-specific IgE serum concentration as described in Example 3. The facility processing the blood sample reports a level of peanut-specific IgEs to a clinician. If the level of peanut-specific IgEs is equal to or less than 100 kU/L, the subject is cleared to maintain the standard course and schedule of oral immunotherapy, absent other indications to the contrary. If the subject's level of peanut-specific IgEs exceeds a threshold value of 100 kU/L, the next dose can be reduced or delayed.

Example 7

Introduction. Two phase 2 trials (ARC001, and its follow-on ARC002) previously demonstrated evidence of efficacy and tolerability of AR101, a pharmaceutical-grade peanut-flour-derived CODIT formulation, in desensitizing peanut-allergic subjects.

Methods. Children and adult subjects with peanut allergy confirmed by double-blind placebo-controlled food challenge (DBPCFC), participated in ARC001, a double-blind placebo-controlled trial (active n=29, placebo n=26), and were followed in ARC002, an open label trial (active n=47). The AR101 updosing period (from 3 mg/d to 300 mg/d) was followed by a 12-week maintenance period (300 mg/d). Peanut skin prick test (SPT) and peanut-specific (ps) IgE (Immulite©, upper quantification limit of 100 $kU_A/L$) were performed at baseline, before randomization. A retrospective cohort analysis was performed to evaluate the safety and efficacy profile of AR101.

Figure 1C:
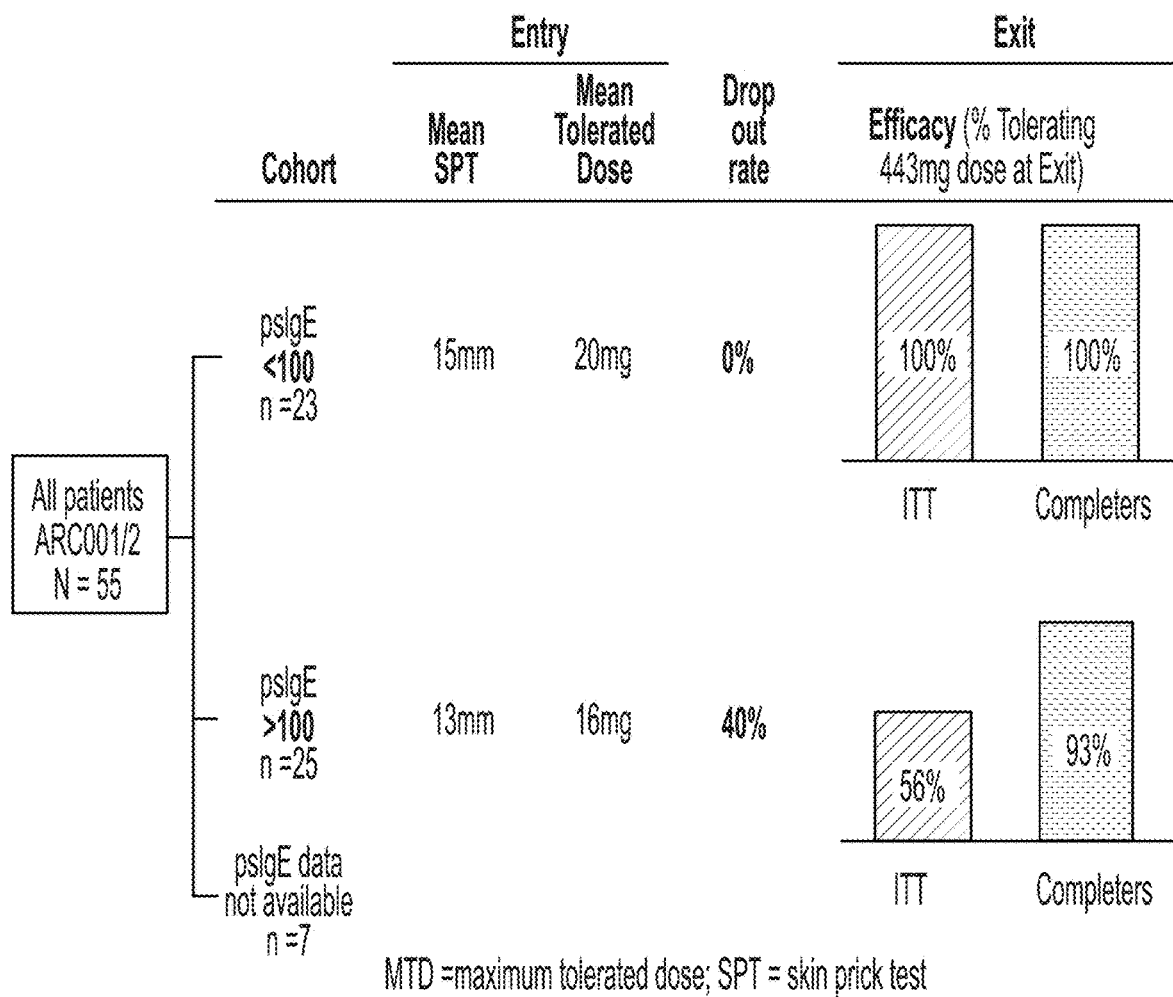
FIG. 1C shows additional post-hoc patient cohort preliminary analysis from a phase 2 clinical trial of an oral immunotherapy (OIT) for the treatment of a peanut allergy.

Results. In a preliminary analysis of the 55 treated patients based on psIgE, 23 had a baseline ps-IgE level of <100 kU/L, 25 patients had a baseline ps-IgE level of >100 kU/L, and data was unavailable for 7 patients during the preliminary analysis. See FIGS. 1A-C. Across all peanut allergic patients (not those limited to the phase 2 study), it is generally determined that 80% of patients have an IgE level of less than 100 kU/L, and 20% had a ps-IgE level of more than 100 kU/L. Additionally, 100% of intent-to-treat (ITT) patents and 100% of completers with a ps-IgE level lower than 100 kU/L were able to tolerate 443 mg of peanut protein after up-dosing. However, of those patients with ps-IgE level >100 kU/L, only 56% of ITT patients and 93% of completers tolerated 443 mg of peanut protein post up-dosing. Additionally, those with a ps-IgE level lower than 100 kU/L had a 0% dropout rate from the study, whereas those patients with a ps-IgE level higher than 100 kU/L had a 40% dropout rate from the study. At entry of the study, the mean skin prick test (SPT) for those patients with a ps-IgE level of less than 100 kU/L was 15 mm, and the mean SPT for those patients with a ps-IgE level of more than 100 kU/L was 13 mm. The mean tolerated dose at entry for patients with a ps-IgE level of less than 100 kU/L was 20 mg, and the mean tolerated dose for those patients with a ps-IgE level of more than 100 kU/L was 16 mg. Generally, patients who don't achieve robust reliable efficacy on OIT are those who cannot tolerate it based on GI symptoms. This will be better understood by phase 3 trials.

Of the 55 patients starting ARC001, baseline psIgE was very high (>100 $kU_A/L$) in 28 patients, and lower (≤100 $kU_A/L$) in 27 patients. In the lower baseline psIgE group, there were no treatment-related withdrawals and all patients met the primary endpoint at the exit DBPCFC. However, in the very high baseline psIgE group (>100 $kU_A/L$), 10 of 28 patients (36%) withdrew due to treatment-related adverse events (gastrointestinal symptoms ranging from oral pruritus to moderate vomiting and/or abdominal pain), and one patient failed the exit DBPCFC. Baseline peanut SPT and screening DBPCFC results were not clinically different between these two groups (≤100 $kU_A/L$ vs >100 $kU_A/L$ baseline psIgE).

Conclusions. In two phase 2 trials, baseline peanut-specific IgE level appears to be predictive of up-dosing completion and treatment response with AR101 in CODIT, as well as a meaningful reduction in drop-out rate from up-dosing and a lower risk for GI symptoms.

Example 8: Oral Immunotherapy for the Treatment of a Peanut Allergy

Study Design

The following study was conducted as a multicenter, double-blind, placebo-controlled phase 3 trial was conducted at 66 sites in 10 countries. Patients aged 4-55 years were considered eligible. All participants had a clinical history of peanut allergy, confirmed by screening DBPCFC, and either serum peanut-specific IgE (psIgE) ≥0.35 $kU_A/L$ by ImmunoCAP™ (Thermo Fisher Scientific, Waltham Mass.) and/or peanut skin prick test mean wheal diameter ≥3 mm larger than the negative control at screening. Key exclusion criteria included a history of medically significant chronic or recurrent gastrointestinal symptoms of any etiology, including eosinophilic esophagitis (EoE); severe or uncontrolled asthma using National Heart, Lung, and Blood Institute definitions; or the use of a prohibited medication. Patients with a history of severe/life-threatening anaphylaxis were permitted, if the episode occurred ≥60 days before screening. Patients living at the same address were excluded from the trial to minimize the chances of inadvertent unblinding or errant administration of the incorrect investigational product. At the end-of-study visit, the exit DBPCFC was to be independently assessed by a physician at the site experienced in the procedure who had not substantially participated in the care of that participant throughout the trial.

Initial Enrollment:

842 Individuals were screened by double blind placebo controlled food challenge (DBPCFC) for allergy to peanut. Individuals who were intolerant of 30 mg or less of peanut protein were enrolled in the study. Individuals who tolerated more than 30 mg of peanut protein were excluded. 551 enrolled individuals were divided 3:1 into peanut protein oral immunotherapy (OIT) and placebo arms. 413 individuals received peanut protein OIT and 138 individuals received placebo. The study population averaged 11.3 years of age (range 4-55), was 57% male, and 80% Caucasian. 407 (74%) had a history of peanut anaphylaxis prior to screening, 53% had asthma, 66% had multiple food allergies, and 43% had peanut-specific IgE levels greater than or equal to 100 kU/L. Baseline median (IQR) values were as follows: peanut skin prick wheal diameter 11.5 (range 9-15) mm; and peanut specific IgE 61.75 (range 16.7-179) kU/L. Of the total study population, 496 were 4-17 years of age. Of the 4-17-year-old age group, 372 individuals received the peanut protein OIT, and 124 individuals received placebo.

Administration:

Both peanut protein and placebo, which were similar in appearance, were administered as a powder in graduated doses provided in pull-apart capsules (0.5, 1, 10, 20, or 100 mg) or foil-laminate sachets (300 mg), according to the procedure described below, and formulated with bulking and flow agents considered generally recognized as safe. Capsules (or sachets) were opened and the content mixed thoroughly with a few spoonfuls of age-appropriate, non-allergenic food, and generally consumed within 4 hours.

Up-Dosing Phase:

The total treatment duration was approximately twelve months and was divided into two phases. During the up-dosing phase, which lasted approximately six months, OIT recipients began receiving daily 3 mg doses of peanut protein and ended the phase receiving daily 300 mg doses of peanut protein, with dose escalations occurring every two weeks. The up-dosing phase consisted of this biweekly progression through the 3, 6, 12, 20, 40, 80, 120, 160, 200, and 240 mg dose levels and could take no more than 40 weeks. All dose escalations occurred in a clinical research center (CRC) or other monitored setting with emergency intervention capabilities. Daily doses were self-administered by the individual at home.

Maintenance Phase:

During the second phase, termed the maintenance phase, which lasted approximately six months, OIT recipients received daily 300 mg doses of peanut protein which they self-administered at home.

Completion:

At the end of the maintenance phase or upon study exit, participants from both the OIT and placebo arms underwent a DBPCFC and blood test.

Results

General:

No deaths or suspected, unexpected serious adverse reactions (SUSARs) were observed. Incidence of reported serious adverse events (SAEs) was low in both arms for the 4-17-year-old age group, with 9 patients in the OIT arm (2.4%) reporting a SAE, 4 of which were possibly-related to treatment (1.1%). Of these 4 patients, 2 experienced severe events, including 1 case of anaphylaxis and 1 case of wheezing. Both of these patients had initial peanut-specific IgE levels greater than 100 kU/L. One patient in the placebo arm was reported to experience a serious adverse event. Over 85% of the OIT patients did not experience systemic hypersensitivity reactions. Of the 14.5% who did experience hypersensitivity reactions, 98.2% had mild or moderate reactions.

Completion Rate in Ages 4-17:

As indicated in Table 3 below, approximately 80% of individuals in the 4-17 year-old OIT arm completed the study. In this arm, 16.7% of the total 4-17 year old group discontinued during the up-dosing phase, and 3.8% during the maintenance phase. One individual discontinued the study due to biopsy-confirmed moderate, non-serious eosinophilic esophagitis (EoE) during the study. No additional cases of EoE were identified in the study. Of the systemic hypersensitivity reactions, seven were investigator-identified anaphylaxis events (six mild, one severe). The four additional individuals discontinued the study for acute viral illness, eye pruritus, headache, or an unknown factor.

TABLE 3

Peanut Protein OIT for Individuals Ages 4-17

|  | Percent total OIT arm | Number of individuals |
|---|---|---|
| Total discontinuations regardless of causality | 20.4% | 76 |
| Discontinuations not related to adverse events | 8.0% | 30 |
| Discontinuations related to adverse events | 12.4% | 46 |
| Gastrointestinal | 6.7% | 25 |
| Systemic hypersensitivity reactions | 2.7% | 10 |
| Respiratory system | 1.1% | 4 |
| Cutaneous | 0.8% | 3 |
| Other | 1.1% | 4 |

Intent-to-Treat Efficacy in Total Study:

The intent-to-treat group includes all individuals enrolled in either the OIT or placebo arms of the study, regardless of treatment adherence, withdrawal from the study, or deviation from the study design. As shown in Table 4, of the 413 individuals in the OIT arm, 73.4% successfully tolerated a 300 mg peanut protein dose in a DBPCFC upon exit from the study, 64.6% successfully tolerated a 600 mg dose in a DBPCFC upon exit from the study, and 48.7% successfully tolerated a 1,000 mg dose in a DBPCFC upon exit from the study. In contrast, only 10.9% of placebo arm individuals successfully tolerated a 300 mg dose in a DBPCFC upon exit from the study, 5.1% successfully tolerated a 600 mg dose in a DBPCFC upon exit from the study, and 3.6% tolerated a 1,000 mg dose in a DBPCFC upon exit from the study. The 95% confidence interval and p-value was calculated as indicated for each dose level.

TABLE 4

|  | 300 mg | 600 mg | 1,000 mg |
| --- | --- | --- | --- |
| OIT Arm (n = 413) | 73.4% | 64.6% | 48.7% |
| Placebo (n = 138) | 10.9% | 5.1% | 3.6% |
| 95% CI difference | (53-72%) | (49.9-69.2%) | (35.7-54.4%) |
| p-value | p < 0.00001 | p < 0.00001 | p < 0.00001 |

Intent-to-Treat Efficacy in 4-17 Year Olds:

This intent-to-treat group of 4-17 year old study participants includes all 4-17 year old individuals enrolled in either the OIT or placebo arms of the study, regardless of treatment adherence, withdrawal from the study, or deviation from the study design. As shown in Table 5, of the 372 individuals in the OIT arm, 76.6% successfully tolerated a 300 mg peanut protein dose in a DBPCFC upon exit from the study, 67.2% successfully tolerated a 600 mg dose in a DBPCFC upon exit from the study, and 50.3% successfully tolerated a 1,000 mg dose in a DBPCFC upon exit from the study. In contrast, only 8.1% of placebo arm individuals successfully tolerated a 300 mg dose in a DBPCFC upon exit from the study, 4.0% successfully tolerated a 600 mg dose in a DBPCFC upon exit from the study, and 2.4% tolerated a 1,000 mg dose in a DBPCFC upon exit from the study. The 95% confidence interval and p-value was calculated as indicated for each dose level.

TABLE 5

|  | 300 mg | 600 mg | 1,000 mg |
| --- | --- | --- | --- |
| OIT Arm (n = 372) | 76.6% | 67.2% | 50.3% |
| Placebo (n = 124) | 8.1% | 4.0% | 2.4% |
| 95% CI Difference | (58.6-78.5%) | (53.0-73.3%) | (38.0-57.7%) |
| p-value | p < 0.00001 | p < 0.00001 | p < 0.00001 |

Figure 3:
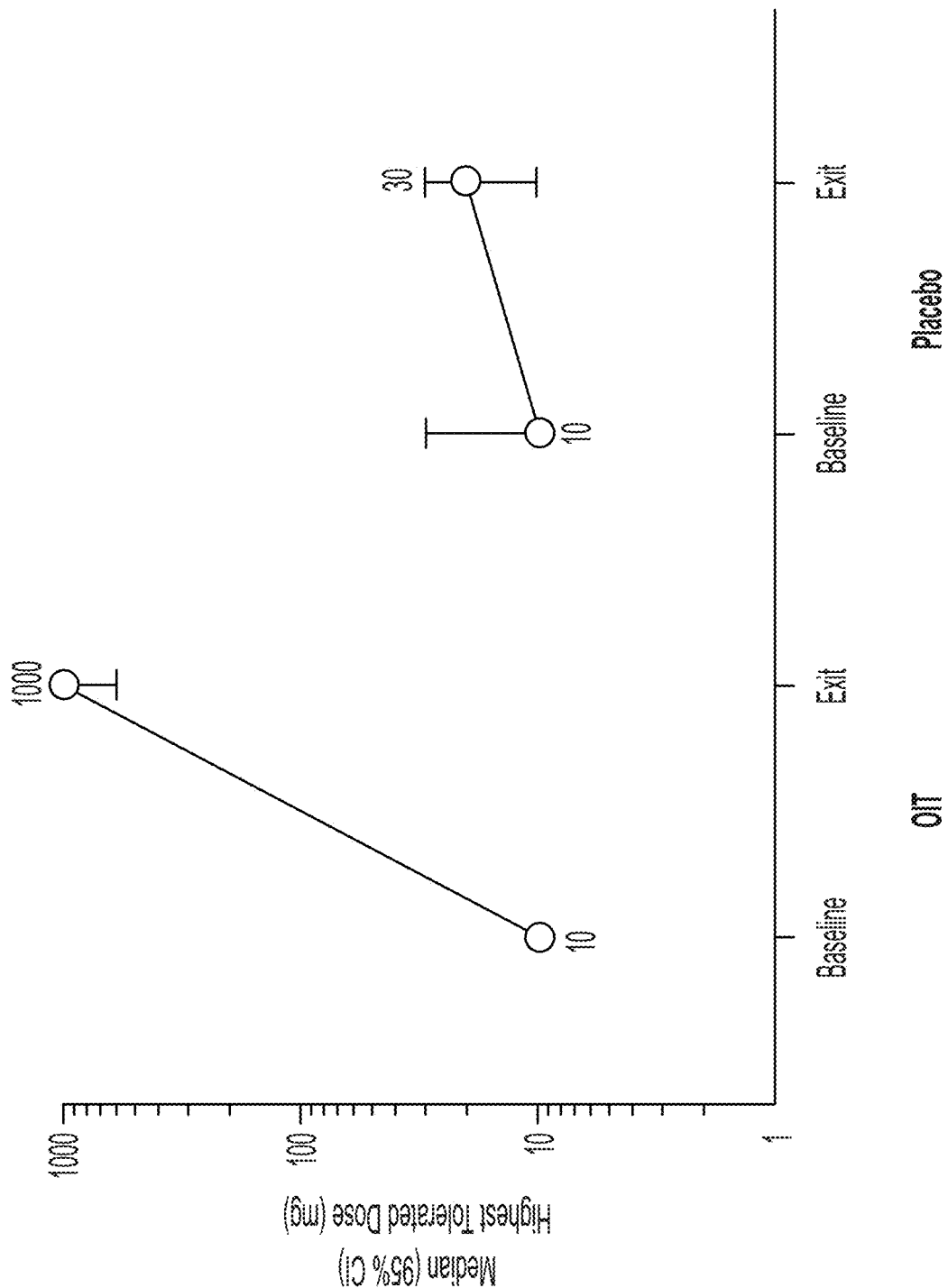
FIG. 3 shows the median amount of peanut protein tolerated in entry and exit peanut challenges for the intent-to-treat population for an oral immunotherapy trial and a placebo.

Further, as indicated in FIG. 3, the median amount of peanut protein tolerated in entry and exit peanut challenges for the intent-to-treat population was significantly different between study arms.

Completer Efficacy:

The completer population includes all individuals enrolled who completed substantially all of the full approximately twelve month study. As shown in Table 6, of the 316 completers in the OIT arm, 95.9% successfully tolerated a 300 mg dose in a DBPCFC upon exit from the study, 84.5% successfully tolerated a 600 mg dose in a DBPCFC upon exit from the study, and 63.6% successfully tolerated a 1,000 mg dose in a DBPCFC upon exit from the study. In contrast, only 11.6% of placebo arm individuals successfully tolerated a 300 mg dose in a DBPCFC upon exit from the study, 5.4% successfully tolerated a 600 mg dose in a DBPCFC upon exit from the study, and 3.9% tolerated a 1,000 mg dose in a DBPCFC upon exit from the study. The 95% confidence interval and p-value was calculated as indicated for each dose level.

TABLE 6

|  | 300 mg | 600 mg | 1,000 mg |
| --- | --- | --- | --- |
| OIT Arm (n = 316) | 95.9% | 84.5% | 63.6% |
| Placebo (n = 129) | 11.6% | 5.4% | 3.9% |
| 95% CI Difference | (75.0-93.5%) | (69.1-89%) | (49.5-69.9%) |
| p-value | p < 0.00001 | p < 0.00001 | p < 0.00001 |

Completer Efficacy in 4-17 Year Olds:

This group includes all 4-17 year old individuals enrolled who completed substantially all of the full approximately twelve month study. As shown in Table 7, of the 296 completers in the OIT arm, 96.3% successfully tolerated a 300 mg dose in a DBPCFC upon exit from the study, 84.5% successfully tolerated a 600 mg dose in a DBPCFC upon exit from the study, and 63.2% successfully tolerated a 1,000 mg dose in a DBPCFC upon exit from the study. In contrast, only 8.6% of placebo arm individuals successfully tolerated a 300 mg dose in a DBPCFC upon exit from the study, 4.3% successfully tolerated a 600 mg dose in a DBPCFC upon exit from the study, and 2.6% tolerated a 1,000 mg dose in a DBPCFC upon exit from the study. The 95% confidence interval and p-value was calculated as indicated for each dose level.

TABLE 7

|  | 300 mg | 600 mg | 1,000 mg |
| --- | --- | --- | --- |
| OIT Arm (n = 296) | 96.3% | 84.5% | 63.2% |
| Placebo (n = 116) | 8.6% | 4.3% | 2.6% |
| 95% CI Difference | (78.0-97.3%) | (69.7-90.6%) | (49.9-71.3%) |
| p-value | p < 0.00001 | p < 0.00001 | p < 0.00001 |

Figure 4A:
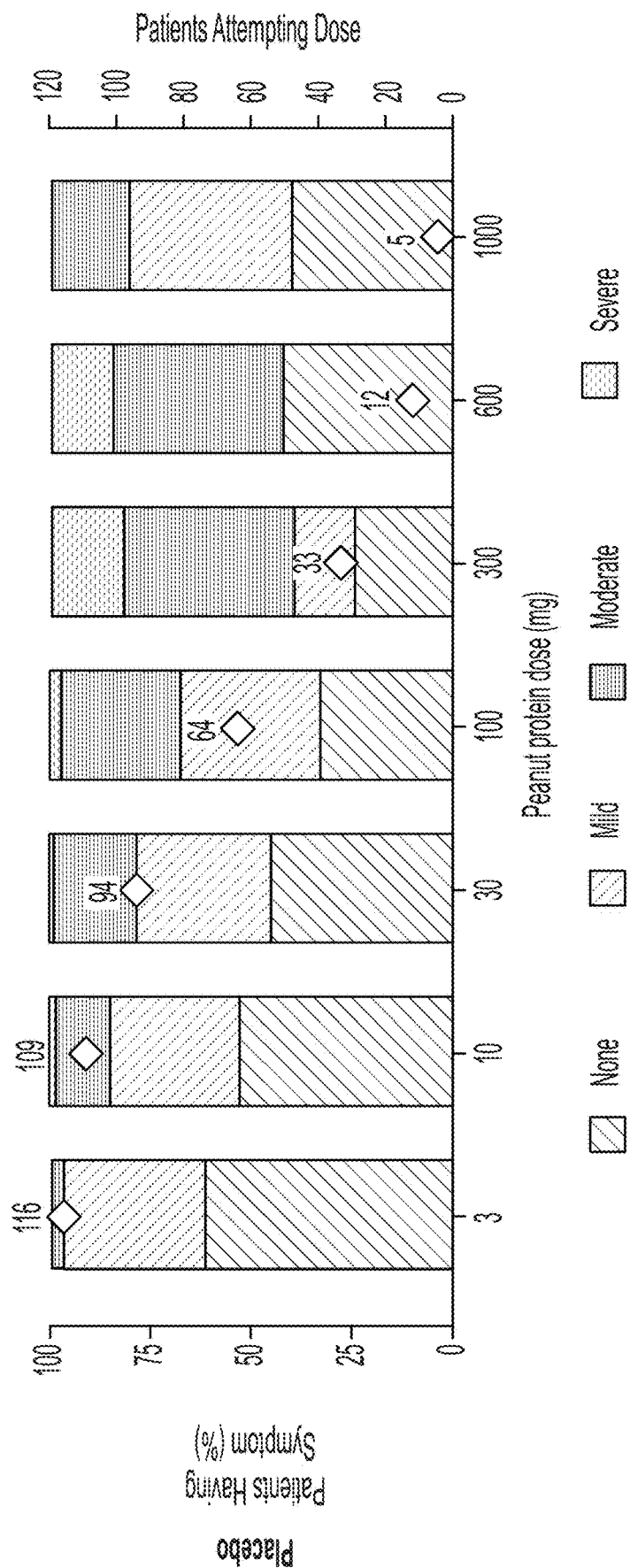
FIG. 4A and FIG. 4B show the symptom severity observed at each indicated peanut protein dose during an exit peanut challenge for a 4-17 year-old completer population of an oral immunotherapy for peanut allergy treatment (FIG. 4B) and a placebo (FIG. 4A). The number of people passing the indicated peanut dose are indicated by a black diamond.
Figure 4B:
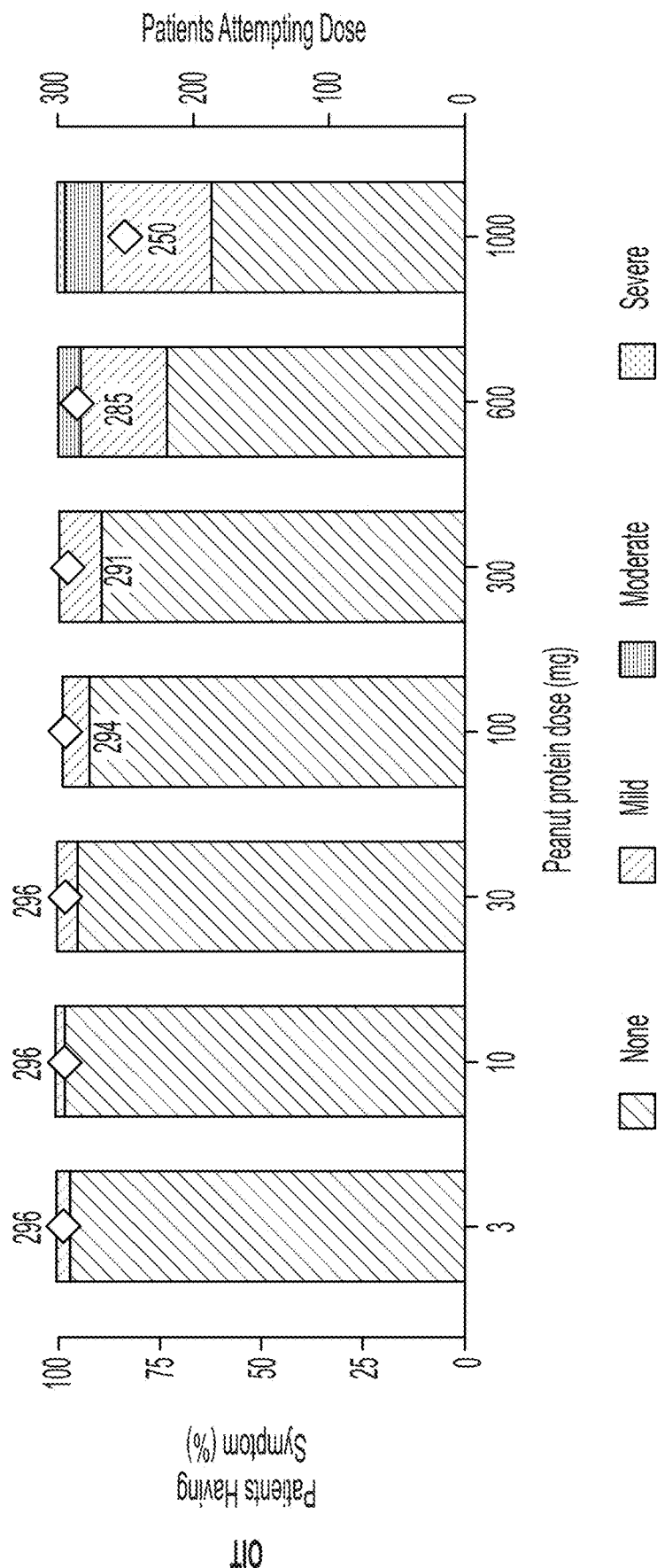

Symptom Severity at Exit Peanut Challenge for 4-17 Year Olds:

Among the 4-17 year old completer population, the severity of symptoms between the OIT and placebo arms was observed during the exit DBPCFC. As shown in FIG. 4, the OIT arm developed far fewer moderate and severe symptoms as compared to the placebo arm. The number of individuals passing the food challenge at the indicated dose is indicated by the black diamond.

Treatment-Emergent Adverse Events for 4-17 Age Group:

The treatment-emergent adverse events (TEAE) profile was observed for the 4-17 age group of both arms. As Table 8 below indicates, the TEAE profile was similar for both the OIT and placebo arms.

TABLE 8

|  | OIT | | Placebo | |
| --- | --- | --- | --- | --- |
|  | Mild/Moderate | Severe | Mild/Moderate | Severe |
| Subjects reporting at least one TEAE | 94.1% | 4.6% | 92.7% | 2.4% |
| Gastrointestinal | 84% | 1.3% | 69% | 0.8% |
| Respiratory, thoracic, and mediastinal | 80% | 0.8% | 72% | 0.0% |
| Infections and infestations | 70% | 0.3% | 73% | 0.0% |
| Skin and subcutaneous tissue | 66% | 1.3% | 55% | 0.0% |
| General disorders and administration site conditions | 37% | 0.0% | 31% | 0.0% |
| Nervous system | 26% | 0.3% | 26% | 0.0% |
| Eye | 20% | 0.3% | 21% | 0.0% |

TABLE 8-continued

| | OIT | | Placebo | |
|---|---|---|---|---|
| | Mild/Moderate | Severe | Mild/Moderate | Severe |
| Immune system | 17% | 0.3% | 9% | 1.6% |
| Injury, poisoning, and procedural complications | 15% | 0.0% | 23% | 0.0% |
| Vascular | 13% | 0.3% | 2% | 0.0% |
| Ear and labyrinth | 13% | 0.3% | 2% | 0.0% |
| Musculoskeletal and connective tissue | 8% | 0.0% | 10% | 0.0% |
| Psychiatric | 5% | 0.0% | 2% | 0.0% |

Figure 5:
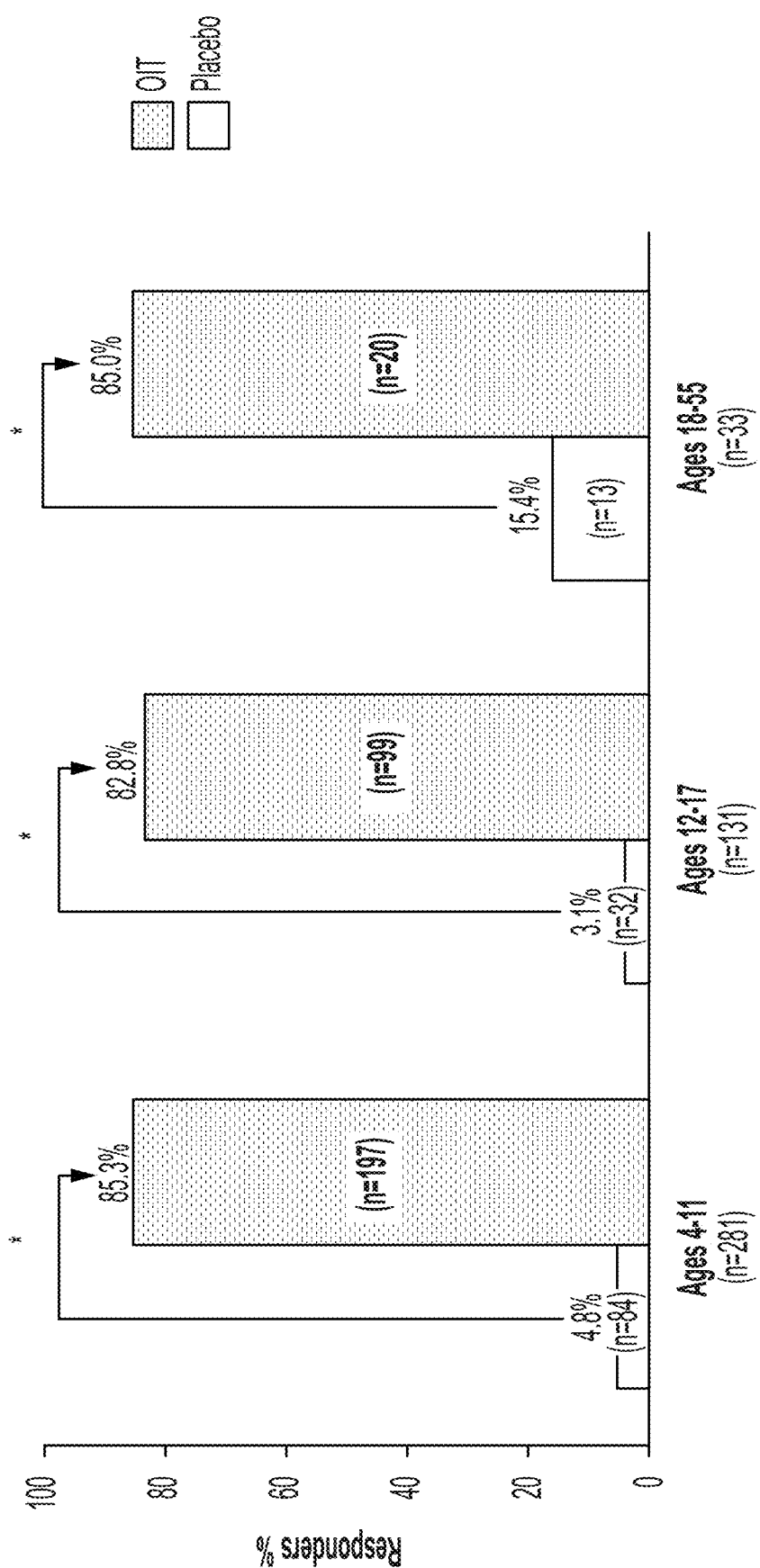
FIG. 5 shows the percentage of subjects in oral immunotherapy for a peanut allergy and placebo arms that tolerate a 600 mg dose of peanut protein during the exit double blind, placebo controlled food challenge (DBPCFC), broken down into the age groups 4-11, 12-17, and 18-55 year old subjects.

Age Profile of Completer Population:

As indicated in FIG. 5, patients across age cohorts (i.e., ages 4-11, 12-17, and 18-55 years old) responded similarly to the peanut protein OIT as measured by tolerance to a 600 mg peanut protein dose during an exit DBPCFC. 600 mg of peanut protein is approximately equivalent to the peanut protein in two whole peanuts.

Measurement of Peanut-Specific IgE in 4-17 Year Olds:

Patients 4-17 years old had their peanut-specific IgE serum levels measured at the beginning of therapy, prior to administration of the first dose. As shown in Table 9 below, 4-17-year-old patients with starting peanut-specific IgE levels less than or equal to 100 kU/L, after one year of OIT (6 months up-dosing phase and 6 months of maintenance phase), were more likely to become tolerant of a 1,000 mg peanut protein dose during the completion DBPCFC, were less likely to discontinue due to gastrointestinal adverse events, and were less likely to have a severe hypersensitivity reaction as compared with individuals with a starting peanut-specific IgE level greater than 100 kU/L.

TABLE 9

| | Intent-to-treat population | | Completer population | |
|---|---|---|---|---|
| Patient Outcomes, N (%) | Peanut-specific IgE ≤100 kU/L (N = 213) | Peanut-specific IgE >100 kU/L (N = 159) | Peanut-specific IgE ≤ 100 kU/L (N = 176) | Peanut-specific IgE > 100 kU/L (N = 120) |
| Tolerated 1,000 mg dose | 117 (55%) | 70 (44%) | 117 (67%) | 70 (58%) |
| Discontinued due to gastrointestinal adverse events | 10 (5) | 15 (9%) | N/A | N/A |
| Experienced a severe systemic hypersensitivity reaction | 0 | 1 (0.6%) | N/A | N/A |

Figure 6A:
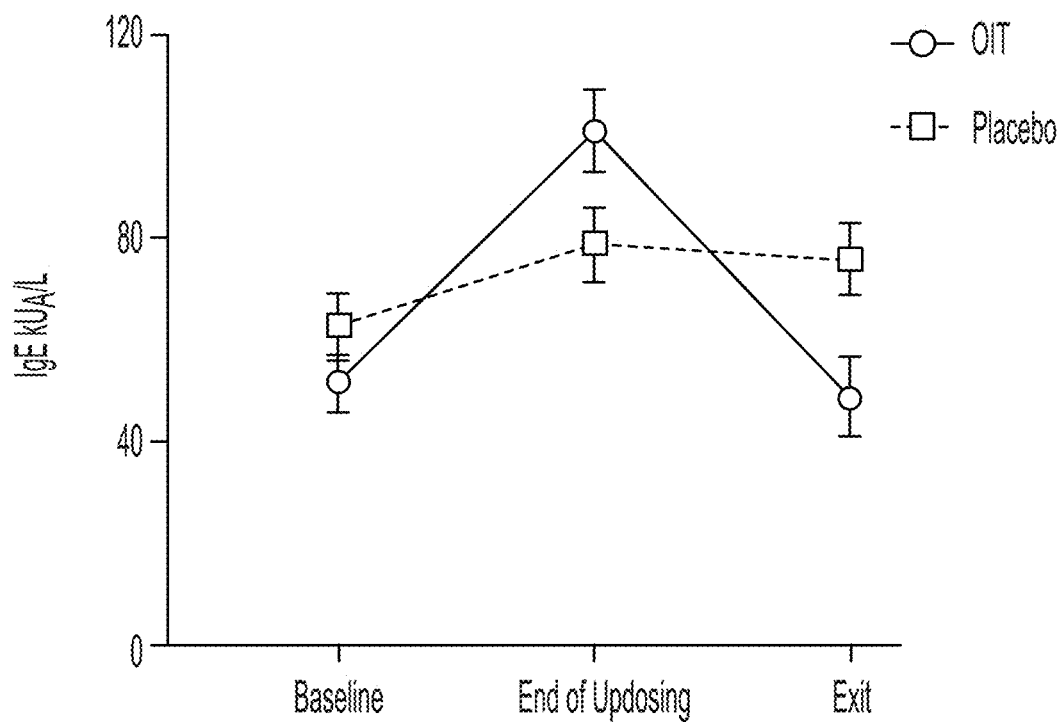
FIG. 6A shows the average level of peanut-specific IgE for the oral immunotherapy and placebo arms at start (baseline), at the end of the up-dosing phase, and at study exit
Figure 6B:
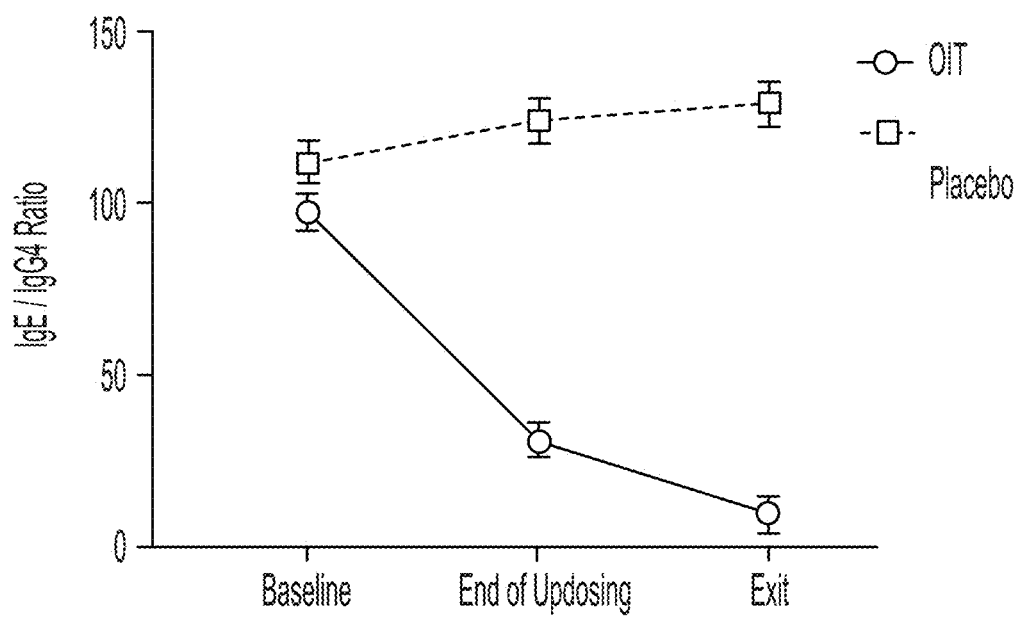
FIG. 6B shows the average peanut-specific IgE to IgG4 ratio for the oral immunotherapy and placebo arms at start (baseline), at the end of the up-dosing phase, and at study exit.
Figure 6C:
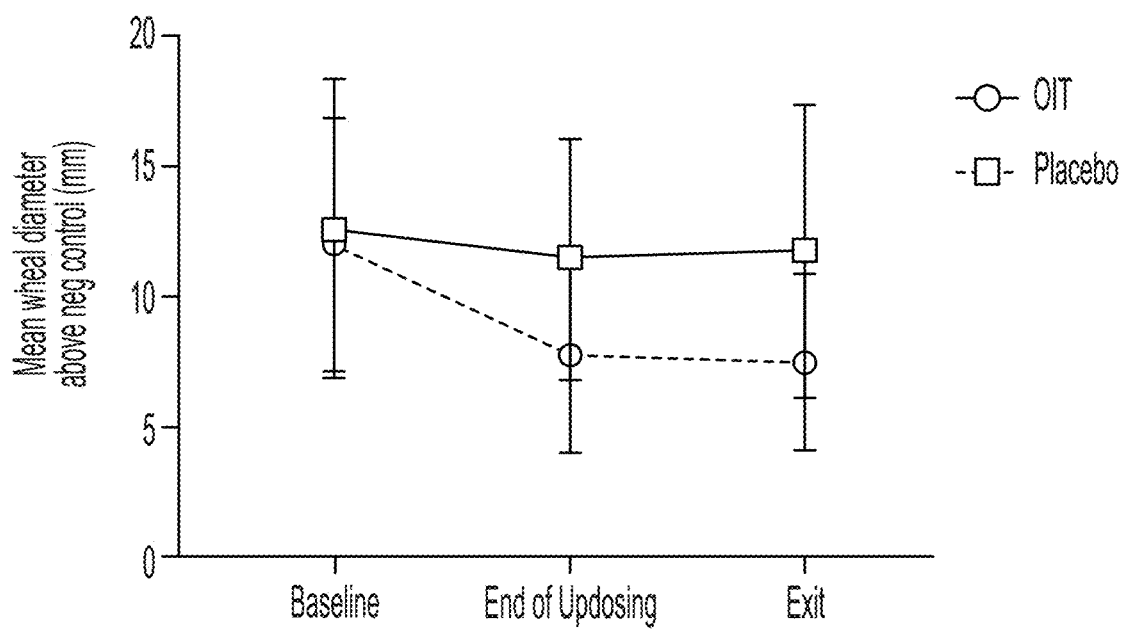
FIG. 6C shows the reaction to the skin prick test as measured by mean wheal diameter above negative control for oral immunotherapy and placebo arms at start (baseline), at the end of the up-dosing phase, and at study exit.
Figure 6D:
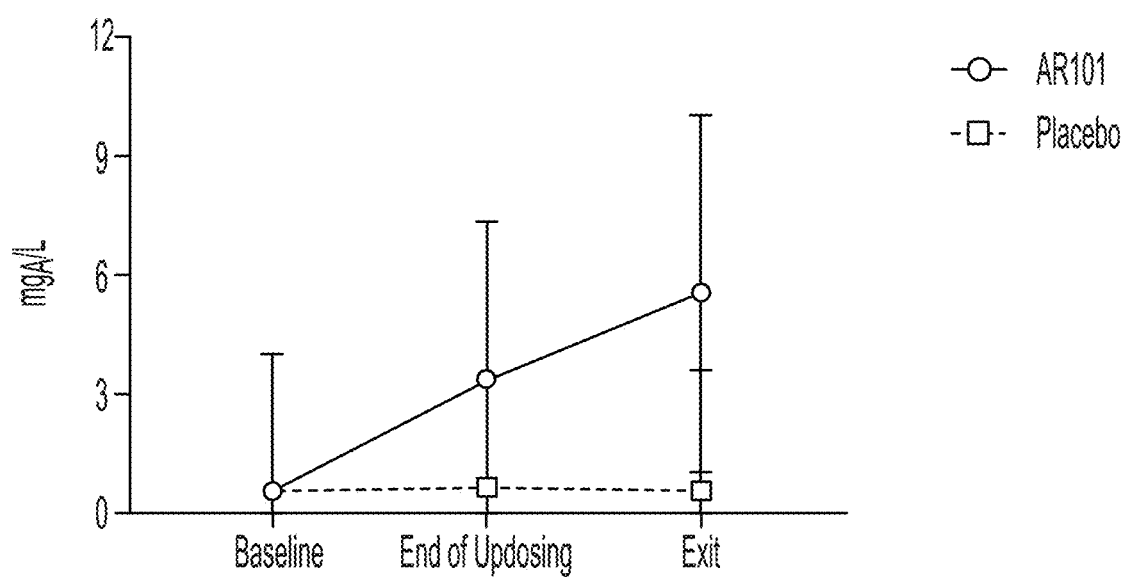
FIG. 6D shows that peanut-specific IgG4 increased during the course of the study for the OIT recipients, whereas peanut-specific IgG4 levels remained approximately stable for recipients of the placebo formulation.

Immune Modulation in Patients Age 4-17:

Patients 4-17-years-old receiving the peanut protein OIT demonstrated marked immune modulation. As shown in FIG. 6A, OIT patients displayed increased peanut-specific IgE levels during the up-dosing phase, while they experienced ongoing reductions in peanut-specific serum IgE levels during the maintenance phase. Placebo group peanut-specific serum IgE levels did not change appreciably over the year of study. Further, as shown in FIG. 6B, the ratio of peanut-specific IgE to IgG4 (IgE/IgG4 ratio) changed dramatically over the course of the study for the OIT recipients, while no decrease was observed for the placebo group. As shown in FIG. 6C, OIT recipients displayed weaker response to the skin prick test as measured by mean wheal diameter above negative control. Finally, as shown in FIG. 6D, peanut-specific IgG4 increased during the course of the study for the OIT recipients, whereas peanut-specific IgG4 levels remained approximately stable for recipients of the placebo formulation. These data are also reported in Table 10 below.

TABLE 10

| | Baseline | | End of Up-dosing | | End of Study | | |
|---|---|---|---|---|---|---|---|
| | OIT | Placebo | OIT | Placebo | OIT | Placebo | P-value |
| Peanut Skin Prick Test (mm) | 12.0 (4.9) | 12.7 (5.7) | 7.8 (3.7) | 11.4 (4.6) | 7.5 (3.4) | 11.8 (5.6) | <0.0001 |
| | n = 371 | n = 124 | n = 304 | n = 116 | n = 292 | n = 115 | |
| psIgE (kUA/L) | 52.0 (6.1) | 62.7 (6.2) | 101.3 (8.1) | 78.8 (7.2) | 48.6 (7.8) | 76.1 (6.9) | 0.5044 |
| | n = 371 | n = 121 | n = 305 | n = 116 | n = 272 | n = 104 | |
| psIgG4 (mgA/L) | 0.5 (3.5) | 0.6 (3.4) | 3.3 (4.0) | 0.6 (2.8) | 5.6 (4.5) | 0.6 (3.0) | <0.0001 |
| | n = 353 | n = 116 | n = 305 | n = 116 | n = 274 | n = 104 | |
| psIgE/psIgG$_4$ | 97.6 (5.1) | 111.9 (6.3) | 30.3 (4.6) | 124.1 (6.8) | 8.8 (5.3) | 129.3 (6.5) | <0.0001 |
| | n = 353 | n = 115 | n = 305 | n = 116 | n = 272 | n = 104 | |

Epinephrine Usage.

It was further observed that baseline peanut-specific IgE levels were a good indicator for assessing the likelihood of a patient experiencing an allergic reaction requiring the use of epinephrine. Specifically, the mean baseline psIgE in patients receiving the peanut OIT that had an allergic reaction requiring the use of epinephrine was 266 kU/L, whereas the mean baseline psIgE in patients receiving OIT that did not have an allergic reaction requiring the use of epinephrine was 72 kU/L.

All document disclosed herein are incorporated by reference in their entirety for all purposes.

The invention claimed is:

1. A method of treating a subject for a peanut allergy, comprising:
    measuring a level of peanut-specific IgEs in the subject;
    selecting the subject for treatment based on the measured level of peanut-specific IgEs in the subject being at or below a predetermined threshold; and
    administering to the selected subject at least one dose of an allergenic peanut composition.

2. The method of claim 1, wherein the predetermined threshold for the level of peanut-specific IgEs is about 100 kU/L.

3. The method of claim 2, wherein the level of peanut-specific IgEs is measured prior to initiating treatment of the peanut allergy.

4. The method of claim 2, wherein the dose is administered to the subject as part of an oral immunotherapy dosing regimen.

5. The method of claim 4, wherein the dose is administered to the subject during an initial escalation phase of the oral immunotherapy dosing regimen.

6. The method of claim 4, wherein the dose is administered to the subject during an up-dosing phase of the oral immunotherapy dosing regimen.

7. The method of claim 4, wherein the dose is administered to the subject during a maintenance phase of the oral immunotherapy dosing regimen.

8. A method of treating a subject for a peanut allergy, comprising:
    measuring a level of peanut-specific IgEs in the subject;
    administering to the subject at least one dose of an allergenic peanut composition;
    determining whether the subject is in need of heightened monitoring for an allergic reaction based on the measured level of peanut-specific IgEs in the subject being above a predetermined threshold; and
    monitoring the subject for an allergic reaction, wherein the monitoring is heightened compared to a subject having a level of peanut-specific IgEs at or below the predetermined threshold.

9. A method of adjusting a dose of an allergenic peanut composition, comprising:
    administering a first dose of the allergenic peanut composition to a subject with a peanut allergy;
    measuring a level of peanut-specific IgEs in the subject after administration of the first dose;
    selecting a second dose of the allergenic peanut composition based on the first dose and the measured level of peanut-specific IgEs in the subject; and
    administering the second dose of the allergenic peanut composition to the subject.

10. The method of claim 1, wherein the subject is a human.

11. The method of claim 1, wherein the subject is about 17 years of age or younger.

12. The method of claim 11, wherein the subject is about 4 years of age to about 17 years of age.

13. The method of claim 1, wherein the level of peanut-specific IgEs corresponds to a level as measured by a fluorescence enzyme immunoassay auto-analyzer.

14. The method of claim 1, wherein the level of peanut-specific IgEs is measured by a fluorescence enzyme immunoassay auto-analyzer.

15. The method of claim 8, wherein the predetermined threshold of the level of peanut-specific IgEs is about 100 kU/L.

16. The method of claim 8, wherein heightened monitoring comprises a longer clinical visit following administration of the dose compared to a subject having a level of peanut-specific IgEs at or below the predetermined threshold.

17. The method of claim 8, wherein heightened monitoring comprises active monitoring for the allergic reaction.

18. The method of claim 17, wherein active monitoring comprises measuring a heart rate, blood pressure, respiratory rate, or blood oxygen.

19. The method of claim 8, wherein the allergic reaction is hypersensitivity, anaphylaxis, a gastrointestinal symptom, or eosinophilic esophagitis.

20. The method of claim 8, wherein the dose is administered to the subject as part of an oral immunotherapy dosing regimen.

21. The method of claim 20, wherein the dose is administered to the subject during an initial escalation phase of the oral immunotherapy regimen.

22. The method of claim 20, wherein the dose is administered to the subject during an up-dosing phase of an oral immunotherapy regimen.

23. The method of claim 20, wherein the dose is administered to the subject during a maintenance phase of an oral immunotherapy regimen.

24. The method of claim 8, wherein the level of peanut-specific IgEs in the subject is measured prior to initiating treatment of the subject.

25. The method of claim 8, wherein the level of peanut-specific IgEs in the subject is measured during the course of treatment.

26. The method of claim 8, wherein the subject is a human.

27. The method of claim 8, wherein the subject is about 17 years of age or younger.

28. The method of claim 27, wherein the subject is about 4 years of age to about 17 years of age.

29. The method of claim 8, wherein the level of peanut-specific IgEs corresponds to a level as measured by a fluorescence enzyme immunoassay auto-analyzer.

30. The method of claim 8, wherein the level of peanut-specific IgEs is measured by a fluorescence enzyme immunoassay auto-analyzer.

31. The method of claim 9, wherein the second dose is lower than the first dose if the level of peanut-specific IgEs is above a predetermined threshold.

32. The method of claim 9, wherein administration of the second dose is delayed if the level of peanut-specific IgEs is above a predetermined threshold.

33. The method of claim 9, wherein the second dose is the same as the first dose if the level of peanut-specific IgEs is above a predetermined threshold.

34. The method of claim 9, wherein the second dose is increased relative to the first dose if the level of peanut-specific IgEs is at or below the predetermined threshold.

35. The method of claim 31, wherein the predetermined threshold is about 100 kU/L.

36. The method of claim 32, wherein the predetermined threshold is about 100 kU/L.

37. The method of claim 33, wherein the predetermined threshold is about 100 kU/L.

38. The method of claim 34, wherein the predetermined threshold is about 100 kU/L.

39. The method of claim 9, wherein the subject is a human.

40. The method of claim 9, wherein the subject is about 17 years of age or younger.

41. The method of claim 40, wherein the subject is about 4 years of age to about 17 years of age.

42. The method of claim 9, wherein the level of peanut-specific IgEs corresponds to a level as measured by a fluorescence enzyme immunoassay auto-analyzer.

43. The method of claim 9, wherein the level of peanut-specific IgEs is measured by a fluorescence enzyme immunoassay auto-analyzer.

* * * * *

UNITED STATES PATENT AND TRADEMARK OFFICE
CERTIFICATE OF CORRECTION

Page 1 of 1

PATENT NO. : 11,369,676 B2
APPLICATION NO. : 16/178502
DATED : June 28, 2022
INVENTOR(S) : Stephen G. Dilly It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 120 days.

Signed and Sealed this
Eleventh Day of February, 2025

Coke Morgan Stewart
*Acting Director of the United States Patent and Trademark Office*